(12) United States Patent
Hagiwara et al.

(10) Patent No.: US 9,273,364 B2
(45) Date of Patent: Mar. 1, 2016

(54) TRANSGENIC REPORTER SYSTEM THAT REVEALS EXPRESSION PROFILES AND REGULATION MECHANISMS OF ALTERNATIVE SPLICING IN MAMMALIAN ORGANISMS

(75) Inventors: Masatoshi Hagiwara, Kyoto (JP); Akihide Takeuchi, Kyoto (JP)

(73) Assignee: Kyoto University, Kyoto (JP)

( * ) Notice: Subject to any disclaimer, the term of this patent is extended or adjusted under 35 U.S.C. 154(b) by 0 days.

(21) Appl. No.: 13/700,890

(22) PCT Filed: May 31, 2011

(86) PCT No.: PCT/JP2011/003059
§ 371 (c)(1),
(2), (4) Date: Feb. 15, 2013

(87) PCT Pub. No.: WO2011/152043
PCT Pub. Date: Dec. 8, 2011

(65) Prior Publication Data
US 2013/0137099 A1    May 30, 2013

Related U.S. Application Data

(60) Provisional application No. 61/350,420, filed on Jun. 1, 2010.

(51) Int. Cl.
*C12Q 1/68* (2006.01)
*C12N 15/10* (2006.01)
*C12N 15/00* (2006.01)
*C12N 15/01* (2006.01)

(52) U.S. Cl.
CPC .......... *C12Q 1/6897* (2013.01); *C12N 15/1086* (2013.01)

(58) Field of Classification Search
None
See application file for complete search history.

(56) References Cited

U.S. PATENT DOCUMENTS 7,928,283 B2 * 4/2011 Kuroyanagi et al. ............. 800/3
2009/0286246 A1 11/2009 Hood et al.

FOREIGN PATENT DOCUMENTS

WO    2007/149870 A2 * 12/2007 ............... C12Q 1/68

OTHER PUBLICATIONS

Ristevski, "Making Better Transgenic Models" 29 Molecular Biotechnology 153-163 (2005).*
Montoliu, "Gene Transfer Strategies in Animal Transgenesis" 4(1) Cloning and Stem Cells 39-46 (2002).*
Cameron, "Recent Advances in Transgenic Technology" 7 Molecular Biotechnology 253-265 (1997).*
Smith, "Gene transfer in higher animals: theoretical considerations and key concepts" 99 Journal of Biotechnology 1-22 (2002).*
Niemann, "Transgenic farm animals get off the ground" 7 Transgenic Research 73-75 (1998).*
Sigmund, "Viewpoint: Are Studies in Genetically Altered Mice Out of Control?" 20 Arteriosclerosis, Thrombosis, and Vascular Biology 1425-1429 (2000).*
Prelle et al., "Establishment of Pluripotent Cell Lines from Vertebrate Species—Present Status and Future Prospects" 165 Cells Tissues Organs 220-236 (1999).*
Brook "A bi-chromatic fluorescent assay to measure splicing efficiency in Myotonic Dystrophy" 3 Medizinische Genetik 426 (2009).*
Terpe, "Overview of tag protein fusions: from molecular and biochemical fundamentals to commercial systems" 60 Applied Microbiology and Biotechnology 523-533 (2003).*
Kuroyanagi et al., "The Fox-1 Family and SUP-12 Coordinately Regulate Tissue-Specific Alternative Splicing In Vivo" 27(24) Moleculear and Cellular Biology 8612+8621 (2007).*
Bonano, et al., "Imaging the alternative silencing of FGFR2 exon IIIb in vivo," *RNA*, vol. 12(12), pp. 2073-2079.
Kishore, et al., "Rapid generation of splicing reporters with pSpliceExpress," *Gene*, vol. 427(1-2), pp. 104-110 (Dec. 31, 2008).
Baraniak, et al., "Fox-2 Mediates Epithelial Cell-Specific Fibroblast Growth Factor Receptor 2 Exon Choice," *Mol Cell Biol.*, vol. 26(4), pp. 1209-1222 (Feb. 2006).
Black, "Mechanisms of Alternative Pre-Messenger RNA Splicing," *Annu Rev Biochem.*, vol. 72, pp. 291-336. (2003, Epub Feb. 27, 2003).
Boulin, et al., "Reporter Gene Fusions" *WormBook*, pp. 1-23 (Apr. 5, 2006).
Carstens, et al., "An Intronic Splicing Silencer Causes Skipping of the IIIb Exon of Fibroblast Growth Factor Receptor 2 through Involvement of Polypyrimidine Tract Binding Protein," *Mol Cell Biol.*, vol. 20(19), pp. 7388-7400 (Oct. 2000).
Chen, et al., "Tra2βI regulates P19 neuronal differentiation and the splicing of FGF-2R and GluR-B minigenes," *Cell Biol Int.*, vol. 28(11), pp. 791-799 (2004).
De Moerlooze, et al., "An important role for the IIIB isoform of fibroblast growth factor receptor 2 (FGFR2) in mesenchymal-epithelial signaling during mouse organogenesis," *Development*, vol. 127(3), pp. 483-492 (Feb. 2000).
Del Gatto-Konczak, et al., "hnRNP A1 Recruited to an Exon in Vivo Can Function as an Exon Splicing Silencer," *Mol Cell Biol.*, vol. 19(1), pp. 251-260 (Jan. 1999).

(Continued)

*Primary Examiner* — Nancy J Leith
(74) *Attorney, Agent, or Firm* — Kilpatrick Townsend & Stockton LLP

(57) ABSTRACT

An object of the present invention is to develop a new alternative splicing reporter system and to provide a method for detecting alternative splicing patterns in a mammalian multicellular organism more precisely, a method for identifying efficiently substances and gene regions that affect alternative splicing in a mammalian multicellular organism, and the like by utilizing the alternative splicing reporter system. Specifically, the present invention relates to a method for detecting alternative splicing in a mammalian multicellular organism, and a method for identifying substances and gene regions that affect alternative splicing in a mammalian multicellular organism, which use a DNA construct in which at least two different reporter genes are inserted into a specific gene that undergoes alternative splicing, or a combination of DNA constructs (a combination of at least two different DNA constructs) in which DNA construct a reporter gene is inserted into a specific gene that undergoes alternative splicing.

10 Claims, 14 Drawing Sheets

(56) References Cited

OTHER PUBLICATIONS

Ellis, et al. "Regulated Tissue-specific Alternative Splicing of Enhanced Green Fluorescent Protein Transgenes Conferred by α-Tropomyosin Regulatory Elements in Transgenic Mice," *J Biol Chem.*, vol. 279(35), pp. 36660-36669 (Aug. 27, 2004, Epub Jun. 11, 2004).

Eswarakumar, et al., "The IIIc alternative of Fgfr2 is a positive regulator of bone formation," *Development*, vol. 129(16), pp. 3783-3793 (Aug. 2002).

Eswarakumar, et al., "Cellular signaling by fibroblast growth factor receptors," *Cytokine Growth Factor Rev.*, vol. 16(2), pp. 139-149 (Apr. 2005, Epub Feb. 1, 2005).

Gilbert, et al., "Control of BEK and K-SAM Splice Sites in Alternative Splicing of the Fibroblast Growth Factor Receptor 2 pre-mRNA," *Mol Cell Biol.*, vol. 13(9), pp. 5461-5468 (Sep. 1993).

Hovhannisyan, et al., "Heterogeneous Ribonucleoprotein M Is a Splicing Regulatory Protein That Can Enhance or Silence Splicing of Alternatively Spliced Exons," *J Biol Chem.*, vol. 282(50), pp. 36265-36274 (Dec. 14, 2007, Epub Oct. 24, 2007).

Kuroyanagi, et al. "Transgenic alternative-splicing reporters reveal tissue-specific expression profiles and regulation mechanisms in vivo" *Nat Methods.*, vol. 3(11), pp. 909-915 (Nov. 2006).

Kuroyanagi, et al., "Visualization and genetic analysis of alternative splicing regulation in vivo using fluorescence reporters in transgenic Caenorhabditis elegans," *Nat Protoc.*, vol. 5(9), pp. 1495-1517 (Sep. 2010, Epub Aug. 5, 2010)

Matlin, et al., "Understanding Alternative Splicing: Towards a Cellular Code," *Nat Rev Mol Cell Biol.*, vol. 6(5), pp. 386-398 (May 2005).

Mauger, et al., "hnRNP H and hnRNP F Complex with Fox2 to Silence Fibroblast Growth Factor Receptor 2 Exon IIIc," *Mol Cell Biol.*, vol. 28(17), pp. 5403-5419 (Sep. 2008, Epub Jun. 23, 2008).

Newman, et al., "Identification of RNA-binding proteins that regulate FGFR2 splicing through the use of sensitive and specific dual color fluorescence minigene assays," *RNA*, vol. 12(6), pp. 1129-1141 Jun. 2006, Epub Apr. 7, 2006).

Nojima, et al., "Herpesvirus protein ICP27 switches PML isoform by altering mRNA splicing," *Nucleic Acids Res.*, vol. 37(19), pp. 6515-6527 (Oct. 2009, Epub Sep. 3, 2009).

Nojima, et al., "Drug screening by visualization of RNA splicing," *Saibo Kogaku.*, vol. 29(2), pp. 161-167 (Jan. 2010).

Ornitz, et al., "Receptor Specificity of the Fibroblast Growth Factor Family," *J Biol Chem.*, vol. 271(25), pp. 15292-15297 (Jun. 21, 1996).

Pan, et al., "Deep surveying of alternative splicing complexity in the human transcriptome by high-throughput sequencing," *Nat Genet.*, vol. 40(12), pp. 1413-1415 (Dec. 2008, Epub Nov. 2, 2008).

Savagner, et al., "Alternative Splicing in Fibroblast Growth Factor Receptor 2 Is Associated with Induced Epithelial-Mesenchymal Transition in Rat Bladder Carcinoma Cells," *Mol Biol Cell.*, vol. 5(8), pp. 851-862 (Aug. 1994).

Sheives, et al., "Identification of cells deficient in signaling-induced alternative splicing by use of somatic cell genetics " *RNA.*, vol. 8(12), pp. 1473-1481 (Dec. 2002).

Stoilov, et al. "A high-throughput screening strategy identifies cardiotonic steroids as alternative splicing modulators," *Proc Natl Acad Sci USA*, vol. 105(32), pp. 11218-11223 (Aug. 12, 2008, Epub Aug. 4, 2008).

Takeuchi, et al., "Splicing Reporter Mice Revealed the Evolutionary Conserved Switching Mechanism of Tissue-Specific Alternative Exon Selection," *PLoS One*, vol. 5(6), 14 pages (Jun. 3, 2010).

Wang, et al. "Systematic Identification and Analysis of Exonic Splicing Silencers," *Cell.*, vol. 119(6), pp. 831-845 (Dec. 17, 2004).

Wang, et al., "Alternative isoform regulation in human tissue transcriptomes," *Nature*, vol. 456(7221), pp. 470-476 (Nov. 27, 2008).

Warzecha, et al., "ESRP1 and ESRP2 Are Epithelial Cell-Type-Specific Regulators of FGFR2 Splicing," *Mol Cell.*, vol. 33(5), pp. 591-601 (Mar. 13, 2009).

Zhang, et al., "Receptor Specificity of the Fibroblast Growth Factor Family," *J Biol Chem.*, vol. 281(23), pp. 15694-15700 (Jun. 9, 2006, Epub Apr. 4, 2006).

International Search Report for PCT/JP2011/003059, 2 pages, mailed Aug. 16, 2011.

Orengo et al., "A bichromatic fluorescent reporter for cell-based screens of alternative splicing", *Nucleic Acids Research*, vol. 34, No. 22, e148, 10 pages (2006).

\* cited by examiner

Fig. 3
A
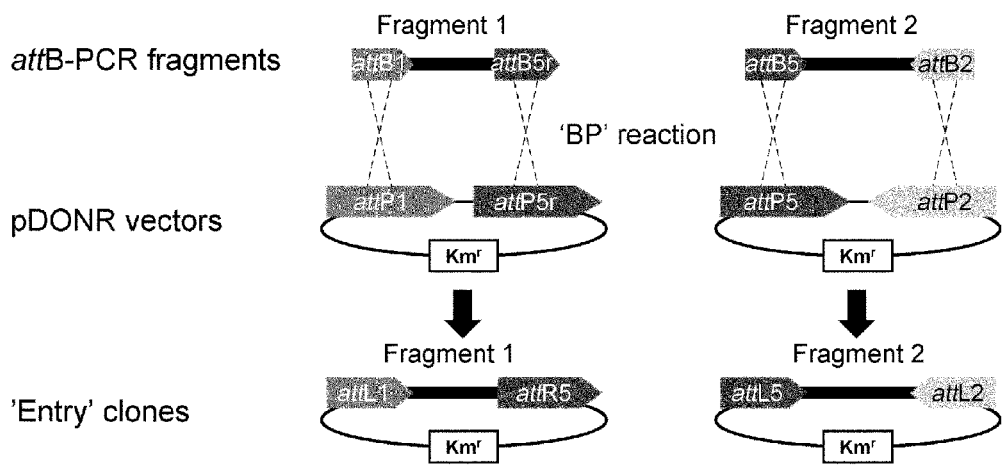
B
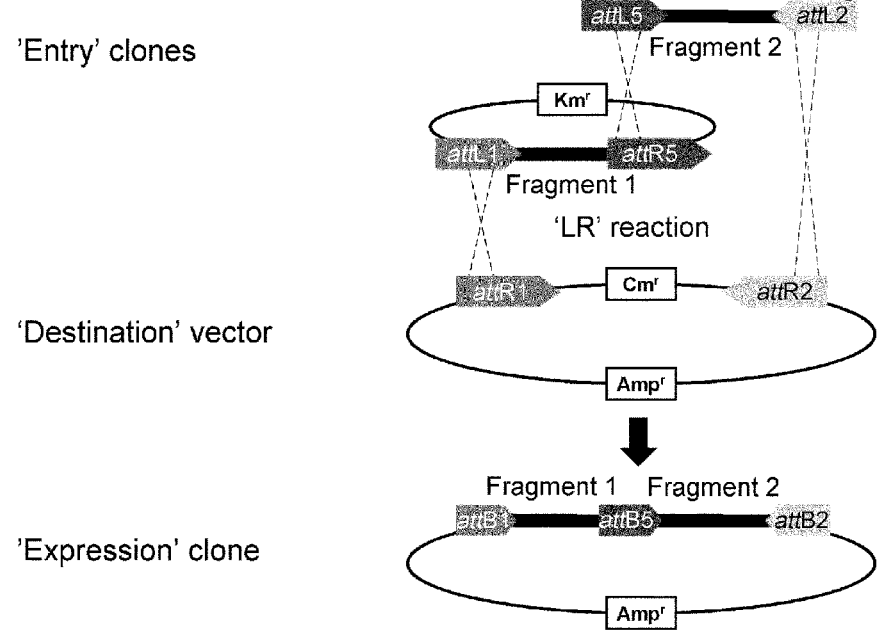

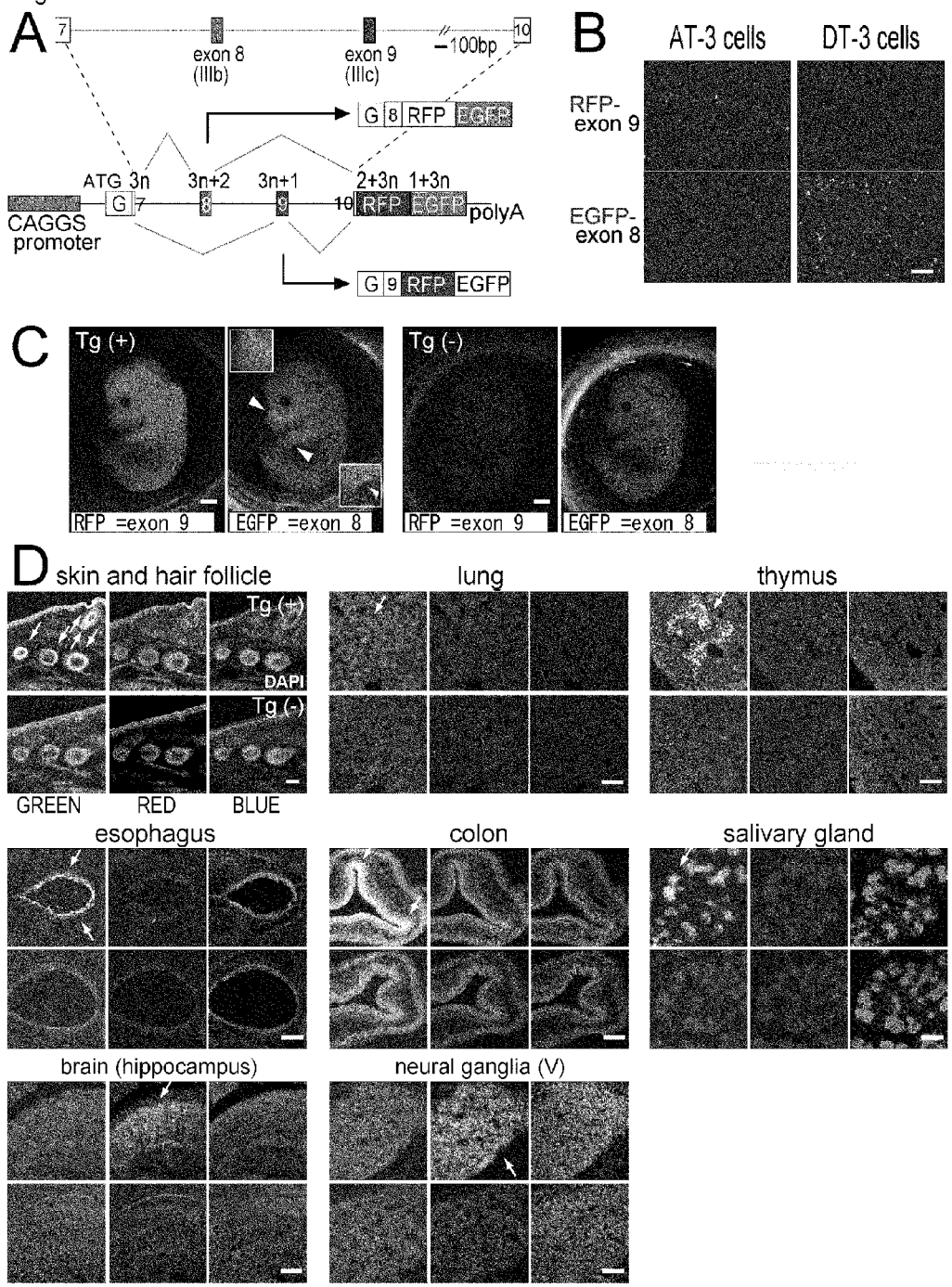

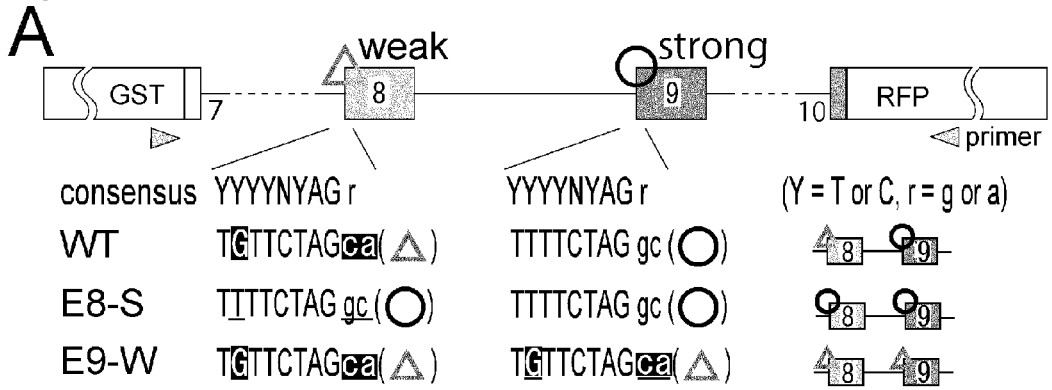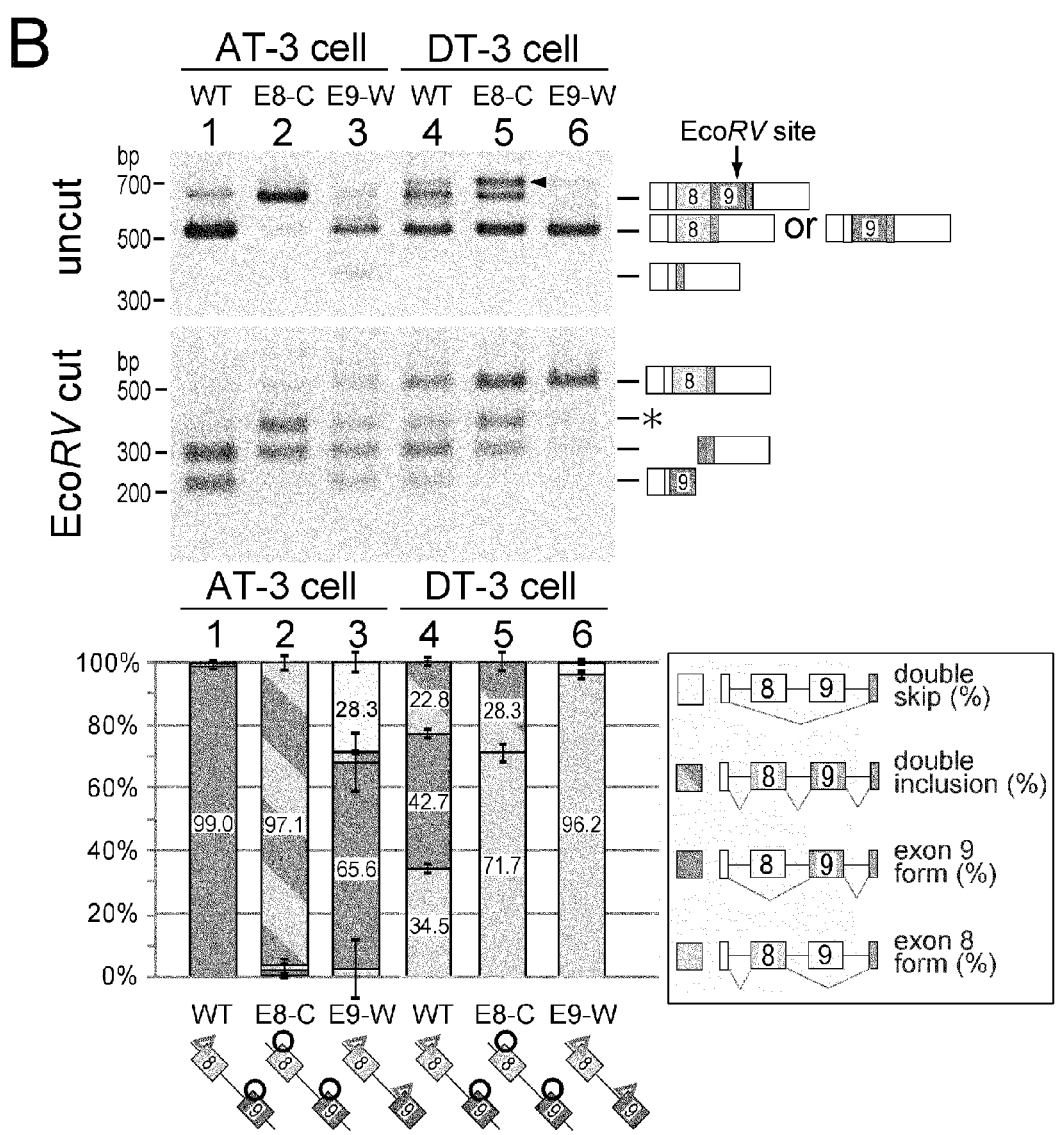

Fig. 9
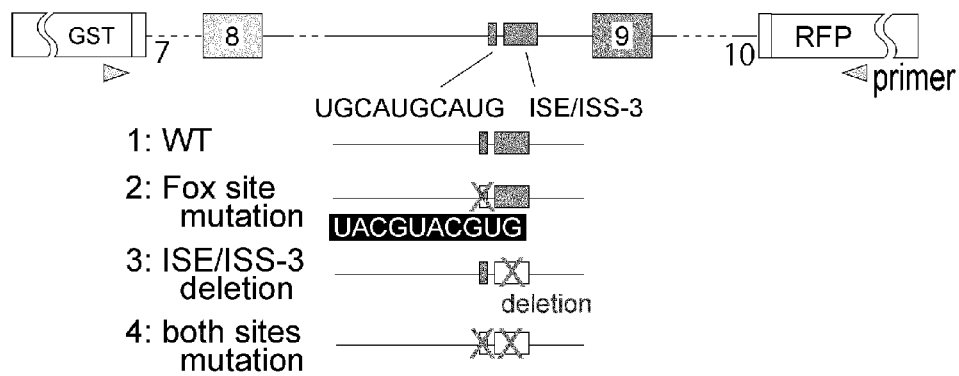
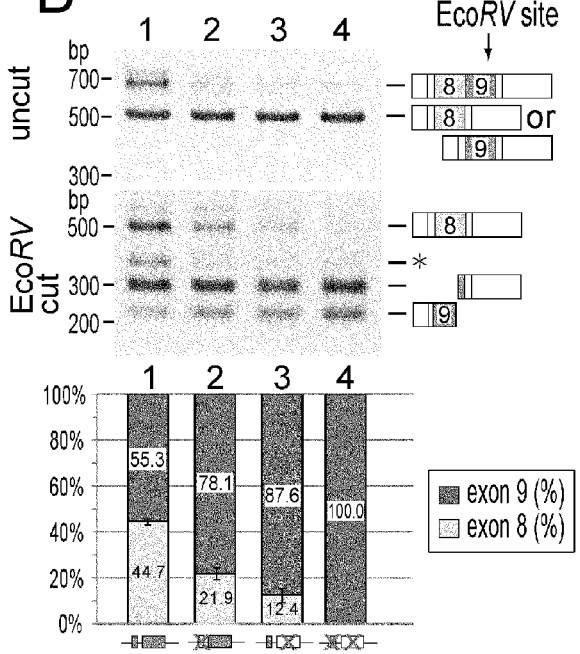
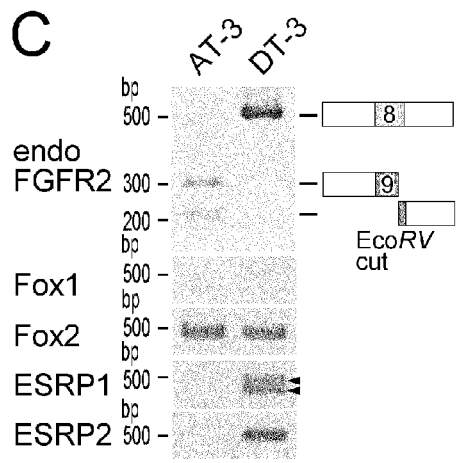

Fig. 10
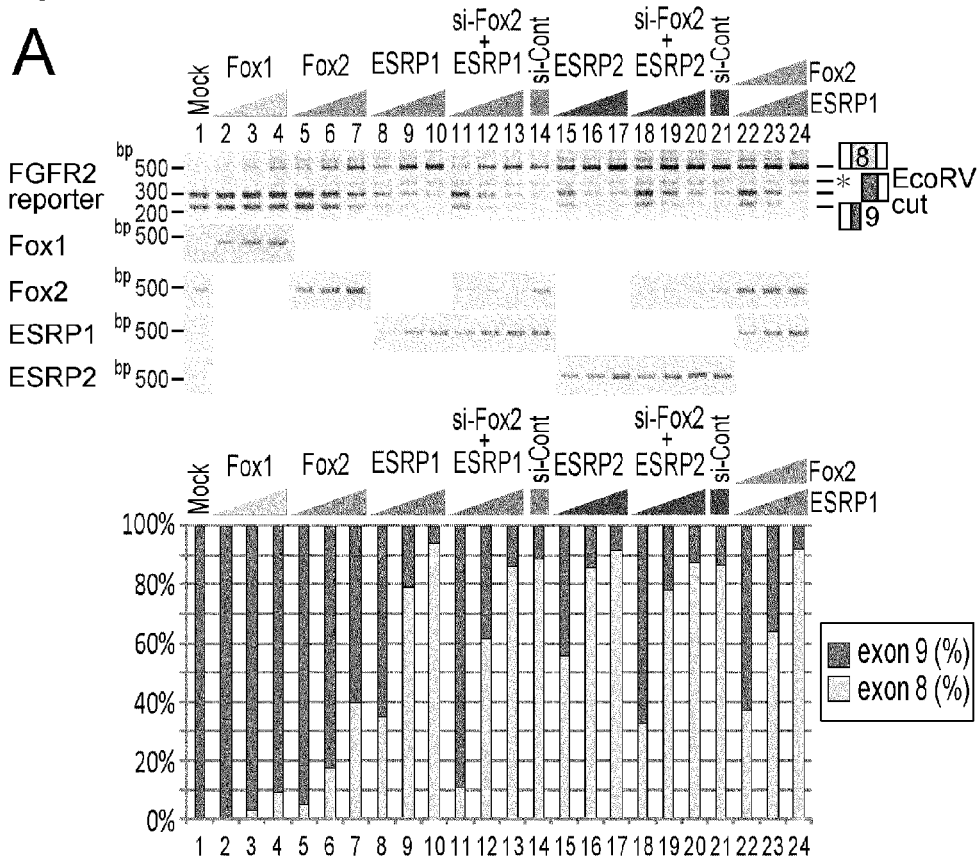
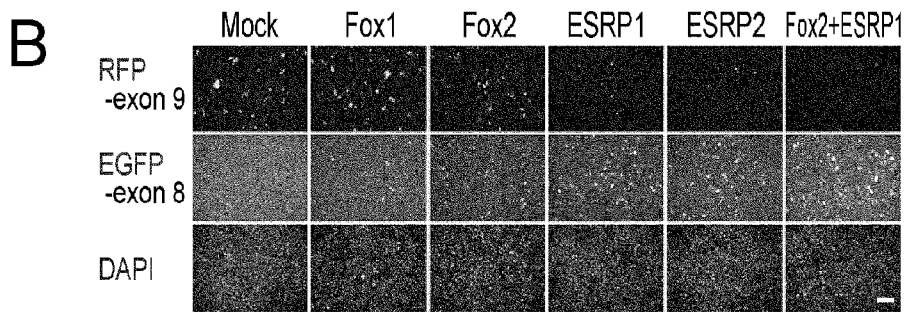
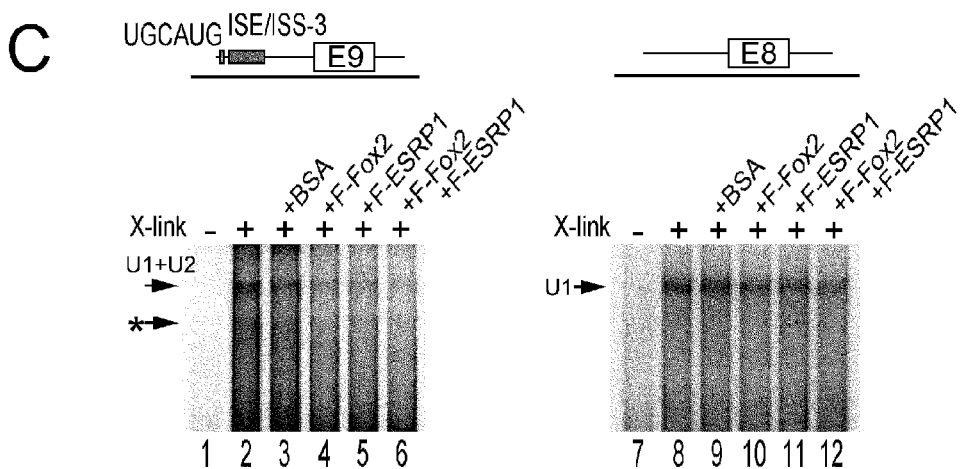

Fig. 12
A
Non-Epithelial or Mesenchymal regulation
: "default" selection of "primary" exon
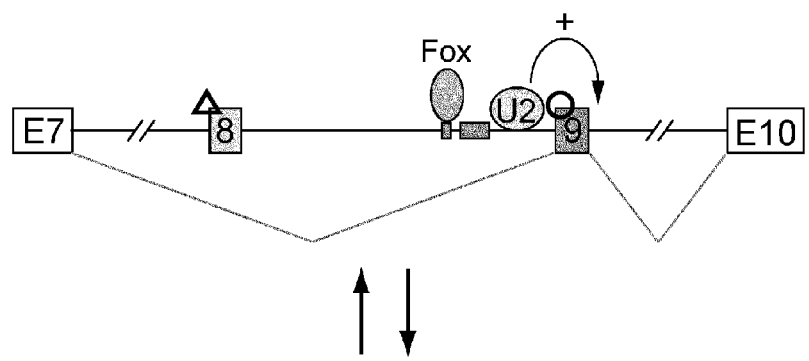
Epithelial regulation
: "alternative" selection of "secondary" exon
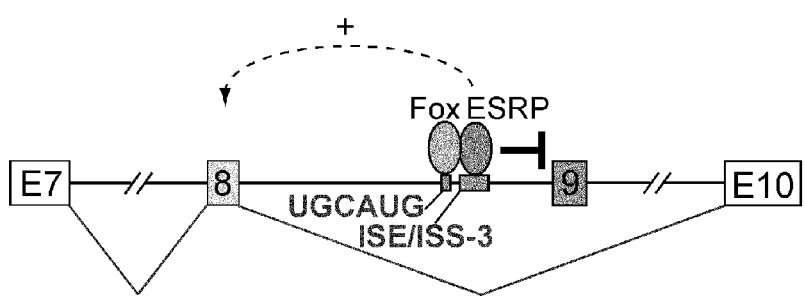
B
| nematode | mammals |
|---|---|
| Fox-1/Asd-1<br>*egl-15* exon 5b<br>(Sup-12 (=mRBM24)<br>*egl-15* exon 5a<br>muscle)<br>non-muscular tissues | Fox1/Fox2<br>*FGFR2* exon 9<br>(ESRP1&2 (=RBM35a&b)<br>*FGFR2* exon 8<br>epithelia)<br>non-epithelial tissues |

SEQUENCE LISTING

<160> NUMBER OF SEQ ID NOS: 43

<210> SEQ ID NO 1
<211> LENGTH: 14
<212> TYPE: DNA
<213> ORGANISM: Artificial Sequence
<220> FEATURE:
<223> OTHER INFORMATION: an artificially synthesized primer sequence
<220> FEATURE:
<221> NAME/KEY: misc_feature
<222> LOCATION: (13)..(14)
<223> OTHER INFORMATION: NN cannot be AA, AG, or GA.

<400> SEQUENCE: 1

```
aaaaagcagg ctnn                                                        14

<210> SEQ ID NO 2
<211> LENGTH: 21
<212> TYPE: DNA
<213> ORGANISM: Artificial Sequence
<220> FEATURE:
<223> OTHER INFORMATION: an artificially synthesized primer sequence

<400> SEQUENCE: 2
aaaaagcagg ctccaccatg g                                                21

<210> SEQ ID NO 3
<211> LENGTH: 13
<212> TYPE: DNA
<213> ORGANISM: Artificial Sequence
<220> FEATURE:
<223> OTHER INFORMATION: an artificially synthesized primer sequence

<400> SEQUENCE: 3
tatacaaagt tgt                                                         13

<210> SEQ ID NO 4
<211> LENGTH: 29
<212> TYPE: DNA
<213> ORGANISM: Artificial Sequence
<220> FEATURE:
<223> OTHER INFORMATION: an artificially synthesized primer sequence

<400> SEQUENCE: 4
ggggacaagt ttgtacaaaa aagcaggct                                        29

<210> SEQ ID NO 5
<211> LENGTH: 26
<212> TYPE: DNA
<213> ORGANISM: Artificial Sequence
<220> FEATURE:
<223> OTHER INFORMATION: an artificially synthesized primer sequence

<400> SEQUENCE: 5
ggggacaact tttgtataca aagttg                                           26

<210> SEQ ID NO 6
<211> LENGTH: 12
<212> TYPE: DNA
<213> ORGANISM: Artificial Sequence
<220> FEATURE:
<223> OTHER INFORMATION: an artificially synthesized primer sequence

<400> SEQUENCE: 6
atacaaaagt tg                                                          12

<210> SEQ ID NO 7
<211> LENGTH: 12
<212> TYPE: DNA
<213> ORGANISM: Artificial Sequence
<220> FEATURE:
<223> OTHER INFORMATION: an artificially synthesized primer sequence

<400> SEQUENCE: 7
agaaagctgg gt                                                          12

<210> SEQ ID NO 8
<211> LENGTH: 26
<212> TYPE: DNA
```

```
<213> ORGANISM: Artificial Sequence
<220> FEATURE:
<223> OTHER INFORMATION: an artificially synthesized primer sequence

<400> SEQUENCE: 8
ggggacaact ttgtatacaa aagttg                                         26

<210> SEQ ID NO 9
<211> LENGTH: 29
<212> TYPE: DNA
<213> ORGANISM: Artificial Sequence
<220> FEATURE:
<223> OTHER INFORMATION: an artificially synthesized primer sequence

<400> SEQUENCE: 9
ggggaccact ttgtacaaga aagctgggt                                      29

<210> SEQ ID NO 10
<211> LENGTH: 17
<212> TYPE: DNA
<213> ORGANISM: Artificial Sequence
<220> FEATURE:
<223> OTHER INFORMATION: an artificially synthesized primer sequence

<400> SEQUENCE: 10
tgtggccgtt tacgtcg                                                   17

<210> SEQ ID NO 11
<211> LENGTH: 18
<212> TYPE: DNA
<213> ORGANISM: Artificial Sequence
<220> FEATURE:
<223> OTHER INFORMATION: an artificially synthesized primer sequence

<400> SEQUENCE: 11
tttacttgta cagctcgt                                                  18

<210> SEQ ID NO 12
<211> LENGTH: 20
<212> TYPE: DNA
<213> ORGANISM: Artificial Sequence
<220> FEATURE:
<223> OTHER INFORMATION: an artificially synthesized primer sequence

<400> SEQUENCE: 12
ggagccgtac tggaactgag                                                20

<210> SEQ ID NO 13
<211> LENGTH: 18
<212> TYPE: DNA
<213> ORGANISM: Artificial Sequence
<220> FEATURE:
<223> OTHER INFORMATION: an artificially synthesized primer sequence

<400> SEQUENCE: 13
ttaggcgccg gtggagtg                                                  18

<210> SEQ ID NO 14
<211> LENGTH: 23
<212> TYPE: DNA
<213> ORGANISM: Artificial Sequence
<220> FEATURE:
<223> OTHER INFORMATION: an artificially synthesized primer sequence

<400> SEQUENCE: 14
ggctgcccta cctcaaggtc ctg                                            23
```

<210> SEQ ID NO 15
<211> LENGTH: 25
<212> TYPE: DNA
<213> ORGANISM: Artificial Sequence
<220> FEATURE:
<223> OTHER INFORMATION: an artificially synthesized primer sequence

<400> SEQUENCE: 15
ctctctcaca ggcgctgggt tgcag                                    25

<210> SEQ ID NO 16
<211> LENGTH: 46
<212> TYPE: DNA
<213> ORGANISM: Artificial Sequence
<220> FEATURE:
<223> OTHER INFORMATION: an artificially synthesized primer sequence

<400> SEQUENCE: 16
gcatgccttg atagagtggc ctctcctgtt gaaccttccc ctggag             46

<210> SEQ ID NO 17
<211> LENGTH: 46
<212> TYPE: DNA
<213> ORGANISM: Artificial Sequence
<220> FEATURE:
<223> OTHER INFORMATION: an artificially synthesized primer sequence

<400> SEQUENCE: 17
ctccagggga aggttcaaca ggagaggcca ctctatcaag gcatgc             46

<210> SEQ ID NO 18
<211> LENGTH: 42
<212> TYPE: DNA
<213> ORGANISM: Artificial Sequence
<220> FEATURE:
<223> OTHER INFORMATION: an artificially synthesized primer sequence

<400> SEQUENCE: 18
gaggttctct atattcggaa tgttactttt gaggatgctg gg                 42

<210> SEQ ID NO 19
<211> LENGTH: 42
<212> TYPE: DNA
<213> ORGANISM: Artificial Sequence
<220> FEATURE:
<223> OTHER INFORMATION: an artificially synthesized primer sequence

<400> SEQUENCE: 19
cccagcatcc tcaaaagtaa cattccgaat atagagaacc tc                 42

<210> SEQ ID NO 20
<211> LENGTH: 42
<212> TYPE: DNA
<213> ORGANISM: Artificial Sequence
<220> FEATURE:
<223> OTHER INFORMATION: an artificially synthesized primer sequence

<400> SEQUENCE: 20
gcttcgtttg ttttctctgc cgccggtgtt aacaccacgg ac                 42

<210> SEQ ID NO 21
<211> LENGTH: 42
<212> TYPE: DNA
<213> ORGANISM: Artificial Sequence
<220> FEATURE:

<223> OTHER INFORMATION: an artificially synthesized primer sequence

<400> SEQUENCE: 21
gtccgtggtg ttaacaccgg cggcagagaa aacaaacgaa gc          42

<210> SEQ ID NO 22
<211> LENGTH: 45
<212> TYPE: DNA
<213> ORGANISM: Artificial Sequence
<220> FEATURE:
<223> OTHER INFORMATION: an artificially synthesized primer sequence

<400> SEQUENCE: 22
ctgcatggtt gacagttctg ccaccaacat actgctcttt ctctc        45

<210> SEQ ID NO 23
<211> LENGTH: 45
<212> TYPE: DNA
<213> ORGANISM: Artificial Sequence
<220> FEATURE:
<223> OTHER INFORMATION: an artificially synthesized primer sequence

<400> SEQUENCE: 23
gagagaaaga gcagtatgtt ggtggcagaa ctgtcaacca tgcag        45

<210> SEQ ID NO 24
<211> LENGTH: 49
<212> TYPE: DNA
<213> ORGANISM: Artificial Sequence
<220> FEATURE:
<223> OTHER INFORMATION: an artificially synthesized primer sequence

<400> SEQUENCE: 24
gggccaattt ttccatgtgt tcaatttacg tacgttctag gtggtgacg    49

<210> SEQ ID NO 25
<211> LENGTH: 49
<212> TYPE: DNA
<213> ORGANISM: Artificial Sequence
<220> FEATURE:
<223> OTHER INFORMATION: an artificially synthesized primer sequence

<400> SEQUENCE: 25
cgtcaccacc tagaacgtac gtaaattgaa cacatggaaa aattggccc    49

<210> SEQ ID NO 26
<211> LENGTH: 30
<212> TYPE: DNA
<213> ORGANISM: Artificial Sequence
<220> FEATURE:
<223> OTHER INFORMATION: an artificially synthesized primer sequence

<400> SEQUENCE: 26
taggtggtga cgccgaatct cctgatggcc                        30

<210> SEQ ID NO 27
<211> LENGTH: 30
<212> TYPE: DNA
<213> ORGANISM: Artificial Sequence
<220> FEATURE:
<223> OTHER INFORMATION: an artificially synthesized primer sequence

<400> SEQUENCE: 27
ggccatcagg agattcggcg tcaccaccta                        30

```
<210> SEQ ID NO 28
<211> LENGTH: 18
<212> TYPE: DNA
<213> ORGANISM: Artificial Sequence
<220> FEATURE:
<223> OTHER INFORMATION: an artificially synthesized primer sequence

<400> SEQUENCE: 28
ggcctttgca gggctggc                                                     18

<210> SEQ ID NO 29
<211> LENGTH: 21
<212> TYPE: DNA
<213> ORGANISM: Artificial Sequence
<220> FEATURE:
<223> OTHER INFORMATION: an artificially synthesized primer sequence

<400> SEQUENCE: 29
ggagccgtac tggaactgag g                                                 21

<210> SEQ ID NO 30
<211> LENGTH: 23
<212> TYPE: DNA
<213> ORGANISM: Artificial Sequence
<220> FEATURE:
<223> OTHER INFORMATION: an artificially synthesized primer sequence

<400> SEQUENCE: 30
ggcaccgcca cacagacaga tga                                               23

<210> SEQ ID NO 31
<211> LENGTH: 23
<212> TYPE: DNA
<213> ORGANISM: Artificial Sequence
<220> FEATURE:
<223> OTHER INFORMATION: an artificially synthesized primer sequence

<400> SEQUENCE: 31
tcctggttgg cctggcacaa cag                                               23

<210> SEQ ID NO 32
<211> LENGTH: 27
<212> TYPE: DNA
<213> ORGANISM: Artificial Sequence
<220> FEATURE:
<223> OTHER INFORMATION: an artificially synthesized primer sequence

<400> SEQUENCE: 32
caacaactcc tgacgcaatg gttcagc                                           27

<210> SEQ ID NO 33
<211> LENGTH: 25
<212> TYPE: DNA
<213> ORGANISM: Artificial Sequence
<220> FEATURE:
<223> OTHER INFORMATION: an artificially synthesized primer sequence

<400> SEQUENCE: 33
gattttacgg ccctctacca cggtg                                             25

<210> SEQ ID NO 34
<211> LENGTH: 28
<212> TYPE: DNA
<213> ORGANISM: Artificial Sequence
<220> FEATURE:
<223> OTHER INFORMATION: an artificially synthesized primer sequence
```

```
<400> SEQUENCE: 34
caggagatgc ctttatccag atgaagtc                                      28

<210> SEQ ID NO 35
<211> LENGTH: 22
<212> TYPE: DNA
<213> ORGANISM: Artificial Sequence
<220> FEATURE:
<223> OTHER INFORMATION: an artificially synthesized primer sequence

<400> SEQUENCE: 35
cagtattgta ggccaggccc tg                                            22

<210> SEQ ID NO 36
<211> LENGTH: 27
<212> TYPE: DNA
<213> ORGANISM: Artificial Sequence
<220> FEATURE:
<223> OTHER INFORMATION: an artificially synthesized primer sequence

<400> SEQUENCE: 36
cctacacagc caccattgaa gacattc                                       27

<210> SEQ ID NO 37
<211> LENGTH: 22
<212> TYPE: DNA
<213> ORGANISM: Artificial Sequence
<220> FEATURE:
<223> OTHER INFORMATION: an artificially synthesized primer sequence

<400> SEQUENCE: 37
ggtgaggtag cccacagtag tg                                            22

<210> SEQ ID NO 38
<211> LENGTH: 12
<212> TYPE: DNA
<213> ORGANISM: Artificial Sequence
<220> FEATURE:
<223> OTHER INFORMATION: cDNA oligo/RNAs mixture sequence

<400> SEQUENCE: 38
cggagtgcaa tg                                                       12

<210> SEQ ID NO 39
<211> LENGTH: 15
<212> TYPE: DNA
<213> ORGANISM: Artificial Sequence
<220> FEATURE:
<223> OTHER INFORMATION: cDNA oligo/RNAs mixture sequence

<400> SEQUENCE: 39
cagatactac acttg                                                    15

<210> SEQ ID NO 40
<211> LENGTH: 10
<212> TYPE: DNA
<213> ORGANISM: Mus musculus

<400> SEQUENCE: 40
tgttctagca                                                          10

<210> SEQ ID NO 41
<211> LENGTH: 10
<212> TYPE: DNA
<213> ORGANISM: Mus musculus
```

```
<400> SEQUENCE: 41
ttttctaggc                                                                10

<210> SEQ ID NO 42
<211> LENGTH: 10
<212> TYPE: RNA
<213> ORGANISM: Mus musculus

<400> SEQUENCE: 42
ugcaugcaug                                                                10

<210> SEQ ID NO 43
<211> LENGTH: 10
<212> TYPE: RNA
<213> ORGANISM: Artificial Sequence
<220> FEATURE:
<223> OTHER INFORMATION: an artificially synthesized sequence

<400> SEQUENCE: 43
uacguacgug                                                                10
```

TRANSGENIC REPORTER SYSTEM THAT REVEALS EXPRESSION PROFILES AND REGULATION MECHANISMS OF ALTERNATIVE SPLICING IN MAMMALIAN ORGANISMS

TECHNICAL FIELD

The present invention relates to a method for detecting alternative splicing in a mammalian multicellular organism, a method for identifying substances and gene regions that affect alternative splicing in a mammalian multicellular organism, and the like.

PRIORITY

The present application is a U.S. National Phase of PCT/JP2011/003059, filed May 31, 2011, which claims the benefit of U.S. Application No. 61/350,420, filed on Jun. 1, 2010, the entire contents of which are incorporated by reference herein in their entirety.

REFERENCE TO SEQUENCE LISTING

This application includes a Sequence Listing as a text file named "87331-023710US-858742 SEQ LIST.txt" created Nov. 28, 2012, and containing 9,581 bytes. The material contained in this text file is incorporated by reference in its entirety for all purposes.

BACKGROUND ART

Genome projects have shown that metazoans generate a hugely diverse proteome from a limited number of genes. This finding underscores the importance of alternative splicing, through which a single gene can generate multiple structurally and functionally distinct protein isoforms. Moreover, recent transcriptome analyses with splicing-sensitive microarrays or deep sequencers have revealed that alternative splicing occurs in more than 90% of multi-exon genes in human (NPL 1) and over 60% of these cases are regulated in a tissue- and cell type-specific manner (NPL 2). Alternative splicing is regulated by auxiliary cis-elements with regulatory proteins that enhance or repress splicing of adjacent exons (NPL 3, 4) however, the mechanism by which a number of genes are regulated in various tissue-specific manner by a limited number of regulatory factors remains unclear.

In mammals, fibroblast growth factor-receptor 2 (FGFR2) is one of the best characterized gene in which mutually exclusive alternative splicing produces two isoforms. Exon 8 (also termed IIIb) isoform is specifically expressed in epithelial tissues, whereas exon 9 (or IIIc) isoform is selected in non-epithelial or mesenchymal tissues (NPL 5, 6). The structural difference between two splice isoforms markedly affects the specificity of ligand-receptor binding (NPL 7, 8, 9), and exon switching is shown to be essential for development in the mouse (NPL 10, 11). Several factors have been identified which positively or negatively regulate either of alternative exons of FGFR2 independently. For exon 8 regulation, Del Gatto-Konczak et al. found that heterogeneous nuclear ribonucleoprotein, hnRNP A1, binds to exon 8 (also termed K-SAM exon) as ESS (exonic splicing silencer) and represses its inclusion (NPL 12). Carstens et al. found the polypyrimidine tract binding protein (PTB) represses exon 8 inclusion through ISS-1 and ISS-2 (intronic splicing silencers-1 and 2) (NPL 13). Warzecha et al. recently cloned RBM35a and RBM35b as epithelia-specific activators of exon 8 inclusion, and renamed them epithelial splicing regulatory proteins 1 and 2 (ESRP1 and ESPR2), respectively (NPL 14). For exon 9 regualtion, Chen et al. found that Tra2beta represses the selection of exon 9 (NPL 15). Baraniak et al. reported that Fox2 represses selection of exon 9 through binding to a UGCAUG sequence in intron 8 (NPL 16). Hovhannisyan et al. found that a hnRNP M binds to ISS-3 and represses inclusion of exon 9 (NPL 17). Mauger et al. showed that hnRNP H and F interact with Fox2 and repress exon 9 inclusion (NPL 18). Also, presence of unknown enhancer is speculated for exon 9 inclusion through ISE (intronic splicing enhancer) in intron 9 (NPL 14).

CITATION LIST

Non Patent Literature

NPL 1: Pan Q, Shai O, Lee L J, Frey B J, Blencowe B J (2008) Deep surveying of alternative splicing complexity in the human transcriptome by high-throughput sequencing. Nat Genet. 40: 1413-1415.

NPL 2: Wang E T, Sandberg R, Luo S, Khrebtukova I, Zhang L, et al. (2008) Alternative isoform regulation in human tissue transcriptomes. Nature 456: 470-476.

NPL 3: Matlin A J, Clark F, Smith C W (2005) Understanding alternative splicing: towards a cellular code. Nat Rev Mol Cell Biol 6: 386-398.

NPL 4: Black D L (2003) Mechanisms of alternative pre-messenger RNA splicing. Annu Rev Biochem 72: 291-336.

NPL 5: Gilbert E, Del Gatto F, Champion-Arnaud P, Gesnel M C, Breathnach R (1993) Control of BEK and K-SAM splice sites in alternative splicing of the fibroblast growth factor receptor 2 pre-mRNA. Mol Cell Biol 13: 5461-5468.

NPL 6: Savagner P, Valles A M, Jouanneau J, Yamada K M, Thiery J P (1994) Alternative splicing in fibroblast growth factor receptor 2 is associated with induced epithelial-mesenchymal transition in rat bladder carcinoma cells. Mol Biol Cell 5: 851-862.

NPL 7: Ornitz D M, Xu J, Colvin J S, McEwen D G, MacArthur C A, et al. (1996) Receptor specificity of the fibroblast growth factor family. J Biol Chem 271: 15292-15297.

NPL 8: Eswarakumar V P, Lax I, Schlessinger J (2005) Cellular signaling by fibroblast growth factor receptors. Cytokine Growth Factor Rev 16: 139-149.

NPL 9: Zhang X, Ibrahimi O A, Olsen S K, Umemori H, Mohammadi M, et al. (2006) Receptor specificity of the fibroblast growth factor family. The complete mammalian FGF family. J Biol Chem 281: 15694-15700.

NPL 10: De Moerlooze L, Spencer-Dene B, Revest J M, Hajihosseini M, Rosewell I, et al. (2000) An important role for the IIIb isoform of fibroblast growth factor receptor 2 (FGFR2) in mesenchymal-epithelial signalling during mouse organogenesis. Development 127: 483-492.

NPL 11: Eswarakumar V P, Monsonego-Ornan E, Pines M, Antonopoulou I, Morriss-Kay G M, et al. (2002) The IIIc alternative of Fgfr2 is a positive regulator of bone formation. Development 129: 3783-3793.

NPL 12: Del Gatto-Konczak F, Olive M, Gesnel M C, Breathnach R (1999) hnRNP A1 recruited to an exon in vivo can function as an exon splicing silencer. Mol Cell Biol 19: 251-260.

NPL 13: Carstens R P, Wagner E J, Garcia-Blanco M A (2000) An intronic splicing silencer causes skipping of the IIIb exon of fibroblast growth factor receptor 2 through involvement of polypyrimidine tract binding protein. Mol Cell Biol 20: 7388-7400.

NPL 14: Warzecha C C, Sato T K, Nabet B, Hogenesch J B, Carstens R P (2009) ESRP1 and ESRP2 are epithelial cell-type-specific regulators of FGFR2 splicing. Mol Cell 33: 591-601.

NPL 15: Chen X, Huang J, Li J, Han Y, Wu K, et al. (2004) Tra2betal regulates P19 neuronal differentiation and the splicing of FGF-2R and GluR-B minigenes. Cell Biol Int 28: 791-799.

NPL 16: Baraniak A P, Chen J R, Garcia-Blanco M A (2006) Fox-2 mediates epithelial cell-specific fibroblast growth factor receptor 2 exon choice. Mol Cell Biol 26: 1209-1222.

NPL 17: Hovhannisyan R H, Carstens R P (2007) Heterogeneous ribonucleoprotein m is a splicing regulatory protein that can enhance or silence splicing of alternatively spliced exons. J Biol Chem 282: 36265-36274.

NPL 18: Mauger D M, Lin C, Garcia-Blanco M A (2008) hnRNP H and hnRNP F complex with Fox2 to silence fibroblast growth factor receptor 2 exon IIIc. Mol Cell Biol 28: 5403-5419.

SUMMARY OF INVENTION

Technical Problem

An object of the present invention is to develop a new alternative splicing reporter system in a mammalian organism and to provide a method for detecting alternative splicing patterns in a mammalian multicellular organism more precisely, a method for identifying efficiently substances and gene regions that affect alternative splicing in a mammalian multicellular organism, and the like by utilizing the alternative splicing reporter system.

Solution to Problem

Since alternative splicing of pre-mRNAs is essential for generating tissue-specific diversity in proteome, elucidating its regulatory mechanism is indispensable to understand developmental process or tissue-specific functions. The present inventors have investigated tissue-specific regulation of mutually exclusive selection of alternative exons using transgenic splicing reporters in nematode, because the present inventors hypothesized that this implies the typical molecular mechanism of alternative splicing. So far, mutually exclusive splicing regulation has been explained by the outcome from the balance of multiple regulators that enhance or repress either of alternative exons discretely. However, this "balance" model is open to questions how to ensure the selection of only one appropriate exon out of several candidates and how to switch them. To answer these questions, the present inventors generated an original bichromatic fluorescent splicing reporter system for mammals using fibroblast growth factor-receptor 2 (FGFR2) gene as model. By using this splicing reporter, the present inventors demonstrated that FGFR2 gene is regulated by the "switch-like" mechanism", in which key regulators modify the ordered splice-site recognition of two mutually exclusive exons, eventually ensure single exon selection and their distinct switching. Also this finding elucidated the evolutionarily conserved "splice code", in which combination of tissue-specific and broadly expressed RNA binding proteins regulate alternative splicing of specific gene in tissue-specific manner. These findings provide the significant cue to understand how a number of spliced genes are regulated in various tissue-specific manners by a limited number of regulators, eventually to understand developmental process or tissue-specific functions.

The present invention is based on the above-mentioned experiences or discoveries by the present inventors, and means for solving the above-mentioned problems are as follows. Specifically, A first method for detecting an alternative splicing of a specific gene in a mammalian multicellular organism of the present invention includes:
(a) introducing into the mammalian multicellular organism a DNA construct such that at least two different reporter genes are inserted into the specific gene which undergoes the alternative splicing, wherein the reporter genes are inserted so that transcripts of the different reporter genes are each fused with each of at least two different mature mRNAs generated by alternative splicing; and
(b) detecting the alternative splicing of the specific gene in the mammalian multicellular organism by the expression of the reporter genes.

A first method for testing whether or not a compound to be tested affects an alternative splicing of a specific gene of the present invention includes:
(a) introducing into a mammalian multicellular organism a DNA construct such that at least two different reporter genes are inserted into the specific gene which undergoes the alternative splicing, wherein the reporter genes are inserted so that transcripts of the different reporter genes are each fused with each of at least two different mature mRNAs generated by the alternative splicing;
(b) allowing the mammalian multicellular organism to contact the compound to be tested;
(c) detecting the alternative splicing of the specific gene in the mammalian multicellular organism by the expression of the reporter genes; and
(d) determining whether or not the expression of the reporter genes detected in the (c) has changed compared to the expression of the reporter genes in a control which is not allowed to contact the compound to be tested.

A first method for identifying a gene region affecting an alternative splicing of a specific gene of the present invention includes:
(a) introducing into a mammalian multicellular organism a DNA construct such that at least two different reporter genes are inserted into the specific gene which undergoes the alternative splicing,
wherein the reporter genes are inserted so that transcripts of the different reporter genes are each fused with each of at least two different mature mRNAs generated by the alternative splicing;
(b) treating the mammalian multicellular organism with a mutagen;
(c) detecting the alternative splicing of the specific gene in the mammalian multicellular organism by the expression of the reporter genes;
(d) selecting an individual in which the expression of the reporter genes detected in the (c) has changed compared to the expression of the reporter genes in a control which is not subjected to the mutagen treatment; and
(e) identifying a mutated gene region in the individual.

A first method for identifying a region in a specific gene affecting an alternative splicing of the specific gene of the present invention includes:
(a) introducing into a mammalian multicellular organism a DNA construct such that at least two different reporter genes are inserted into the specific gene into which a mutation has been introduced and which undergoes the alternative splicing, wherein the reporter genes are inserted so that transcripts of the different reporter genes are each fused with each of at least two different mature mRNAs generated by the alternative splicing;

(b) detecting the alternative splicing of the specific gene in the mammalian multicellular organism by the expression of the reporter genes; and (c) determining whether or not the expression of the reporter genes detected in the (b) has changed compared to the expression of the reporter genes in a control in which a mutation has not been introduced into the specific gene.

A second method for detecting an alternative splicing of a specific gene in a mammalian multicellular organism of the present invention includes:

(a) introducing into the mammalian multicellular organism a combination of DNA constructs, wherein in the DNA construct, a reporter gene is inserted into the specific gene which undergoes the alternative splicing, and the combination of DNA constructs satisfies all of the following conditions (i) to (iv):

(i) reporter genes inserted into each DNA construct are different from each other, (ii) in each DNA construct, the reporter gene is inserted into the specific gene so that a transcript of the reporter gene is fused with a plurality of mature mRNAs generated by the alternative splicing, (iii) a transcript portion of the reporter gene in only one mature mRNA of the plurality of mature mRNAs generated by the alternative splicing from each DNA construct is translated in a correct reading frame, and (iv) only when a specific splicing is selected among alternative splicing patterns, the translation in a correct reading frame is induced in each DNA construct, and the specific splicing which induces the translation in a correct reading frame is different depending on each DNA construct; and (b) detecting the alternative splicing of the specific gene in the mammalian multicellular organism by the expression of the reporter genes.

A second method for testing whether or not a compound to be tested affects an alternative splicing of a specific gene of the present invention includes:

(a) introducing into a mammalian multicellular organism a combination of DNA constructs, wherein in the DNA construct, a reporter gene is inserted into the specific gene which undergoes the alternative splicing, and the combination of DNA constructs satisfies all of the following conditions (i) to (iv):

(i) reporter genes inserted into each DNA construct are different from each other, (ii) in each DNA construct, the reporter gene is inserted into the specific gene so that a transcript of the reporter gene is fused with a plurality of mature mRNAs generated by the alternative splicing, (iii) a transcript portion of the reporter gene in only one mature mRNA of the plurality of mature mRNAs generated by the alternative splicing from each DNA construct is translated in a correct reading frame, and (iv) only when a specific splicing is selected among alternative splicing patterns, the translation in a correct reading frame is induced in each DNA construct, and the specific splicing which induces the translation in a correct reading frame is different depending on each DNA construct;

(b) allowing the mammalian multicellular organism to contact the compound to be tested;

(c) detecting the alternative splicing of the specific gene in the mammalian multicellular organism by the expression of the reporter genes; and (d) determining whether or not the expression of the reporter genes detected in the (c) has changed compared to the expression of the reporter genes in a control which is not allowed to contact the compound to be tested.

A second method for identifying a gene region affecting an alternative splicing of a specific gene of the present invention includes:

(a) introducing into a mammalian multicellular organism a combination of DNA constructs, wherein in the DNA construct, a reporter gene is inserted into the specific gene which undergoes the alternative splicing, and the combination of DNA constructs satisfies all of the following conditions (i) to (iv):

(i) reporter genes inserted into each DNA construct are different from each other, (ii) in each DNA construct, the reporter gene is inserted into the specific gene so that a transcript of the reporter gene is fused with a plurality of mature mRNAs generated by the alternative splicing, (iii) a transcript portion of the reporter gene in only one mature mRNA of the plurality of mature mRNAs generated by the alternative splicing from each DNA construct is translated in a correct reading frame, and (iv) only when a specific splicing is selected among alternative splicing patterns, the translation in a correct reading frame is induced in each DNA construct, and the specific splicing which induces the translation in a correct reading frame is different depending on each DNA construct;

(b) treating the mammalian multicellular organism with a mutagen;

(c) detecting the alternative splicing of the specific gene in the mammalian multicellular organism by the expression of the reporter genes;

(d) selecting an individual in which the expression of the reporter genes detected in the (c) has changed compared to the expression of the reporter genes in a control which is not subjected to the mutagen treatment; and (e) identifying a mutated gene region in the individual.

A second method for identifying a region in a specific gene affecting an alternative splicing of the specific gene of the present invention includes:

(a) introducing into a mammalian multicellular organism a combination of DNA constructs, wherein in the DNA construct, a reporter gene is inserted into the specific gene into which a mutation has been introduced and which undergoes the alternative splicing, and the combination of DNA constructs satisfies all of the following conditions (i) to (iv):

(i) reporter genes inserted into each DNA construct are different from each other, (ii) in each DNA construct, the reporter gene is inserted into the specific gene so that a transcript of the reporter gene is fused with a plurality of mature mRNAs generated by the alternative splicing, (iii) a transcript portion of the reporter gene in only one mature mRNA of the plurality of mature mRNAs generated by the alternative splicing from each DNA construct is translated in a correct reading frame, and (iv) when a specific splicing is selected among alternative splicing patterns, the translation in a correct reading frame is induced in each DNA construct, and the specific splicing which induces the translation in a correct reading frame is different depending on each DNA construct;

(b) detecting the alternative splicing of the specific gene in the mammalian multicellular organism by the expression of the reporter genes; and (c) determining whether or not the expression of the reporter genes detected in the (b) has changed compared to the expression of the reporter genes in a control in which a mutation has not been introduced into the specific gene.

The present invention can solve conventional problems, can attain the above-mentioned object, and can provide a method for detecting alternative splicing patterns in a mammalian multicellular organism, a method for identifying efficiently substances and gene regions that affect alternative splicing in a mammalian multicellular organism, and the like.

BRIEF DESCRIPTION OF DRAWINGS

FIGS. 3A-3B show construction of an 'Expression' clone by '2-fragment' recombination reaction utilizing MULTISITE GATEWAY® vector construction system. (A) Cloning DNA fragments of interest in 'Entry' vectors by 'BP' reaction. attB-flanked PCR products and two MULTISITE GATEWAY® 'Donor' vectors are used in separate 'BP' recombination reactions to generate two 'Entry' clones, one with attL1 and attR5 sites, and the other with attL5 and attL2 sites. att sites are not palindromic and have an orientation. The direction of the arrowhead designates the orientation of each att site in relation to the insert; the attB5 or attP5 site is designated with "r" when the arrowhead does not point towards the insert. [It appears as attB5r or attP5r in the left panel.] (B) Construction of an 'Expression' clone by 'LR' reaction. The two 'Entry' clones and a 'Destination' vector are used together in ' LR' re-combination reaction to create an 'Expression' clone containing the two DNA fragments.

FIGS. 6A-6D show the construction of FGFR2 splicing reporter vector and their expression patterns. (A) Scheme of FGFR2 splicing reporter vector. The genomic fragment of mouse FGFR2 including exon 7 through 10 was amplified and introduced into the reporter vector containing a CAGGS promoter and RFP-EGFP with different reading frames. Modified glutathione-S-transferase gene (indicated as "G") was inserted in front of the exon 7 in-frame. A schematic representation of the mRNA derived from the reporter under the alternative splicing regulation is also shown; the numbers indicate the reading frames. (B) Expression pattern of splicing reporter in vitro. The reporter vector was introduced into two rat prostate cancer cell lines AT-3 and DT-3, which have different cell-type specificities. Scale=200 micrometer. (C) Expression pattern of splicing reporter in vivo. Fluorescence images of transgenic reporter mouse embryos at E14.5. Tg(+) is an embryo carrying the reporter vector, and Tg(−) is one of its litter-mate lacking the vector. Arrowheads in Tg(+) indicate EGFP signals with the patterns of whiskers (upper arrowhead) and the edge of a limb (lower arrowhead), both of which are magnified and indicated by white rectangles in the upper left-hand and lower right-hand corners, respectively (scale=1 mm). (D) Sections from transgenic reporter mouse embryos at E16.5. Each panel shows sections from the indicated tissues, the upper one from Tg(+) and the lower from Tg(−). Portions expressing the EGFP signal are indicated by white arrows (scale=100 micrometer).

FIGS. 7A-7B show the unbalanced sequence of 3' splice sites is essential for mutually exclusive exon selection. (A) Scheme for 3' splice site mutation on exons 8 and 9. The sequence of the weak 3' splice site of exon 8 is TGTTCTAGca (SEQ ID NO: 40). The sequence of the strong 3' splice site of exon 9 is TTTTCTAGgc (SEQ ID NO: 41). Uppercase letter is intron and lowercase is exon sequence. White characters on a black background indicate mismatches from the conserved consensus sequence in the 3' splice site and poly-pyrimidine moiety, and underline indicate mutated sequence. The gray arrows with "primer" represent the positions amplified in RT-PCR. (B) RT-PCR from AT-3 and DT-3 cells trans fected the indicated vectors. Splice products were digested with EcoRV, which uniquely cuts the PCR product containing exon 9. Each band was identified and indicated with the scheme of splice products. Arrowheads indicate nonspecific PCR products, which was confirmed by sequencing. The asterisk indicates the splice product came from double inclusion of exon 8 and exon 9. The bar graph shows the amount of each splicing product, and is based on calculations from three independent experiments; the mean value for each splice product is show in the respective column with an error bar showing the SD (standard error).

FIGS. 9A-9C show the identification of silencing elements for exon 9 recognition. (A) Scheme of cis-mutation experiment on UGCAUG and ISE/ISS-3 which is located upstream of exon 9. UGCAUGCAUG (SEQ ID NO: 42) was substituted for UACGUACGUG (SEQ ID NO: 43) to disrupt the binding to the RNA-binding protein of Fox. White characters on a black background indicated mutated sequences or deletions. (B) RT-PCR from AT-3 cell into which the indicated vectors were introduced. The bar graph shows the amount of each splicing product, and is based on calculations from three independent experiments; the mean value for each splice product is show in the respective column, with an error bar showing the SD (standard error). (C) RT-PCR from AT-3 and DT-3 cells showing amplified endogenous FGFR2, Fox1, Fox2, ESRPI, and ESRP2. The arrowhead in ESRPI corresponds to two splice isoforms which was confirmed by sequencing.

FIGS. 10A-10C show the Foxs and ESRPs which promote switching to exon 8 through repressing exon 9. (A) RT-PCR from HeLa cell transfected the wild-type reporter and indicated cDNA expression vectors with or without Fox2 siRNA. The bar graph shows the amount of each splicing product. (B) Fluorescent microscopy image of HeLa cell transfected the wild-type reporter with indicated cDNA expression vectors (scale bar=200 micrometer). (C) Result of an in vitro splice site recognition assay. The scheme for exon 9 RNA probe shows the position of UGCAUG and ISE/ISS-3. The asterisk shows the probe crosslinked with U1, which binds to the cryptic 5' splice site inside exon 9.

FIGS. 12A-12B show the model for tissue-specific splicing regulation of FGFR2 gene. (A) "The Knight's Fork" regulation model: In non-epithelial or mesenchymal tissues, exon 9 is chosen as "primary" exon due to its stronger 3' splice site than exon 8 ("default" selection to choose "primary" exon). In epithelial tissues, "key regulators" repress exon 9 utilizing its 3' splice site dependency for exon recognition and cause switch to "secondary" exons ("alternative" selection to choose "secondary" exon). A small number of "key regulators" can control two mutually exclusive exons through modifying ordered splice-site recognitions in a tissue-specific manner, resembling the way that a chess piece can simultaneously attack a rook and check the king. (B) In nematode, mutually exclusive splicing of the worm FGFR homologue gene of egl-15 is regulated by the cooperation of broadly expressed Fox-1/ASD-1 family and the muscle-specific RNA binding motif protein (RBMs) of SUP-12 (a worm homologue of mRBM24), which act together to repress inclusion of alternative exon 5B to promote muscle-specific expression of exon 5A. In the case of mammalian FGFR2, the Fox family cooperates with the tissue-specific factor ESRPs (RBM35a and b) to repress alternative inclusion of exon 9 and to promote epithelial tissue-specific expression of exon 8.

DESCRIPTION OF EMBODIMENTS

Figure 1:
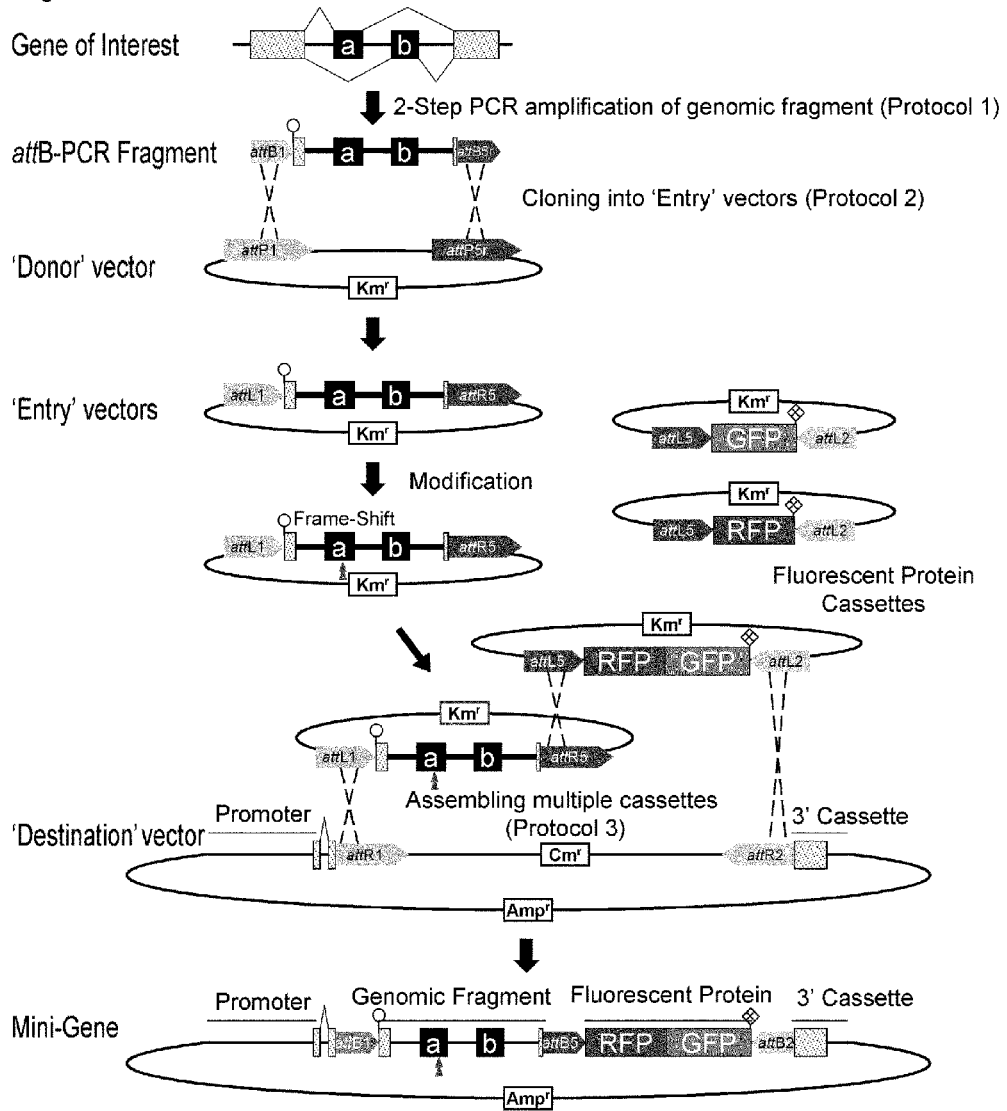
FIG. 1 shows single cell detection of splicing events with fluorescent splicing reporters. Overview: Construction of fluorescent alternative splicing reporter mini-genes.

First and Second Alternative Splicing Reporter Systems

In a first aspect, the present invention relates to an alternative splicing reporter system in a mammalian multicellular organism using a DNA construct in which at least two different reporter genes are inserted into a specific gene that undergoes alternative splicing (for example, see FIGS. 2C and 2D). In a second aspect, the present invention relates to an alternative splicing reporter system in a mammalian multicellular organism using a combination of DNA constructs (a combination of at least two different DNA constructs) in which DNA construct a reporter gene is inserted into a specific gene that undergoes alternative splicing (for example, see FIGS. 2A and 2B).

Both of the first and second systems allows the detection of alternative splicing patterns of a specific gene in vivo (or in vitro, or ex vivo) in mammalian multicellular organisms by introducing a DNA construct (or combination of DNA constructs), into which at least two different reporter genes are inserted in total, into a mammalian multicellular organism. The first and second systems each can be suitably utilized for "(1) a method for detecting alternative splicing of a specific gene in a mammalian multicellular organism", "(2) a method for testing whether or not a compound to be tested affects alternative splicing of a specific gene", "(3) a method for identifying a gene region affecting alternative splicing of a specific gene", and "(4) a method for identifying a region in a specific gene affecting alternative splicing of the specific gene" of the present invention, which will be described later.

It was difficult to precisely predict tissue-specific and/or stage-specific alternative splicing patterns in vivo from the results of conventional in vitro studies on alternative splicing using cultured cells, etc. Use of the first and second systems enables direct and accurate detection of tissue-specific and/or stage-specific alternative splicing patterns in vivo in mammalian multicellular organisms. Thus, it is considered that the first and second systems can become powerful experimental tools for elucidating mechanisms of alternative splicing in mammalian multicellular organisms.

<Multicellular Organism>

In the first and second systems, the "mammalian multicellular organism" is not particularly limited and can be appropriately selected depending on the application as long as it consists of many cells and has mechanisms of alternative splicing, including, for example, mouse, and rat. Namely, the mammalian used in the present invention is preferably non-human animal such as rodent animals (i.e. mouse, rat, etc.). The "mammalian multicellular organism" of the present invention includes the cell derived from mammalian animal. Namely, present invention encompasses the method using the cells derived from mammalian animals.

<Specific Gene Undergoing Alternative Splicing>

The "specific gene that undergoes alternative splicing" (hereinafter, may be simply referred to as "specific gene") in the first and second systems is not particularly limited and can be appropriately selected depending on the application as long as it is a gene of mammalian multicellular organisms and can produce multiple isoforms of mature mRNAs consisting of different combinations of exons as a result of alternative splicing.

Here, the "alternative splicing" refers to a phenomenon in which multiple isoforms of mature mRNAs consisting of different combinations of exons are produced in cells by varying patterns of splicing when introns are removed from pre-mRNAs by RNA splicing. This phenomenon enables organisms having alternative splicing machinery to produce different proteins from a single gene.

<Reporter Gene>

In the first and second systems, the "reporter gene" is not particularly limited and can be appropriately selected depending on the application. Examples of the reporter gene include fluorescent protein genes such as a green fluorescent protein (GFP) and a red fluorescent protein (RFP), enzyme genes that catalyze chromogenic reaction or color-developing reaction, or luminous reaction, and the like. In the first and second systems, at least two different reporter genes are used in total. The combination thereof is not particularly limited and can be appropriately selected depending on the application as long as their expressions can be distinguished from each other based on the difference of fluorescence or developed color. For example, a combination of a green fluorescent protein (GFP) and a red fluorescent protein (RFP), and the like can be suitably used.

<DNA Construct>

—DNA Construct of First System—

The DNA construct in the first system is one in which at least two different reporter genes are inserted into a specific gene that undergoes alternative splicing. The at least two different reporter genes are inserted into the specific gene such that transcripts of the at least two different reporter genes are each fused with each of at least two different mature mRNAs generated by alternative splicing of the specific gene.

Preferably, the at least two different reporter genes are each connected to a different exon which is included in at least two different transcripts (mature mRNAs) generated by alternative splicing of the specific gene (for example, see FIGS. 2C and 2D). Each reporter gene may be connected upstream (5' side) of each of the exons, or may be connected downstream (3' side) thereof; however, each reporter gene is required to be connected to each of the exons such that each reporter gene is translated in a correct reading frame only when each exon, to which each reporter gene is connected, is translated in a correct reading frame. Such structure of the DNA construct allows to check whether each exon, to which each reporter gene is connected, has been translated in a correct reading frame when the expression of each reporter gene is detected. That is, analysis of respective expression patterns of the at least two different reporter genes makes it possible to check alternative splicing patterns of the specific gene comprehensively.

—DNA Construct of Second System—

On the other hand, the DNA construct in the second system is one in which a reporter gene is inserted into a specific gene that undergoes alternative splicing. The second system is characterized in that a combination of such DNA constructs (combination of at least two different DNA constructs) is used. Here, the combination of DNA constructs satisfies all conditions of the following (i) to (iv):

(i) reporter genes inserted into each DNA construct are different from each other;
(ii) in each DNA construct, the reporter gene is inserted into the specific gene so that a transcript of the reporter gene is fused with a plurality of mature mRNAs generated by the alternative splicing;
(iii) a transcript portion of the reporter gene in only one mature mRNA of the plurality of mature mRNAs generated by the alternative splicing from each DNA construct is translated in a correct reading frame; and
(iv) only when a specific splicing is selected among alternative splicing patterns, the translation in a correct reading frame is induced in each DNA construct, and the specific splicing which induces the translation in a correct reading frame is different depending on each DNA construct.

Preferably, each reporter gene in each DNA construct is connected to one of different exons which are included in at least two different transcripts (mature mRNAs) generated by alternative splicing of the specific gene (for example, see FIGS. 2A and 2B). Each reporter gene may be connected upstream (5' side) of each of the exons, or may be connected downstream (3' side) thereof; however, each reporter gene is required to be connected to each of the exons such that each reporter gene is translated in a correct reading frame only when each exon, to which each reporter gene is connected, is translated in a correct reading frame. Use of combination of DNA constructs constructed in such a way allows to check whether each exon, to which each reporter gene is connected, has been translated in a correct reading frame when the expression of each reporter gene is detected. That is, analysis of each expression pattern of each reporter gene in the combination of DNA constructs makes it possible to check alternative splicing patterns of the specific gene comprehensively.

In the DNA constructs of the first and second systems, the specific gene and the reporter gene are preferably linked downstream of a promoter so that they can be expressed in a mammalian multicellular organisms. The promoter is not particularly limited and can be appropriately selected depending on the application. Examples thereof include tissue-specific promoters such as the CAGGS promoter.

The DNA construct can be constructed by any method without limitation, and known techniques can be appropriately utilized. For example, the DNA construct can be constructed by integrating a reporter cassette, in which cDNA of the reporter gene is inserted into the genomic DNA fragment of the specific gene, into an expression vector that includes a desired promoter.

For example, DNA construct used for the present invention can be made by the method shown in FIG. 1 or 3.

Hereinafter, various methods according to the present invention utilizing the first and second alternative splicing reporter systems will be described.

((1) Method for Detecting Alternative Splicing of a Specific Gene in a Mammalian Multicellular Organism)

The method for detecting alternative splicing of a specific gene in a mammalian multicellular organism of the present invention comprises the steps of (a) introducing into the mammalian multicellular organism a DNA construct in the first system or a combination of DNA constructs in the second system (each contain the specific gene and the reporter gene), and (b) detecting the alternative splicing of the specific gene in the mammalian multicellular organism by detecting the expression of the reporter genes.

<Step (a)>

In the step (a), a DNA construct in the first system or a combination of DNA constructs in the second system is introduced into the mammalian multicellular organism to generate a transgenic mammalian multicellular organism. The DNA construct or the combination of DNA constructs can be introduced into the mammalian multicellular organisms by any method without limitation. For example, conventionally known techniques of gene transfer such as microinjection can be appropriately utilized.

<Step (b)>

In the step (b), alternative splicing of the specific gene in the mammalian multicellular organism is detected by detecting the expression of the reporter genes. Expression of the reporter genes can be detected by any method without limitation, and known detection methods can be appropriately utilized depending on the type of reporter gene. For example, when fluorescent proteins are used as the reporter, the expression can be detected using a fluorescence microscope or fluorescence-assisted sorter.

The DNA construct or the combination of DNA constructs contains at least two different reporter genes in total, and as described above, these reporter genes are inserted into the specific gene so that transcripts of the different reporter genes are fused with each of multiple mature mRNAs generated by alternative splicing. Therefore, by detecting the expression of these at least two different reporter genes in step (b), which form of mature mRNA is produced by alternative splicing can be checked; in other words, detection of alternative splicing patterns of the specific gene in vivo in mammalian multicellular organisms is made possible. The method for detecting alternative splicing of a specific gene in a mammalian multicellular organism also enables to detect tissue-specific and/or developmental stage-specific alternative splicing patterns in detail by changing the type of the promoter that is included in the DNA construct or the combination of DNA constructs, or changing developmental stage of the mammalian multicellular organism used.

((2) Method for Testing Whether or not a Compound to be Tested Affects Alternative Splicing of a Specific Gene)

The method for testing whether or not a compound to be tested affects alternative splicing of a specific gene of the present invention comprises the steps of (a) introducing into the mammalian multicellular organism a DNA construct in the first system or a combination of DNA constructs in the second system (each contain the specific gene and the reporter gene), (b) allowing the mammalian multicellular organism to contact the compound to be tested, (c) detecting the alternative splicing of the specific gene in the mammalian multicellular organism by detecting the expression of the reporter genes; and (d) determining whether or not the expression of the reporter genes detected in the (c) has changed compared to the expression of the reporter genes in a control which is not allowed to contact the compound to be tested.

<Step (a) and Step (c)>

The step (a) and the step (c) can be performed in the same manner as the step (a) and the step (b) in the "method for detecting alternative splicing of a specific gene in a mammalian multicellular organism" mentioned above, respectively.

<Step (b)>

In the step (b), the mammalian multicellular organism, into which the DNA construct or the combination of DNA constructs is introduced in the step (a), is allowed to contact a compound to be tested. The "compound to be tested" is not particularly limited and can be appropriately selected depending on the application from substances which one wants to test for whether or not they affect alternative splicing of the specific gene. Examples thereof include purified proteins, partially purified proteins, peptides, nonpeptidic compounds, artificially synthesized compounds, naturally-occurring compounds, and the like. In addition, the method for allowing the mammalian multicellular organism to contact the "compound to be tested" is not particularly limited; examples thereof include a method in which the "compound to be tested" is injected by microinjection, a method in which the "compound to be tested" is fed to the mammalian multicellular organism by mixing it in a food, and the like.

<Step (d)>

In the step (d), whether or not the expression of the reporter genes detected in the (c) has changed compared to the expression of the reporter genes in a control which is not allowed to contact the compound to be tested is determined. The change of the expression of the reporter genes is not particularly limited; examples thereof include replacement of the expression of one reporter gene with that of the other reporter gene, decrease or increase of the expression level of one reporter gene, and the like. If in step (d) it is determined that the expression of the reporter genes detected in step (c) has changed compared to the expression of the reporter genes in a control which is not allowed to contact the compound to be tested, it can be evaluated that the compound to be tested affects alternative splicing of the specific gene.

((3) Method for Identifying a Gene Region Affecting Alternative Splicing of a Specific Gene)

The method for identifying a gene region affecting alternative splicing of a specific gene of the present invention comprises the steps of (a) introducing into a mammalian multicellular organism a DNA construct in the first system, or a combination of DNA constructs in the second system (each contain the specific gene and the reporter gene), (b) treating the mammalian multicellular organism with a mutagen, (c) detecting the alternative splicing of the specific gene in the mammalian multicellular organism by detecting the expression of the reporter genes, (d) selecting an individual in which the expression of the reporter genes detected in step (c) has changed compared to the expression of the reporter genes in a control which is not subjected to the mutagen treatment, and (e) identifying a mutated gene region in the individual. The method allows the identification of trans-acting factors that affect alternative splicing of the specific gene.

<Step (a) and Step (c)>

The step (a) and the step (c) can be performed in the same manner as the step (a) and the step (b) in the "method for detecting alternative splicing of a specific gene in a mammalian multicellular organism" mentioned above, respectively.

<Step (b)>

In the step (b), the mammalian multicellular organism, into which the DNA construct or the combination of DNA constructs has been introduced in the step (a), is treated with a mutagen. The mutagen treatment of mammalian multicellular organisms is not particularly limited and can be performed by known methods. Examples thereof include treatment with ethyl methanesulfonate (EMS), treatment with ultraviolet light, and the like.

<Step (d)>

In the step (d), an individual, in which the expression of the reporter genes detected in step (c) has changed compared to the expression of the reporter genes in a control which is not subjected to the mutagen treatment, is selected. The change of the expression of the reporter genes is not particularly limited; examples thereof include replacement of the expression of one reporter gene with that of the other reporter gene, decrease or increase of the expression level of reporter gene, and the like.

<Step (e)>

In the step (e), a mutated gene region in the individual, in which the expression of the reporter genes has changed, is identified. The method for identifying the gene region is not particularly limited and conventionally known chromosome mapping and the like can be appropriately utilized.

((4) Method for Identifying a Region in a Specific Gene Affecting Alternative Splicing of the Specific Gene)

The method for identifying a region in a specific gene affecting alternative splicing of the specific gene of the present invention comprises steps of (a) introducing into the mammalian multicellular organism a DNA construct in the first system, or a combination of DNA constructs in the second system (each contain the specific gene and the reporter gene), wherein in the DNA construct or the combination of DNA constructs, a mutation has been introduced into the specific gene, (b) detecting the alternative splicing of the specific gene in the mammalian multicellular organism by detecting the expression of the reporter genes, and (c) determining whether or not the expression of the reporter genes detected in the (b) has changed compared to the expression of the reporter genes in a control in which a mutation has not been introduced into the specific gene. The method allows the identification of cis-acting DNA sequences that affect alternative splicing of the specific gene.

<Step (a)>

In the step (a), a DNA construct in the first system, or a combination of DNA constructs in the second system (each contain the specific gene and the reporter gene) is introduced into the mammalian multicellular organism, wherein in the DNA construct or the combination of DNA constructs, a mutation has been introduced into the specific gene. The method for introducing a mutation into the specific gene is not particularly limited and deletion, insertion, substitution, and the like can be appropriately induced in the specific gene by utilizing conventionally known techniques. In addition, the region in the specific gene into which a mutation is introduced is not particularly limited, and the region, for which one wants to evaluate whether the region affects alternative splicing of the specific gene, can be appropriately selected.

<Step (b)>

The step (b) can be performed in the same manner as the step (b) in the "method for detecting alternative splicing of a specific gene in a mammalian multicellular organism" mentioned above.

<Step (c)>

In the step (c), whether or not the expression of the reporter genes detected in the (b) has changed compared to the expression of the reporter genes in a control in which a mutation has not been introduced into the specific gene is determined. The change of the expression of the reporter genes is not particularly limited; examples thereof include replacement of the expression of one reporter gene with that of the other reporter gene, decrease or increase of the expression level of reporter gene, and the like. If it is determined that the expression of the reporter genes detected in the (b) has changed compared to the expression of the reporter genes in a control in which a mutation has not been introduced into the specific gene, the region in the specific gene into which a mutation is introduced can be identified as a region that affects alternative splicing of the specific gene.

The methods of the present invention: "(1) a method for detecting alternative splicing of a specific gene in a mammalian multicellular organism", "(2) a method for testing whether or not a compound to be tested affects alternative splicing of a specific gene", "(3) a method for identifying a gene region affecting alternative splicing of a specific gene", and "(4) a method for identifying a region in a specific gene affecting alternative splicing of the specific gene, which utilize the first and second alternative splicing reporter systems developed by the present inventors, can be a very useful way for the comprehensive study of regulation mechanisms of alternative splicing in mammalian multicellular organisms.

The present invention relates to a method for constructing fluorescent alternative splicing reporter mini-genes.

In a preferable embodiment, the instant application presents a method for preparing a DNA vector for visualizing an alternative splicing pattern, the method comprising:

(1) preparing a DNA construct of an amplified DNA region having exons a and b contained in a gene of interest;
(2) adding attB to both ends of the DNA construct;
(3) obtaining a recombinant of the DNA construct of (2) above and a donor vector having a gene for selection and tandemly arranged attP;
(4) introducing a frame-shift mutation into exon a on the DNA construct of (3) above;
(5) obtaining recombinants of (i) to (iii) below:
  (i) the DNA construct of (4) above
  (ii) a DNA vector comprising a gene for selection and a DNA having attL arranged in a direction opposing to each other at both ends of a DNA which has a structure of two kinds of reporter genes being ligated
  (iii) a DNA vector comprising a 3' cassette DNA, a promoter, and a DNA having attR arranged in a direction opposing to each other at both ends of a DNA having a gene for selection.

In the embodiment, the gene of interest is not particularly limited and can be FGFR2 gene. For example, the exons a and b are exon 8 and 9 of FGFR2 gene. The reporter gene is not limited and can be a gene encoding a fluorescent protein.

In a preferable embodiment, the fluorescent alternative splicing reporter mini-genes can be constructed by the method set forth in FIG. 1 or 3.

2. Theoretical Background 2.1. Visualization of Alternative Splicing Patterns with Multiple Fluorescent Proteins To clarify the regulatory mechanisms of alternative splicing in living cells, reporter mini-gene constructs containing multiple exons and introns have often been used. Splicing patterns of the mini-gene-derived mRNAs have usually been quantitatively analyzed with the ratio of reverse transcription (RT)-polymerase chain reaction (PCR) products after extracting total RNAs from transfected cells. The laborious multiple steps in analyzing the splicing patterns often caused deviation in the results and prevented high-throughput analysis of alternative splicing.

The Utilization of fluorescent alternative splicing reporters expressing fluorescent proteins has changed the situation. At initial stages, mono-chromatic, or single-color, fluorescent reporters were used as an indicator of splicing events in cultured cells. The mono-chromatic reporter mini-genes were designed to monitor proper splicing or skipping of alternative exons, and were utilized for isolation of mutant cell lines defective in the regulation of alternative splicing (Sheives, P. and Lynch, K. W. (2002). RNA 8, 1473-1481), functional screening for splicing regulatory elements (Wang, Z. et al., (2004). Cell 119, 831-845), and screening for small chemical compounds that altered splicing patterns (Levinson, N. et al., (2006). RNA 12, 925-930). The advantage of the mono-chromatic reporters is the simplicity of their structure. However, the readout of the mono-chromatic reporters may be affected by influence on gene expression such as transcription and translation.

Multi-chromatic alternative splicing reporters have overcome most of the caveats of the mono-chromatic reporters. The multi-chromatic reporter mini-genes were designed so that expression of each fluorescent protein represents a certain splicing event. The advantage of multi-chromatic fluorescent reporters is that the ratio of the expressed fluorescent proteins reflects the ratio of the mRNA isoforms, or one of the fluorescent proteins acts as an internal control of the expression level, in individual cells. The multi-chromatic reporters are therefore suitable for visualization of alternative splicing patterns in multi-cellular organisms.

The multi-chromatic reporter mini-genes can further be classified into two types, the multi- and the single-construct types. The former consists of multiple mini-genes each of which encodes a single fluorescent protein, while the latter contains two fluorescent protein cDNAs in a single mini-gene construct. Multi-construct reporters have been utilized to search for trans factors and cis-elements by flow cytometry of cultured cells (Newman, E. A. et al., (2006). RNA 12, 1129-1141), and to visualize developmentally regulated alternative splicing and further genetic analysis in *C. elegans* (Ohno, G. et al., (2008). Genes Dev 22, 360-374). A remarkable feature of the single-construct bi-chromatic reporters is that the two alternative mRNA isoforms, each of which encodes a single fluorescent protein, are generated from a common pre-mRNA in a mutually exclusive manner. The single-construct reporters are therefore sensitive to subtle changes in the alternative splicing patterns. The reporters have been utilized for analyzing regulatory factors (Orengo, J. P. et al., (2006). Nucleic Acids Res 34, e148), high-throughput screening for chemical compounds modifying the splicing regulation (Stoilov, P. et al., (2008). Proc Natl Acad Sci USA 105, 11218-11223), and for visualization of cell-type-specific alternative splicing in *C. elegans* (Kuroyanagi, H. et al., (2006). Nat Methods 3, 909-915) and mouse.

2.2. Designing Fluorescent Reporter Mini-Genes to Monitor Splicing Patterns

Here the present inventors show typical structures of multi-chromatic alternative splicing reporter mini-genes (FIG. 2) which the present inventors constructed as described in Examples and explain how expression of each fluorescent protein reports a specific alternative splicing event. Please notice that the reporter mini-genes described in this specification are just a few examples of possible alternative splicing reporters. Each reporter can be flexibly designed depending on alternative splicing events of interest to be visualized. An ideal mini-gene should be designed so that expression of a specific fluorescent protein unambiguously indicates a specific mRNA isoform or a specific alternative splicing event (Kuroyanagi, H. et al., (in press). Visualization and genetic analysis of alternative splicing regulation in vivo using fluorescence reporters in transgenic *Caenorhabditis elegans*. Nat. Protoc.).

Figure 2:
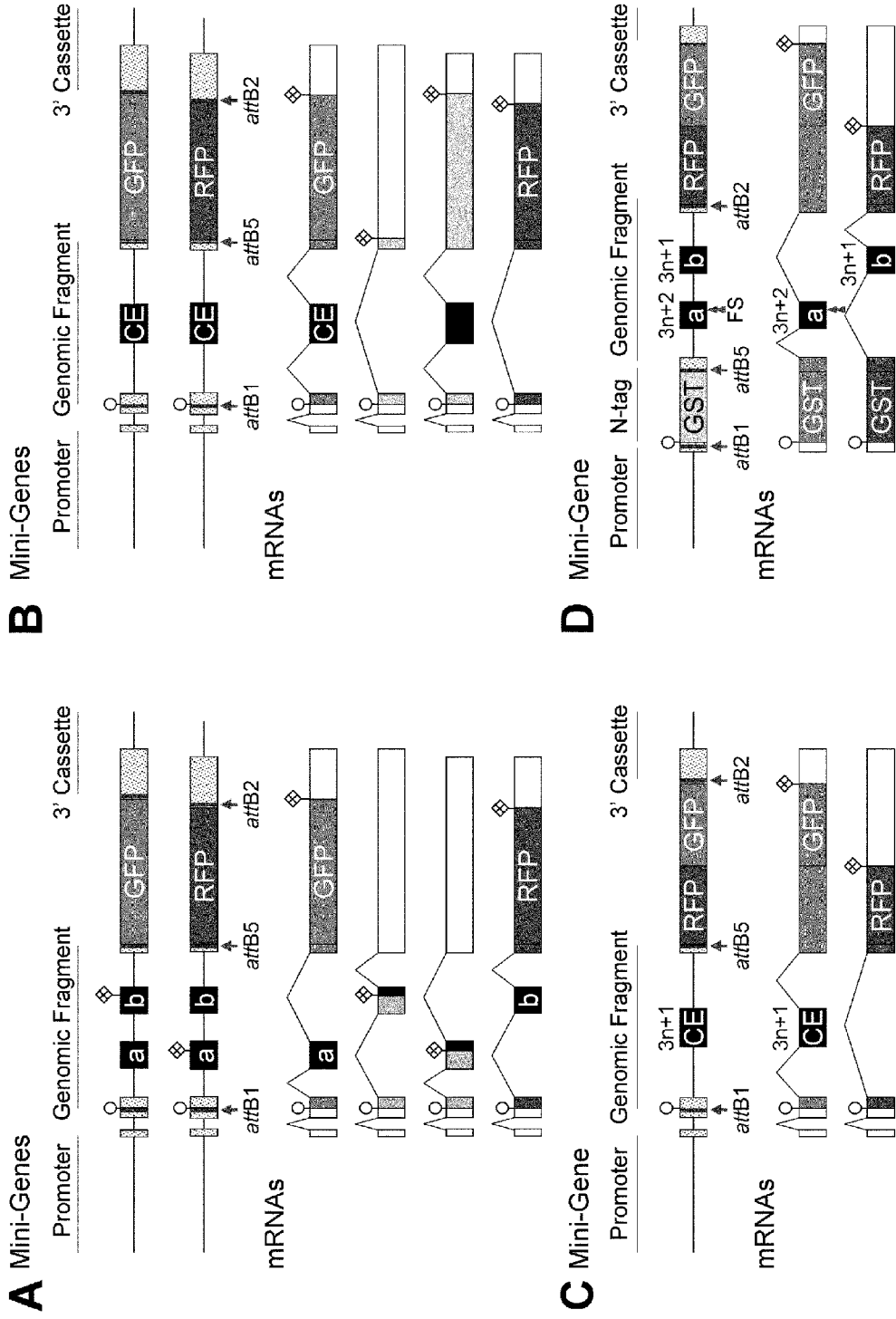
FIGS. 2A-2D show schematic structure of fluorescent reporter mini-genes and expected mRNAs. (A, B) Two-construct fluorescent alternative splicing Cloning reporter mini-genes for mutually exclusive exons (A) and a cassette exon (B). (C, D) Single-construct fluorescent alternative splicing Cloning reporter mini-genes for a cassette exon (C) and mutually exclusive exons (D). Boxes indicate exons. CE, cassette exon. Alternative exons to be analyzed are in black. GFP, RFP and GST cDNAs are indicated in gray. Open circles, diamonds and double arrowheads indicate artificial translation initiation codons, termination codons and artificial frameshifts, respectively. attB sites are indicated with arrows. Open reading frames of expected mRNAs are colored.

As described above, the mini-genes in FIG. 2 can be divided into the multi-construct type (FIG. 2A, B) and the single-construct type (FIG. 2C, D). The choice of the reporter type depends on organisms and the method of mini-gene transfer. Transgenic worms generated by a standard microinjection method carry hundreds of copies of plasmid DNAs as an extra-chromosomal array (Mello, C. C. et al., (1991). EMBO J. 10, 3959-3970) and, therefore, it is generally assumed that injecting a mixture of several different mini-genes with the same vector backbone results in proportional incorporation of all the constructs in the extra-chromosomal array. One of the advantages of the multi-construct reporters is that the number of co-transferred mini-genes can be increased to more than two as described in section 4. For situations where the copy number of transferred mini-genes is small or variable, single-construct reporters might be preferable.

FIG. 2A shows schematic structure of a pair of reporter mini-genes for mutually exclusive exons. A genomic fragment of interest, from the upstream constitutive exon through the downstream constitutive exon, is placed downstream of a common promoter and a constitutive intron, followed by a cDNA for either of two fluorescent proteins and a 3' cassette. An in-frame translation initiation codon is artificially introduced at the 5' end of the genomic fragment. A termination codon is artificially introduced in one of the two alternative exons in each construct. From the mini-genes shown in FIG. 2A, a GFP-fusion protein is produced from an mRNA isoform in which exon a alone is included and an RFP-fusion protein is produced from an mRNA isoform in which exon b alone is selected.

FIG. 2B shows schematic structures of a pair of reporter mini-genes to monitor inclusion and skipping of a cassette exon. The order and composition of the fragment cassettes are as those in FIG. 2A. In the case shown in FIG. 2B, the length of the cassette exon is not a multiple of three bases and therefore inclusion of the cassette exon changes the reading frame of the downstream exon. The GFP cDNA is connected in frame when the cassette exon is included and the RFP cDNA is connected in frame when the cassette exon is excluded.

FIGS. 2C and 2D show schematic structures of single-construct bi-chromatic reporters. These constructs rely on an unusual feature of some fluorescent protein cDNAs in which an alternate reading frame lacks a termination codon (Orengo, J. P. et al., (2006). Nucleic Acids Res 34, e148). In the cases shown in FIGS. 2C and 2D, the RFP and GFP cDNAs are connected in a different reading frame so that translation of the alternate frame of RFP cDNA leads to generation of a fluorescent protein from GFP cDNA. When a fluorescent protein is generated from RFP cDNA, translation will be ceased at its own termination codon. The mini-gene shown in FIG. 2C is for monitoring inclusion and skipping of a cassette exon. GFP cDNA is in frame when the cassette exon is included and RFP cDNA is in frame when the cassette exon is excluded. The mini-gene shown in FIG. 2D is for monitoring the selection of mutually exclusive exons. In this case, one nucleotide is inserted into exon a to cause a frame-shift when this exon is selected. Glutathione S-transferase (GST) of *E. coli* is used as an N-terminal tag for expression of the fusion proteins. The GFP-fusion protein is produced when exon a alone is included and RFP-fusion protein is produced when exon b alone is selected. Neither of the fluorescent proteins is produced when both exons are included or skipped.

2.3. Constructing Fluorescent Reporter Mini-Genes

The present inventors construct fluorescent alternative splicing reporter mini-genes by site-specific recombination utilizing MULTISITE GATEWAY® vector construction system (Invitrogen). Major advantage of homologous recombination in mini-gene construction is that 'Expression' vectors with a variety of structures, as described above, can be easily and rapidly constructed by assembling modular DNA fragments cloned in 'Entry' and 'Destination' vectors. In this section, the present inventors focus on practical use of the MULTISITE GATEWAY® vector construction system and other aspects to be considered in designing fluorescent reporter mini-genes.

23.1. MULTISITE GATEWAY® Vector Construction System

The MULTISITE GATEWAY® vector construction system uses site-specific recombinational cloning to allow simultaneous cloning of two, three or four separate DNA fragments of interest in a defined order and orientation. FIG. 3 schematically illustrates construction of an 'Expression' clone by performing a '2-fragment' recombination reaction. Genomic DNA fragments of interest are cloned in 'Entry' vectors (FIG. 3A) and the fragments are assembled between homologous recombination sites of the 'Destination' vectors (FIG. 3B). A key feature of the MULTISITE GATEWAY® vector construction system is that five sets of modified att sites have an orientation and demonstrate the specificity of homologous recombination as in the standard Gateway system: for example, attB1 site reacts only with attP1 site, but not other attP sites, to generate attL1 and attR1 sites in 'BP' reaction (FIG. 3A), and attL5 site reacts only with attR5 site, but not other attR sites, to generate attB5 and attP5 sites in 'LR' reaction (FIG. 3B). For more details about the MULTISITE GATEWAY® vector construction system and '3-fragment' and '4-fragment' recombination reactions, please refer to the provider's website.

All the att sites in our reporter mini-genes, or 'Expression' clones, are attB sites and reside within exons (FIGS. 2 and 3). The attB sequences (21 to 25 base pairs) are the shortest stretches among all att sites. The present inventors have not experienced cryptic splicing within the attB sequences in *C. elegans* or mammalian cells. It is recommended to use a fixed reading frame in the attB sequences and the present inventors usually do so (see section 3). As attB1, attB5 and attB2 sequences lack ATG and a termination codon in any frames, they can theoretically be used in any frames.

2.3.2. Other Aspects to be Considered in Mini-Gene Construction mRNAs with premature termination (nonsense) codons (PTCs) are selectively degraded by a quality-control mechanism called nonsense-mediated mRNA decay (NMD). In mammals, NMD is considered to be induced when an exon junction complex (EJC), a protein complex deposited upstream of exon-exon boundaries after RNA splicing, resides downstream of the termination codon in the first round of translation (Chang, Y. F. et al., (2007). Annu Rev Biochem 76, 51-74, Isken, O. and Maquat, L. E. (2007). Genes Dev 21, 1833-1856). It is critical to design the fluorescent reporter mini-genes so that the mRNA isoforms encoding the fluorescent proteins escape NMD. As the GFP and RFP cDNAs reside in the last exon in mini-genes shown in FIG. 2, the productive isoforms from these mini-genes would escape NMD in mammals. In *C. elegans* (Kuroyanagi, H. et al., (2007). Mol Cell Biol 27, 8612-8621, Pulak, R. and Anderson, P. (1993). Genes Dev 7, 1885-1897) and yeast (Kebaara, B. W. and Atkin, A. L. (2009). Nucleic Acids Res 37, 2771-2778, Amrani, N. et al., (2004). Nature 432, 112-118), long 3' untranslated region (UTR) triggers NMD independent of exon-exon boundaries, and therefore the mRNA isoforms encoding RFP proteins in FIGS. 2C and 2D may be degraded by NMD in these organisms.

Genomic fragments utilized in the mini-gene constructs usually undergo proper splicing. However, trimming of constitutive exons and/or deletion of long intronic regions may lead to inefficient splicing or deregulation of alternative splicing. Repeated minigene optimization may be required to establish a reporter reflecting the alternative splicing pattern of the endogenous gene. The present inventors have not experienced cryptic splicing in GFP or RFP cDNAs, but other cDNAs for N-terminal and C-terminal tags may serve as cryptic splice sites.

Amino acid sequences derived from the gene of interest may greatly affect folding, stability and/or subcellular localization of the fluorescent fusion proteins. It is therefore critical to predict the property of the fusion proteins in designing the mini-genes. Various N-terminal tags such as GST (FIG. 2D) may stabilize the expression of the fusion proteins and improve the result. It is also critical to force translation initiation at the designed initiation codon. ATG codons in the exonic regions and in the N-terminal tags may be the cause of aberrant translation initiation and reduce the production of the fluorescent proteins.

Several groups have generated reporter system to visualize splicing regulation of FGFR2 gene. Newman et al. generated fluorescent reporter vectors with the minimum genomic region that can reflect endogenous splicing regulation in AT-3 and DT-3 cells. With this reporter, they identified specific ISEs, including ISS/ISS-3, that respond to Fox regulation [Newman E A, Muh S J, et al. (2006) Rna 12: 1129-1141]. Bonano et al. constructed another fluorescent reporter vector by using the genomic fragment around exon 8, and they visualized the regulation of exon 8 inclusion in the mouse [Bonano V I, et al. (2006) Rna 12: 2073-2079]. In this invention, the present inventors originally developed a transgenic reporter system using FGFR2 gene as model and succeeded in visualizing tissue-specific expression profiles of the mutually exclusive exons through differential expression of EGFP and RFP in mice for the first time. Using the mostly entire genomic region around alternative exons with their upper and lower constitutive exons, the present inventors could evaluate which splice site sequences and cis-elements are truly critical for regulations. This system has great advantage, 1) to monitor the dynamism of splicing regulation in vivo with single cell resolution, 2) to identify essential cis-elements and trans-factors, and reveal the hidden mechanisms of splicing regulation like this study, 3) to identify the essential candidate factors by fluorescent color change or to screen the regulators using cDNA or siRNA library. In this way, splicing reporter system has great advantage to decipher the hidden splice code and also to reveal the important roles regulated by alternative splicing during development or in adult with tissue- or cell-type specific manner.

Figure 8:
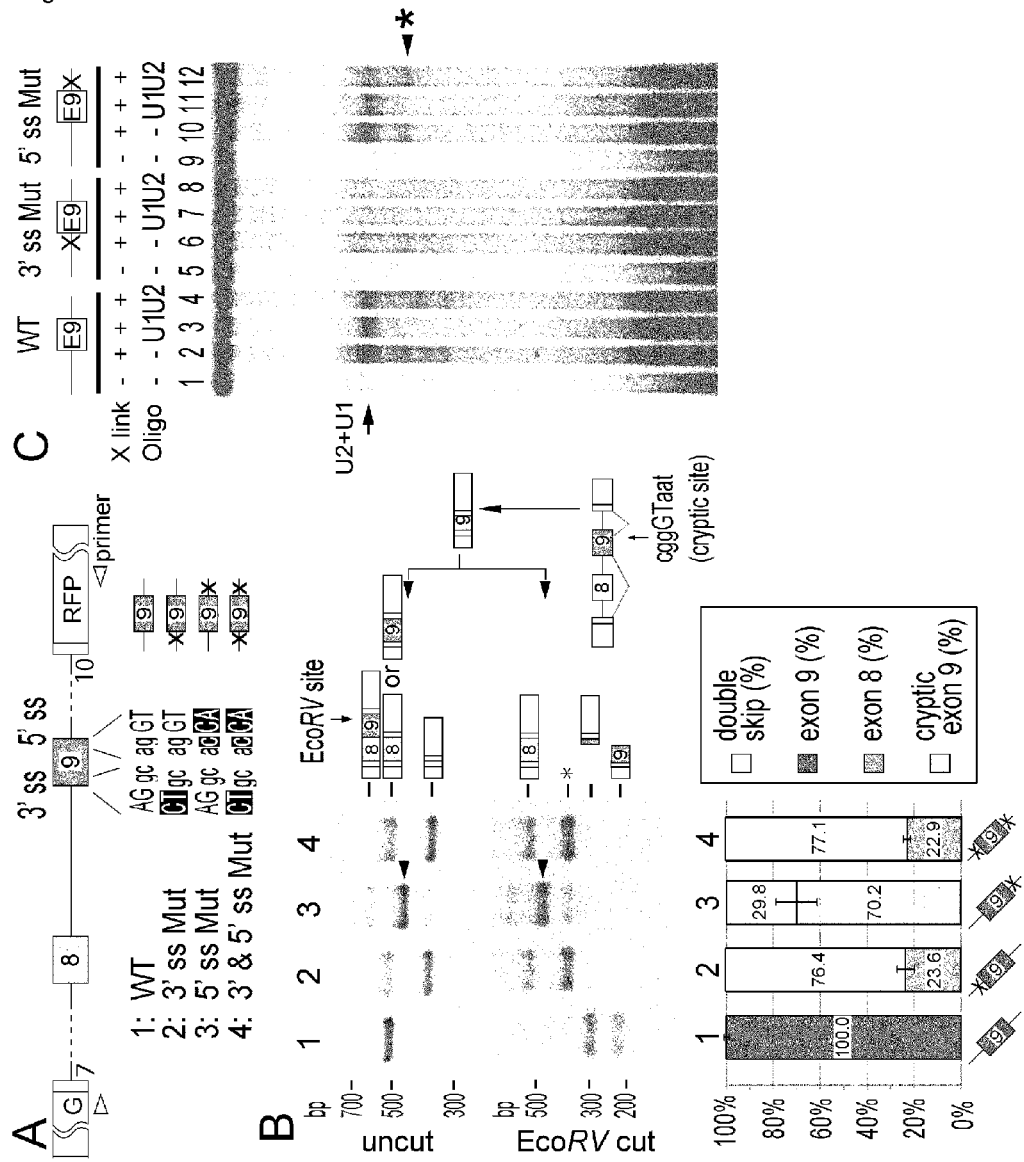
FIGS. 8A-8C show the promoted selection of exon 8 by disruption of 3' splice site of exon 9. (A) Scheme of 3' and 5' splice site mutation on exon 9. Uppercase letter is intron and lowercase is exon sequence, white characters on a black background indicates mutated sequence. (B) RT-PCR from AT-3 cells into which the indicated vectors were introduced. Arrowshead indicate aberrant spliced product that used the 5' cryptic splice site inside exon 9. The bar graph, which represents the amount of each splicing product, is based on calculations from three independent experiments; the mean value for each splice product is show in the respective column with an error bar showing the SD (standard error). (C) Results of the in vitro splice site recognition assay. The scheme for exon 9 shows the position of the splice site mutation as "x". "X-link" shows the presence or absence of UV-induced crosslinks in samples after the in vitro splicing reaction. "U1 oligo" and "U2 oligo" represent the digestion of RNA samples by RNaseH with complementary oligos for U1 or U2. The band shown by arrowheads with asterisk may be a probe crosslinked with U1 that binds to the cryptic 5' splice site inside exon 9, because it was detected in the 5' ss mutated probe and digested with U1 oligo.

With splicing reporter system, the present inventors showed that two mutually exclusive exons of FGFR2 gene seem to have "primary" and "secondary" fates. Without tissue-specific regulators, "primary" exon 9 is chosen as the "default" and the "secondary" exon 8 is ignored depending on the relative strength of their 3' splice sites (FIG. 12A, Non-Epithelial or Mesenchymal regulation). When tissue-specific key regulator ESRPs are expressed, these factors bind close to the 3' splice site of "primary" exon 9 with Fox, and repress exon 9 recognition (FIG. 12A, Epithelial regulation). Mutually exclusive alternative splicing regulated through the ordered splicing recognition with tissue specific factors has been observed in nematodes [Ohno G, et al. (2008) Genes Dev 22: 360-374]. With this ordered splice-site recognition, transacting regulators can sequentially control the selection of mutually exclusive exons in a tissue-specific manner, in a similar manner to which a chess piece, usually a knight, can simultaneously attack a rook and check the king so that the former must be lost (FIG. 12A). This regulatory mechanism clearly answered to our initial questions described above. So far, tissue-specific alternative splicing regulation has been understood from the viewpoint of the balance between enhancement and silencing of the alternative exons mediated by trans-factors through specific cis-elements [Matlin A J, et al. (2005) Nat Rev Mol Cell Biol 6: 386-398.]. In this idea, each alternative exon is regulated discretely, and the final splicing isoforms are determined from the sum and balance of these independent regulations. If this were the case in mutually exclusive alternative splicing, the initial splicing products would be mixtures of the single-exon-inclusion form, double-inclusion form, and double-skip form. As the last two isoforms would be eliminated by NMD [Chang Y F, et al. (2007) Annu Rev Biochem 76: 51-74], only the single-exon-inclusion forms would remain as final splicing products. On the other hand, if mutually exclusive splicing is regulated by the switch-like manner, the initial spliced products would consist mainly of one of the single-inclusion forms. If the exon selection in AT-3 cell is on a balance of combined regulations of enhancer for exon 9 and repressor for exon 8, overexpression of repressor for exon 9 should produce mostly the double-skip form. The present inventors did not, however, observe this (FIG. 10A). In addition, when the 3' slice site of exon 8 in the reporter was changed to be as strong as that of exon 9, the double-inclusion splicing product became dominant in AT-3 cell, without any change in the transacting factors or specific cis-elements affecting exon 8 (FIG. 7, lane 2). Also, splice site mutation of exon 9 caused switching to epithelial exon 8 in non-epithelial AT-3 cell (FIG. 8, lane 2 and 4). These results suggest that alternative splicing is not achieved by a complicated balance of multiple regulators, but is defined by a simple switch-like mechanism in which only one appropriate exon can be selected and switched by key regulators.

The present inventors' previous study showed that mutually exclusive splicing of the worm FGFR homologue gene egl-15 is regulated by the cooperation of broadly expressed Fox-1/ASD-1 family and the muscle-specific RNA binding motif proteins (RBMs) of SUP-12 (a nematode homologue of mRBM24), which act together to repress inclusion of alternative exon 5B to promote muscle-specific expression of exon 5A [Kuroyanagi H, et al. (2006) Nat Methods 3: 909-915, Kuroyanagi H, et al. (2007) Mol Cell Biol 27: 8612-8621.](FIG. 12B, nematode). In the case of mammalian FGFR2, the generally expressed Fox family cooperate with the tissue-specific factor ESRPs (RBM35a & b) to repress alternative inclusion of exon 9 and to promote epithelial tissue-specific expression of exon 8 (FIG. 12B, mammals). Moreover, both of nematode and mammalian Fox family proteins bind to the UGCAUG element, and SUP-12 and ESRPs bind to GU stretches. Nematode has rather similar number of genes (~20,000) comparing with mammals but the size of its genome is much smaller (about 1/30) with very shorter intron (average 561 bp). So, alternative splicing in nematode is considered to be regulated with much simpler rules [Zahler A M (2005) WormBook: 1-13, Kabat J L, et al. (2006) PLoS Comput Biol 2: e86.]. Thus, it is amazing that regulatory mechanism of tissue-specific alternative splicing is evolutionally conserved from nematode to mammals, and regulation though Fox and another tissue-specific RBMs may turn out to be a widespread essential phenomenon to regulate tissue-specific alternative splicing of multiple genes. The present inventors' findings also provide the significant cue to understand how a number of spliced genes are regulated in various tissue-specific manners by a limited number of regulators, eventually to understand seemingly complicated developmental process or tissue-specific functions.

All prior art documents cited in the specification are incorporated herein by reference.

EXAMPLES

Examples of the present invention are illustrated below, but these are not to be construed as limiting the present invention.

Example 1

Protocol

1. Constructing Genomic DNA Fragment Cassettes in 'Entry' Vectors

The present inventors perform the 'BP' reaction to clone genomic fragments of interest in 'Entry' vectors of the MultiSite Gateway system. To amplify attB-flanked genomic fragments, the present inventors usually perform a two-step PCR procedure. The first PCR is performed with primers that are gene-specific and contain a part of the attB sequences at their 5' ends. The first PCR product is then used as a template for the second PCR with attB adapter primers. The advantages of the two-step PCR procedure are that the gene-specific primers (GSPs) to be synthesized would be shorter and that the attB adapter primers can be used repeatedly for cloning other DNA fragments in different mini-gene projects. Here the present inventors demonstrate how to construct 'Entry' clones for '2-fragment' recombination reaction as schematically shown in FIG. 3A. The genomic DNA fragment is cloned in either of the 'Entry' vectors depending on the design of the mini-genes to be constructed (see section 2.2). The '3-fragment' and '4-fragment' recombination reactions may also work in mini-gene construction, although they are less efficient and we have few experiences.

1.1. Primer Design

The GSPs must have 12 bases of the attB site on the 5' end followed by 18 to 25 bases of template- or gene-specific sequences (Table 1; Sequences of primers used for constructing 'Entry' clones). Kozak's consensus sequence can be inserted between the attB1 and the gene-specific sequences to force translation initiation as shown in Table 1. Termination codons must be included in or excluded from the reverse GSPs, according to the design of the reporter mini-genes. If the DNA fragment is designed to be fused with N- and/or C-terminal tags, the GSPs must be carefully designed to maintain the proper reading frame in the attB sequences as indicated in Table 1.

The attB adapter primers for the second PCR consist of the following common structure: four guanine (G) residues at the 5' end followed by a 22- or 25-base complete attB sequence (Table 1).

TABLE 1

| | |
|---|---|
| GSP-attB1F | 5'-<u>AA AAA GCA GGC T</u>NN -(gene-specific sequence)-3' (SEQ ID NO: 1)<br>* To avoid generating a stop codon, NN cannot be AA, AG, or GA. |
| GSP-attB1F (with ATG) | 5'-<u>AA AAA GCA GGC T</u>CC ACC ATG G -(gene-specific sequence)-3' (SEQ ID NO: 2)<br>* Kozak consensus sequence allows efficient protein expression in eukaryote cells. |
| GSP-attB5R | 5'-<u>T ATA CAA AGT TGT</u> -(gene-specific sequence)-3' (SEQ ID NO: 3) |
| attB1adapterF | 5'-GGGG ACAAGTTTGTAC<u>AAAAAAGCAGGCT</u>-3' (SEQ ID NO: 4) |
| attB5adapterR | 5'-GGGG ACAACTTTTG<u>TATACAAAGTTG</u>-3' (SEQ ID NO: 5) |
| GSP-attB5F | 5'-<u>AT ACA AAA GTT G</u> -(gene-specific sequence)-3' (SEQ ID NO: 6) |
| GSP-attB2R | 5'-<u>A GAA AGC TGG GT</u> -(gene-specific sequence)-3' (SEQ ID NO: 7) |
| attB5adapterF | 5'-GGGG ACAACTTTGT<u>ATACAAAGTTG</u>-3' (SEQ ID NO: 8) |
| attB2adapterR | 5'-GGGG ACCACTTTGTAC<u>AAGAAAGCTGGGT</u>-3' (SEQ ID NO: 9) |

Underlines indicate 12 bases of the attB sequences included in the GSPs.

1.2. Performing PCR

The PCRs should be performed with a proofreading polymerase, such as PRIMESTAR® HS DNA Polymerase (TaKaRa). The annealing temperature of the second PCR should be 45 degrees C. because the annealing sequences are just 12 base pairs.

Protocol 1: Two-Step PCR Amplification of attB-DNA Fragments

1. Perform the first PCR in a 25 microliter (microL) mixture containing standard reagents with 0.2 microM each of GSPs. The conditions of the PCR should be optimized depending on the amount of the template and the size of the fragment to be amplified. Check the PCR product by standard agarose gel electrophoresis.

2. Prepare 50 microliter (microL) of the second PCR mixture containing standard reagents and 0.3 microM each of attB adapter primers. Add the mixture to 10 microliter (microL) of the first PCR reaction mixture and perform 5 cycles of PCR with annealing at 45 degrees C. Check by agarose gel electrophoresis that the amount of the PCR product has increased in the second PCR.

3. Optionally, add 1 microliter (microL) Dpn I* (New England Biolabs) and incubate at 37 degrees C. for 1 hour to destroy template DNA. *If the PCR template is a plasmid containing the kanamycin-resistance gene, the PCR mixture should be treated with Dpn I before purifying the attB-PCR products. Dpn I recognizes methylated GATC sites in bacteria-derived DNA. Dpn I treatment greatly reduces background in the 'BP' recombination reaction associated with template contamination.

4. Purify the attB-PCR product with a standard DNA purification column.

1.3. 'BP' Recombination Reaction and Selection of 'Entry' Clones

Perform 'BP' recombination reaction between each attB-flanked DNA fragment and an appropriate attP-containing 'Donor' vector (Table. 2: Selection of 'Donor' vectors for constructing 'Entry' clones by 'BP' reaction) to generate an 'Entry' clone.

TABLE 2

| pDONR Vectors | DNA fragments to be cloned | pENTR Vectors generated |
|---|---|---|
| pDONR 221 P1-P5r | attB1F/attB5R-flanked PCR products | pENTR-L1-R5 |
| pDONR 221 P5-P2 | attB5F/attB2R-flanked PCR products | pENTR-L5-L2 |

Protocol 2: BP CLONASE II® Enzyme Mix Reaction and Selection of Appropriate 'Entry' Clones 1. Add the following components to a 1.5-ml microcentrifuge tube and mix: attB-PCR product (15 to 150 ng), pDONR vector (supercoiled, 75 ng), and deionized distilled water (DDW) or TE to 4 microliter (micro L). Add 1 microliter (microL) BP CLONASE II® enzyme mix (Invitrogen) to the components above and mix well by briefly vortexing or tapping.

2. Incubate the 'BP' reaction mixture at room temperature or at 25 degrees C. for 1 hour or overnight. We usually omit proteinase K digestion.

3. Transform E. coli strain DH5alpha or others* with 1 to 3 microliter (microL) of the reaction mixture and select for kanamycin-resistant 'Entry' clones. Check the sequence of the insert. *E. coli strains with F' episome (e.g. TOP10F') cannot be used for transformation to select 'Entry' clones. These strains contain the ccdA gene and will prevent negative selection with the ccdB gene in the pDONR vectors.

1.4. Modification of 'Entry' clones (Optional)

According to the design of the mini-genes, introduce a termination codon or a frame-shift into exons, and/or modify or disrupt putative cis-elements of the 'Entry' clones. Sequences of the genomic fragment should be carefully modified to avoid disruption of putative cis-regulatory elements. The present inventors introduce termination codons or frame-shifts in less conserved stretches among related species. The present inventors utilize Quickchange II or Quickchange II XL (Stratagene) for the site-directed mutagenesis. The present inventors usually sequence the entire insert after mutagenesis.

2. 'LR' Recombination Reaction and Selection of 'Expression' Clones

Gateway 'Destination' vectors usually provide a promoter and a 3' cassette (FIG. 2). A variety of 'Destination' vectors for expression in cultured cells are commercially available. 'Destination' vectors can also be constructed by ligation-based insertion of Destination vector cassettes (Invitrogen) into existing vectors containing the ampicillin-resistance gene. The present inventors performed 'BP' reaction to convert existing expression vectors into 'Destination' vectors, which were used in our previous studies [Ohno, G., et al., (2008) Genes Dev 22, 360-374, Kuroyanagi, H. et al., (2006) Nat Methods 3, 909-915, Kuroyanagi, H. et al., (2007) Mol Cell Biol 27, 8612-8621.]. The present inventors can convert any existing vectors containing the ampicillin-resistance gene into 'Destination' vectors at desired positions with desired frames. Details of the conversion method will be described elsewhere [Kuroyanagi, H. et al., (in press) Nat. Protoc.]. Nucleotide sequences of the 'Destination' vectors the present inventors constructed for expression in *C. elegans* are available on the *C. elegans* Promoter/Marker Database (http://www.shigen.nig.ac.jp/c.elegans/promoter/index.jsp).

The present inventors have constructed a variety of 'Entry' clones of fluorescent protein cassettes in pENTR-L1-R5 and pENTR-L5-L2 vectors with or without initiation and/or termination codons.

Protocol3: LR CLONASE II PLUS® Enzyme Mix Reaction and Selection of Appropriate 'Expression' Clones.

1. Add the following components to a 1.5-ml microcentrifuge tube and mix: Destination' vectors (75 ng), 'Entry' clones (15 to 100 ng each), DDW or TE to 4 microliter (microL). Add 1 microliter (microL) LR CLONASE II PLUS® enzyme mix (Invitrogen) to the components above and mix well by briefly vortexing or tapping.

2. Incubate the 'LR' reaction mixture at 25 degrees C. or at room temperature overnight. The present inventors usually omit the proteinase K digestion.

3. Transform *E. coli* strain DH5alpha or others* with 1 to 3 microliter (microL) of the reaction mixture and select for ampicillin/carbenicillin-resistant 'Expression' clones. The present inventors routinely check resistance of the ampicillin/carbenicillin-resistant colonies to ampicillin/carbenicillin, chloramphenicol and kanamycin. *E. coli* strains with F' episome cannot be used to select 'Expression' clones.

4. Select clones that are resistant only to ampicillin/carbenicillin, check restriction enzyme digestion patterns of the mini-prep plasmid DNAs and sequence the boundaries of the DNA fragments.

3. Transfection of Cultured Cells and Generation of Transgenic Animals.

Transient transfection of cultured cells with the fluorescent reporter mini-gene(s) is performed using standard transfection reagents. Expression of the fluorescent proteins can be analyzed by utilizing standard compound microscopes, flow cytometry and other instruments.

Transgenic animals can be generated by standard methods. Expression of the fluorescent proteins in mice can be analyzed by observing sections under compound microscopes or confocal microscopes. The present inventors usually utilized high-magnification fluorescence dissection microscopes or confocal microscopes to analyze cell- and tissue-specific expression of the fluorescent reporter proteins in transgenic worms.

4. Checking Splicing Pattern of the Mini-Gene-Derived mRNAs.

The present inventors strongly recommend analyzing splicing patterns of the mini-gene-derived mRNAs to confirm that the reporter mini-genes are expressed and properly spliced and that the alternative splicing pattern is as expected from that of the endogenous gene and is consistent with the ratio of the expressed fluorescent proteins.

Protocol 4: RT-PCR Analysis of Mini-Gene-Derived mRNAs

1. Total RNA is extracted from cells, tissues or organisms by utilizing RNEASY MINI® extraction kit (QIAGEN) or equivalents and DNase I following manufacturer's instructions.

2. In RT, 1 to 2 microgram of the total RNA is reverse transcribed with PrimeScript (TaKaRa) or Superscript II (Invitrogen) and oligo(dT) as a primer following manufacturers' instructions.

3. For PCR, the present inventors usually use nonproofreading polymerases such as Ex Taq (TaKaRa) and BIO-TAQ® polymerase (BIOLINE), and a mini-gene-specific primer set. As GFP-specific reverse primers, the present inventors use 5'-TGTGGCCGTTTACGTCG-3' (SEQ ID NO: 10) or 5'-TTTACTTGTACAGCTCGT-3' (SEQ ID NO: 11). As mRFPspecific reverse primers, the present inventors use 5'-GGAGCCGTACTGGAACTGAG-3' (SEQ ID NO: 12) or 5'-TTAGGCGCCGGTGGAGTG-3' (SEQ ID NO: 13). attB adapter primers can also be used.

4. To analyze RT-PCR products, directly sequence the purified products, or clone the products in TA-vectors such as PGEM-T EASY® (Promega) and sequence them.

Example 2

Examples of Experiments

Figure 4:
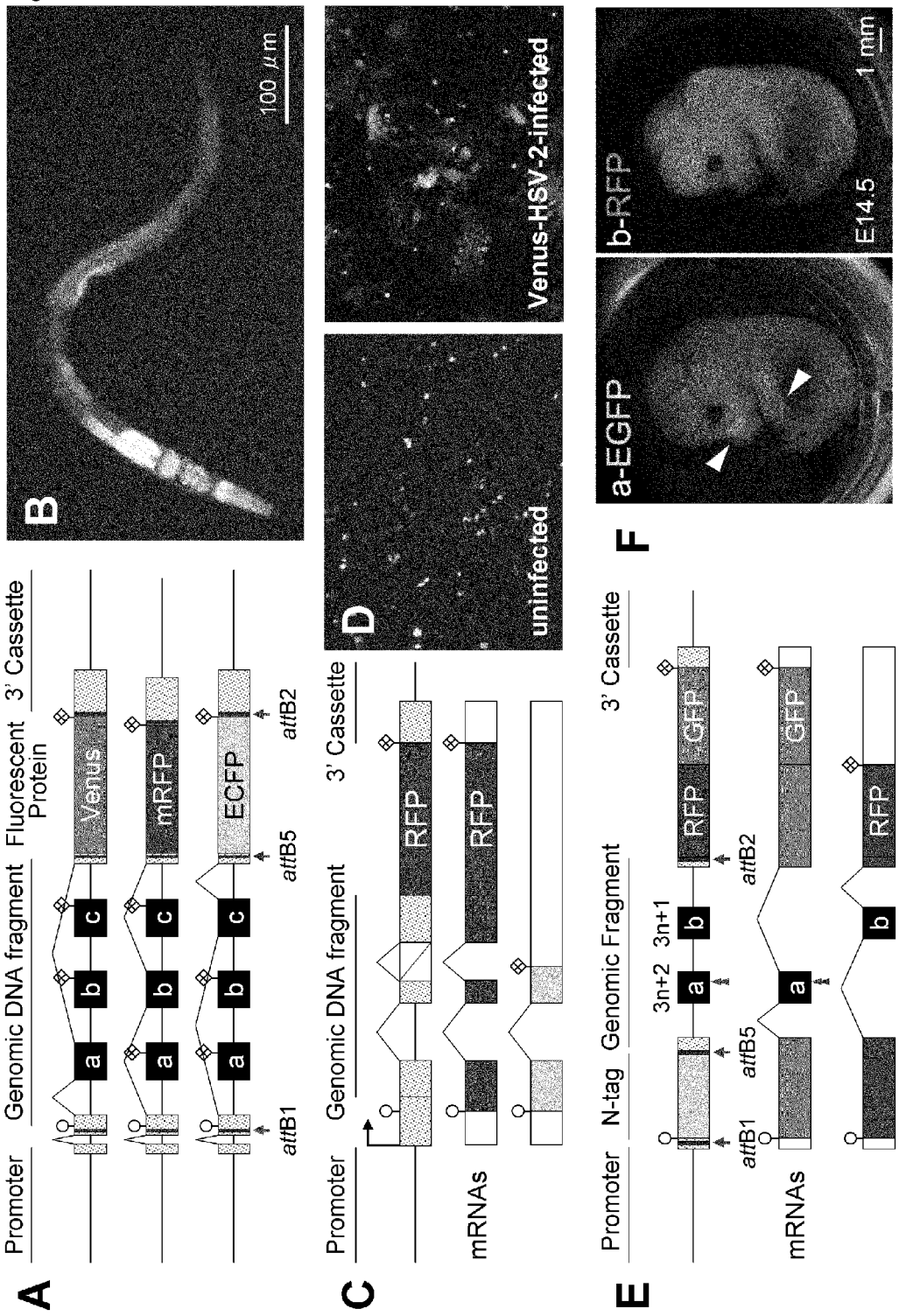
FIGS. 4A-4F show examples of the analysis. (A, B) Visualization of mutually exclusive alternative splicing in *C. elegans*. (A) Schematic structure of a trio of reporter minigenes to monitor selection profiles of three mutually exclusive exons (a, b and c). The promoter, the constitutive first intron and the 3' cassette were provided by a 'Destination' vector. Two termination codons (diamonds) are introduced into two of the alternative exons in each construct. attB sites are indicated with arrows. (B) A microphotograph of a fluorescent alternative splicing reporter worm carrying the minigenes in (A). Expression of Venus (green), mRFP (red) and ECFP (blue) shows tissue-specificity. (C, D) Visualization of virus-induced intron retention. (C) Schematic structure of a reporter mini-gene to monitor splicing of an alternatively retained intron, and mRNAs derived from it. RFP protein is produced only when the alternative intron is properly spliced. (D) Microphotographs of uninfected (left) and Venus-HSV-2-infected (right) HeLa cells. All uninfected cells express RFP (magenta), while cells infected with Venus-HSV-2 (green) shut off RFP expression. (E, F) Visualization of tissue-specific alternative splicing in mice. (E) Schematic structure of a reporter mini-gene to monitor selection of mutually exclusive alternative exons, and mRNAs derived from it. GFP protein is produced when exon a alone is selected and RFP is produced when exon b alone is selected. (F) Microphotographs of a mouse embryo at E14.5. (Left) Expression of GFP is detected in epidermis (arrowheads). (Right) Expression of RFP is detected in the nervous system and mesenchymal tissues.

FIGS. 4A and 4B show an example of visualizing tissue-specific alternative splicing of mutually exclusive exons in *C. elegans*. FIGS. 4C and 4D show an example of visualizing viral infection-induced intron retention in HeLa cells [Nojima, T. et al., (2009) Nucleic Acids Res 37, 6515-6527.]. FIGS. 4E and 4F show an example of visualizing mutually exclusive alternative splicing in mice.

Formal names of the abbreviations used in the present specification can be shown below.

ABBREVIATIONS

EJC, exon junction complex;
GFP, green fluorescent protein;
GSP, gene-specific primer;
GST, glutathionine S-transferase;
mRNA, messenger RNA;
NMD, nonsense-mediated mRNA decay;
PCR, polymerase chain reaction;
PTC, premature termination codon;
RFP, red fluorescent protein;
RT, reverse transcription;
UTR, untranslated region.

MATERIALS AND GLOSSARY

TABLE 3

| | |
|---|---|
| pENTR-L1-R5 and pENTR-L5-L2 | These are vector backbones of the 'Entry' vectors and the maps are schematically drawn in "1-page summary" and FIG. 2A, 2B. |
| nonsense-mediated mRNA decay (NMD). | An mRNA quality-control mechanism that degrades abnormal mRNAs with premature termination codons arising from genetic mutations or a consequence of mistakes in gene expression. |

TABLE 3-continued

| | |
|---|---|
| exon junction complex (EJC), | A complex of proteins deposited as a consequence of pre-mRNA splicing ~20-24 nucleotides upstream of splicing-generated exon-exon junctions of newly synthesized mRNA. |
| TaKaRa | Seta 3-4-1, Otsu, Shiga 520-2193, Japan http://www.takara-bio.com/ |
| BIOLINE | London, UK www.bioline.com |

Materials & Methods

Plasmid Construction

The present inventors constructed the reporter vector essentially as described in the text. The FGFR2 genomic region spanning from exon 7 to exon 10 from mouse genomic DNA was amplified by PCR and cloned into GATEWAY DESTINATION® Vector (Invitrogen), carrying both EGFP (Clontech) and mRFP [Campbell R E, et al. (2002) Proc Natl Acad Sci USA 99: 7877-7882.] with different reading frames, under the control of the CAGGS promoter. To stabilize and enhance reporter protein expression, artificial sequence of modified glutathione S-transferase (GST) gene (QIAGEN) was introduced in front of the FGFR2 genomic fragment and connected in frame with exon 7. A 1-kbp fragment at the center of the FGFR2 intron 9 was removed because of its significant reducing effect in mRNA expression. Mutations of cis-elements were introduced by using QUIKCHANGE XL II® (Stratagene). Mouse Fox 1 and Fox2 cDNAs were kindly provided by Dr. Kawamoto [Nakahata S, Kawamoto S (2005) Nucleic Acids Res 33: 2078-2089.] and cloned into the GATEWAY DESTINATION® vector driven by a CAGGS promoter. Primer sequences for amplifying FGFR2, deleting 1 kbp in the middle of intron 9, and introducing mutations were indicated below.

Primer sequences for amplifying FGFR2, deleting 1 kbp in the middle of intron 9, and introducing mutations;

```
FGFR2 amplify-F:
                                (SEQ ID NO: 14)
ggctgccctacctcaaggtcctg FGFR2 amplify-R:
                                (SEQ ID NO: 15)
ctctctcacaggcgctgggttgcag intron 9 partial deletion-F:
                                (SEQ ID NO: 16)
gcatgccttgatagagtggcctctc-ctgttgaaccttcccctggag intron 9 partial deletion-R:
                                (SEQ ID NO: 17)
ctccaggggaaggttcaacag-gagaggccactctatcaaggcatgc exon 9 mutation for deleting PTC-F:
                                (SEQ ID NO: 18)
gaggttctctatattcggaatgtTacttttgaggatgctggg exon 9 mutation for deleting PTC-R:
                                (SEQ ID NO: 19)
cccagcatcctcaaaagtAacattccgaatatagagaacctc exon 9 3' splice site mutation-F:
                                (SEQ ID NO: 20)
gcttcgtttgttttctctgccgccggtgttaacaccacggac exon 9 3' splice site mutation-R:
                                (SEQ ID NO: 21)
gtccgtggtgttaacaccggcggcagagaaaacaaacgaagc exon 9 5' splice site mutation-F:
                                (SEQ ID NO: 22)
ctgcatggttgacagttctgccaccaacatactgctctttctctc exon 9 5' splice site mutation-R:
                                (SEQ ID NO: 23)
gagagaaagagcagtatgttggtggcagaactgtcaaccatgcag TGCATG mutation-F:
                                (SEQ ID NO: 24)
gggccaatttttccatgtgttcaatttacgtacgttctaggtggtgacg TGCATG mutation-R:
                                (SEQ ID NO: 25)
cgtcaccacctagaacgtacgtaaattgaacacatggaaaaattggccc ISE/ISS-3 mutation-F:
                                (SEQ ID NO: 26)
taggtggtgacgccgaatctcctgatggcc ISE/ISS-3 mutation-R:
                                (SEQ ID NO: 27)
ggccatcaggagattcggcgtcaccaccta
```

Generation of FGFR2 Splicing Reporter Mice

The constructed FGFR2 splicing reporter vector was linearized and injected into the pronucleus of a C57BL/6 oocyte. Mice were genotyped by PCR with primers for EGFP using genomic DNA from the postnatal and late embryonic tails, or yolk sacs from earlier embryos. All experiments were performed in accordance with the protocols certified by the Institutional Animal Care and Use Committee of the Tokyo Medical and Dental University (Approval Numbers #0070220, #0080179, and #0090084).

Cell Culture and Transfection

Rat AT-3 and DT-3 prostate carcinoma cell lines were kindly provided by Dr. Garcia-Blanco and Dr. Carstein. Cells were maintained in Dulbecco's modified eagle medium (D-MEM) with 10% fetal calf serum (FCS), and vectors were transfected with TRANSFECTIN® reagent (BIORad). Stealth siRNA was used in knockdown experiments on endogenous Fox2 and was transfected using LIPOFECTAMINE® RNAiMAX reagent (Invitrogen).

Microscopy

Fluorescent images of whole embryos of reporter transgenic mice were capture under a fluorescence microscope (MZ16FA, Lecia) with a charge-coupled device (CCD) camera (DP71, Olympus). The present inventors also used a confocal microscope (Fluoview FV1000, Olympus) to capture fluorescent images of sectioned transgenic embryos, and the captured images were processed by means of METAMORPH® software (Molecular Devices). Fluorescent images of cultured cells and bright-field images showing in situ hybridization were captured by using a Nikon Eclipse E600 microscope with a CCD camera (DP71, Olympus).

RT-PCR

Total RNAs and RT-PCR were performed as described previously [Kuroyanagi H, et al., (2006) Nat Methods 3: 909-915, Takeuchi A, et al. (1998) Eur J Neurosci 10: 1613-1620.]. The identity of all splicing variants was confirmed by sequencing. Amounts of PCR products were measured with a 2100 BioAnalyzer with Agilent DNA1000 kits (Agilent Technology), and the quantitative analyses were performed in more than three independent experiments.

Primer sequences used in the RT-PCR assays are listed below.

Primer sequences used in the RT-PCR assays;

```
Reporter FGFR2-F
                                (SEQ ID NO: 28)
5'-GGCCTTTGCAGGGCTGGC-3'
```

-continued

```
Reporter FGFR2-R
                                    (SEQ ID NO: 29)
5'-GGAGCCGTACTGGAACTGAGG-3'

Fox1-F
                                    (SEQ ID NO: 30)
5'-GGCACCGCCACACAGACAGATGA-3'

Fox1-R
                                    (SEQ ID NO: 31)
5'-TCCTGGTTGGCCTGGCACAACAG-3'

Fox2-F
                                    (SEQ ID NO: 32)
5'-CAACAACTCCTGACGCAATGGTTCAGC-3'

Fox2-R
                                    (SEQ ID NO: 33)
5'-GATTTTACGGCCCTCTACCACGGTG-3'

ESRP1-F
                                    (SEQ ID NO: 34)
5'-CAGGAGATGCCTTTATCCAGATGAAGTC-3'

ESRP1-R
                                    (SEQ ID NO: 35)
5'-CAGTATTGTAGGCCAGGCCCTG-3'

ESRP2-F
                                    (SEQ ID NO: 36)
5'-CCTACACAGCCACCATTGAAGACATTC-3'

ESRP2-R
                                    (SEQ ID NO: 37)
5'-GGTGAGGTAGCCCACAGTAGTG-3'
```

In Vitro Exon-Recognition Assay

Figure 5:
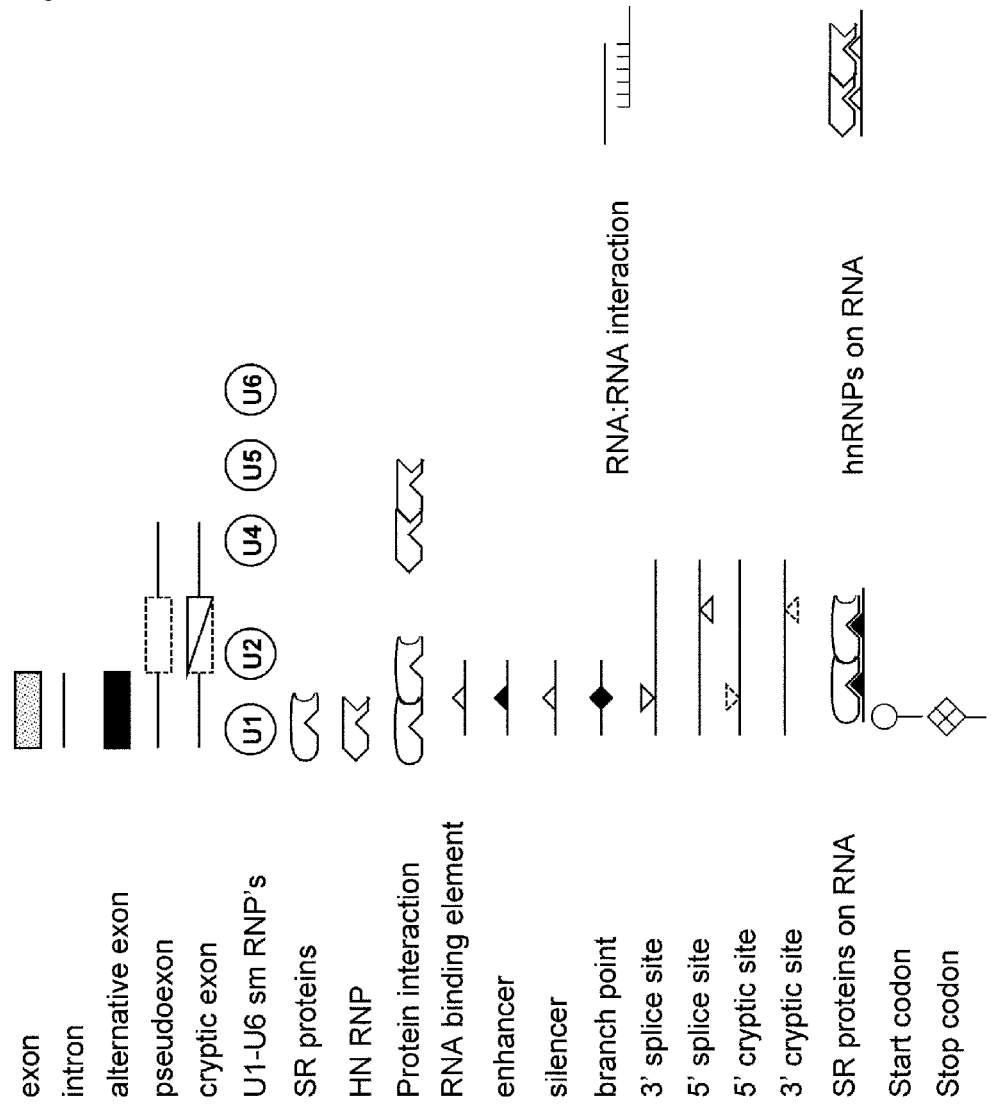
FIG. 5 shows the meaning of each symbol used in the FIGS. 1 to 4.

The PCR products of T7-ex 9 wt (mouse FGFR2 intron 8, 200 nt; exon 9, 145 nt; and intron 9, 105 nt), T7-ex 9 containing UGCAUG and ISE/ISS-3 in intron 8 (intron 8, 237 nt; exon 9, 145 nt; and intron 9, 74 nt), and T7-ex 8 wt (intron 8, 200 nt; exon 8, 149 nt; and intron 9, 100 nt) were used as DNA templates for T7 transcription. A mutated DNA template of 3' ss in intron 8 and 5' ss in intron 9 was prepared from mutated reporter vectors as shown in FIG. 3A. The RNA substrates were labeled with $^{32}P$ by in vitro T7 transcription. In vitro splicing reaction and UV cross linking were performed under the conditions described by Sawa [Sawa H, Shimura Y (1992) Genes Dev 6: 244-254.]. To identify the shifted bands by UV cross linking, pre-heated cDNA oligo (10 microgram/mL) for U1 (5'-CGGAGTGCAATG-3'/SEQ ID NO:38) or U2 (5'-CAGATACTACACTTG-3'/SEQ ID NO:39) was added to the RNAs after UV cross linking, and the U1 or U2 cDNA oligo/ RNAs mixture were digested with 50 U/mL of RNase H at 30 degrees C. for 10 min. In FIG. 5C, highly purified Flag-Fox2 and Flag-ESRP1 were added to RNAs and incubated at room temperature for 5 min before splicing reaction to examine their inhibitory or activating effects on exon recognition of U1 snRNA or U2 snRNA. After these reactions, RNAs were subjected to denaturing PAGE analysis and autoradiography.

In Situ Hybridization

In situ hybridization was carried out as previously described [Takeuchi A, et al. (2003) Nat Genet. 33: 172-176, Takeuchi A, O'Leary D D (2006) J Neurosci 26: 4460-4464.], with modifications. Briefly, embryos were fixed with 4% paraformaldehyde, cryo-protected with 30% sucrose, embedded in optimal cutting temperature (OCT) compound, and cut into sections in 20 micrometer thickness. Antisense RNA probes labeled with digoxigenin were visualized with Fab fragments from an antibody against digoxigenein conjugated with alkaline phosphatase (Roche) and 5-bromo-4-chloro-3-indolyl phosphate (BCIP)/Nitroblue Tetrazolium (NBT) solutions. Sections were counterstained with Methyl Green. The following cDNA was used as the riboprobe: Fox1 (131-865 bp from mouse cDNA), Fox2 (2261-2991 bp from mouse cDNA), ESRP1 (1168-1708 bp from mouse cDNA), and ESRP2 (208-807 bp from mouse cDNA).

Example 3

Generation of the FGFR2 Splicing Reporter System

The present inventors used a 3.7-kb genomic fragment of FGFR2 gene that included two alternative exons (exon 8 and 9) flanked by their upstream and downstream exons (exon 7 and 10), with introns in between (FIG. 6A). By using mostly entire genomic region around alternative exons, this reporter system was expected to contain all the regulatory cis-elements essential for tissue-specific regulation and to tell which splice site sequences and cis-elements are truly critical for regulations. The genomic fragment was cloned into a vector containing RFP and EGFP in tandem with different reading frames [Orengo J P, et al., (2006) Nucleic Acids Res 34: e148.]. With this reporter system, splicing regulation could be monitored from a single reporter vector that expresses either EGFP when exon 8 is chosen or RFP when exon 9 is selected (FIG. 6A).

By using two prostate carcinoma cell lines, AT-3 and DT-3 cells, the present inventors then examined whether the reporter system could reflect cell type-specific splicing regulation. AT-3 cell is a mesenchymal-type cell that specifically expresses exon 9 isoform of endogenous FGFR2, and DT-3 cell is an epithelial-type cell that predominantly expresses exon 8 isoform [Yan G, et al., (1993) Mol Cell Biol 13: 4513-4522.]. When this reporter system was introduced into these two cell lines, AT-3 cell specifically expressed exon 9-RFP and DT-3 cell predominantly expressed exon 8-EGFP (FIG. 6B). The present inventors therefore could confirm that their reporter vector reflects cell type-specific regulation of endogenous FGFR2 splicing.

The present inventors next checked whether their reporter system could show tissue-specific regulation of FGFR2 splicing in vivo by generating transgenic mice from this reporter. A well-known change in the FGFR2 splicing isoforms occurs in mouse development stages from E14.5 to E16.5. In these stages, differentiation of future epithelial cells is induced and they start expressing exon 8 isoform of FGFR2 to receive morphogen signals, such as FGF-10, from mesenchymal cells [Finch P W, et al., (1995) Dev Dyn 203: 223-240.]. When the whole body of a transgenic embryo was examined at E14.5, a broad RFP signal was detected throughout the entire body, and a specific EGFP signal was detected as the whisker pattern and on the edges of limbs or the body (FIG. 6C). The present inventors further evaluated the detailed expression profile through examining series of sections from the transgenic embryos in the late development stage of E16.5 (FIG. 6D). An EGFP signal was detected specifically in cells on the surface of the skin and bulbs of hair follicles, where differentiated epithelial cells were located (FIG. 6D, shown with arrows). Also, the EGFP signal was detected at epithelial cells in the alveoli of the lung, in the esophagus and colon, at the thymus epithelia, and at the salivary gland ductal cells (FIG. 6D, arrows in the top and middle panels). A strong RFP signal was detected in the developing brain (hippocampus) and peripheral nervous system (trigeminal ganglia) (FIG. 6D, arrows in bottom panels). Expression patterns of EGFP were compatible with reported FGFR2 exon 8 expression patterns [Finch P W, et al., (1995) Dev Dyn 203: 223-240. Orr-Urtreger A, et al. (1993) Dev Biol 158: 475-486.], indicating that the present inventors' reporter system reflects endogenous splicing regulation of FGFR2 in vivo and the genomic fragment used in the vector contains the regulatory elements necessary for tissue-specific switching of mutually exclusive exons.

Example 4

Unbalanced Sequence of 3' Splice Site is Essential for Mutually Exclusive Exon Selection In the embryos of splicing reporter transgenic mouse, RFP was expressed almost throughout the entire body, and EGFP was specifically expressed in epithelial cells. This expression pattern suggest the possible regulatory mechanism that exon 9 was dominantly selected as "default" in reporter transgenic mouse, and epithelial-specific regulators might promote inclusion of exon 8. To test this hypothesis, the present inventors initially compared sequence of alternative exons including their 3' and 5' splice sites. The major difference identified between these two exons is that exon 8 has a weaker 3' splice site and a polypyrimidine moiety that contains several mismatches from the consensus sequence (FIG. 7A, TGTTCTAG ca/SEQ ID NO: 40), whereas exon 9 has stronger 3' splice site which has conserved consensus sequences (FIG. 7A, TTTTCTAG gc/SEQ ID NO: 41). There are no obvious differences in their 5' splice sites (data not shown). To examine whether the unbalanced 3' splice site is essential for "default" selection of exon 9 in non-epithelial cells, the present inventors introduced mutations in their 3' splice sites and observed change in splicing regulations. The present inventors prepared two types of mutated vectors, one has the same stronger 3' splice sites on both exon 8 and 9 (FIG. 7A, E8-S vector), and the other has the same weaker 3' splice sites on both exon 8 and 9 (FIG. 7A, E9-W vector). These vectors were transfected into AT-3 and DT-3 cells, and the change of splicing regulation was examined by RT-PCR. When WT vector was introduced into AT-3 cell, it adopted almost 100% of the exon 9 form, whereas DT-3 cell adopted around 45% {34.5/(34.5+ 42.7) %} of exon 8 form among the single inclusion product (FIG. 7B, lane 1, 4), which was consistent with the expression pattern of fluorescence in FIG. 6B. The present inventors' splicing reporter was designed not to cause early premature termination codon in double-inclusion form to escape the nonsense-mediated decay (NMD) reaction [Chang Y F, et al., (2007) Annu Rev Biochem 76: 51-74]. The present inventors therefore could monitor all splicing products, including the double-inclusion and the double-skip forms. Strikingly, when E8-S vectors were transfected, AT-3 cell mostly expressed the double-inclusion form, meaning that two alternative exons were processed as constitutive exons (FIG. 7B, lane 2). This result indicates that the weaker 3' splice site of exon 8 is critical for single exon selection of exon 9 from two mutually exclusive exons in non-epithelial AT-3 cell (FIG. 7B, lane 2). Also, this result indicated that exon 8 in AT-3 cell is not fully silenced by the hypothetical repressor(s), but merely ignored as a non-exon sequence in WT vector due to its weaker 3' splice site, because the reported exonic and intronic splice silencers sequence around exon 8 were not mutated in these vectors [Carstens R P, et al., (2000) Mol Cell Biol 20: 7388-7400, Del Gatto F, Breathnach R (1995) Mol Cell Biol 15: 4825-4834, Wagner E J, et al. (2005) J Biol Chem 280: 14017-14027.]. When the 3' splice site of exon 9 was weakened (E9-W vector), selection in DT-3 cell almost fully switched to exon 8 (FIG. 7B, lane 4 and 6), indicating that full repression of exon 9 might be important for exon 8 inclusion in epithelial DT-3 cell. Thus unbalanced 3' splice sites are essential for the single exon choice from mutually exclusive exons and for their switching.

Example 5

Disruption of Exon 9 Causes Switching to Exon 8

Results in FIG. 7 showed that weaker 3' splice sites of exon 8 is essential for the single exon selection of exon 9 in non-epithelial AT-3 cell. And epithelial DT-3 cell efficiently chose exon 8 form when 3' splice site of exon 9 was weakened. These observations suggest a possibility that repression of exon 9 causes switching to exon 8. To examine this hypothesis, the present inventors introduced mutations on either or both of the 3' and 5' splice sites of exon 9 to destroy its splice site consensus sequence mimicking repression, and transfected these into AT-3 cell (FIG. 8A). When both splice sites of exon 9 were mutated (FIG. 8A, 3'&5' ss Mut), AT-3 cell expressed the exon 8 form (22.9%) and the double-skip form (77.1%) (FIG. 8B, lane 4). These results indicated that blocking of exon 9, at least partially, promotes switching to exon 8 in AT-3 cell. Interestingly, mutation of the 3' splice site (FIG. 8A, 3' ss Mut) was just sufficient to cause this switching (FIG. 8B, lane 2), whereas mutation of the 5' splice site (FIG. 8A, 5' ss Mut) produced an aberrant splicing product of exon 9 using a cryptic 5' splice site at ggGT in exon 9 (FIG. 8B, lane 3 indicated by arrowhead and scheme was illustrated on the right side). These results indicate that recognition of 3' splice site is essential for exon 9 selection, suggesting the possibility that recognition of exon 9 is its 3' splice site dependent. To test this hypothesis, the present inventors performed in vitro splicing assay to directly monitor the splice site recognition by U2 and U1 snRNA/snRNP binding (FIG. 8C). The $^{32}$P-labeled RNA probes for wild-type and mutated exon 9 containing the flanking introns (top panels of FIG. 8C) were crosslinked by UV irradiation after incubation with HeLa nuclear extract and separated by electrophoresis. HeLa cell was confirmed to have non-epithelial cell character as shown in FIG. 10A. The specificity of U2 or U1 binding was confirmed by addition of an oligonucleotide complementary to U2 or U1, and RNase H digestion [Konarska M M, Sharp P A (1986) Cell 46: 845-855, Sawa H, Shimura Y (1992) Genes Dev 6: 244-254.] (FIG. 8C). Under splicing conditions, binding and shift of U1 and U2 snRNAs were observed with the WT RNA probe, in which the U1 and U2 bands overlap (FIG. 8C, lane 1-4, indicated by arrow). Strikingly, probe possessing the 3' splice site mutation resulted in a total loss of shifted band in both U1 and U2 (FIG. 8C, lane 5-8). These results showed that recognition of exon 9 totally depends on the binding of U2 snRNA to the 3' splice site. To the contrary with the probe harboring with 5' splice site mutation (5' ss mutation), binding of both U1 and U2 was retained (FIG. 8C, lane 9-12), in good accordance with the results of RT-PCR shown in FIG. 8B, lane 3. These results suggest a possibility that binding of U2 snRNA supports the binding of U1 snRNA, so that much weaker cryptic 5' splice sites in exon 9 was used in its 5' ss mutation (FIG. 8B, lane 3 and FIG. 8C, lane 12 indicated by arrowheads with asterisk). These observations can explain why the selective use of exon 9 in non-epithelial cells depends on the relative strength of its 3' splice site. A model shown in FIG. 12A, Non-Epithelial or Mesenchymal regulation could be proposed.

Example 6

Identification of Silencing Elements for Exon 9 Recognition

As shown in FIG. 12A, Non-Epithelial or Mesenchymal regulation, unbalanced 3' splice sites are essential for single exon selection of exon 9 in non-epithelial cells and recognition of exon 9 is its 3' splice site dependent. Also disruption of this 3' splice site of exon 9 partially caused switching to exon 8. These results suggest the presence of silencer(s) for exon 9 to cause switching to exon 8 in epithelial cell. To test this hypothesis, the present inventors initially screened suppressive cis-elements located near the 3' splice site of exon 9, and picked up two highly conserved sequences: the UGCAUG sequence and ISE/ISS-3 (intronic splicing enhancer/silencer-3) in intron 8, both of which have been reported as the silencing cis-elements for exon 9 [Baraniak A P, et al., (2006) Mol Cell Biol 26: 1209-1222, Hovhannisyan R H, Carstens R P (2005) Mol Cell Biol 25: 250-263.] (FIG. 9A). To examine whether these two cis-elements are essential for silencing exon 9, the present inventors introduced mutations in either or both UGCAUG and ISE/ISS-3 in their reporter, and transfected into epithelial DT-3 cell. First, the present inventors substituted UGCAUGCAUG (SEQ ID NO: 42) for UACGUACGUG (SEQ ID NO: 43) to disrupt the binding to the RNA-binding protein of Fox, which was reported as the repressor of exon 9 [Baraniak A P, et al., (2006) Mol Cell Biol 26: 1209-1222]. Then, the ratio of exon 8 selection in DT-3 cell fell by a half (44.7% to 21.9%, FIG. 9B, lane 2). Next, the present inventors deleted ISE/ISS-3, an 85-bp sequence containing several dinucleotide GU sequences. The deletion of ISE/ISS-3 reduced the ratio of exon 8 inclusion to one-fourth (44.7% to 12.4%, FIG. 9B, lane 3). When both of these elements were mutated, DT-3 cell could no longer choose exon 8, and all splicing products were the exon 9 form (FIG. 9B, lane 4). These results indicate that DT-3 cell use both of these cis-elements to select exon 8 presumably by silencing the exon 9 via its 3' splice site.

Example 7

Regulatory Mechanism of Transacting Factors to Switch Exons

Figure 13:
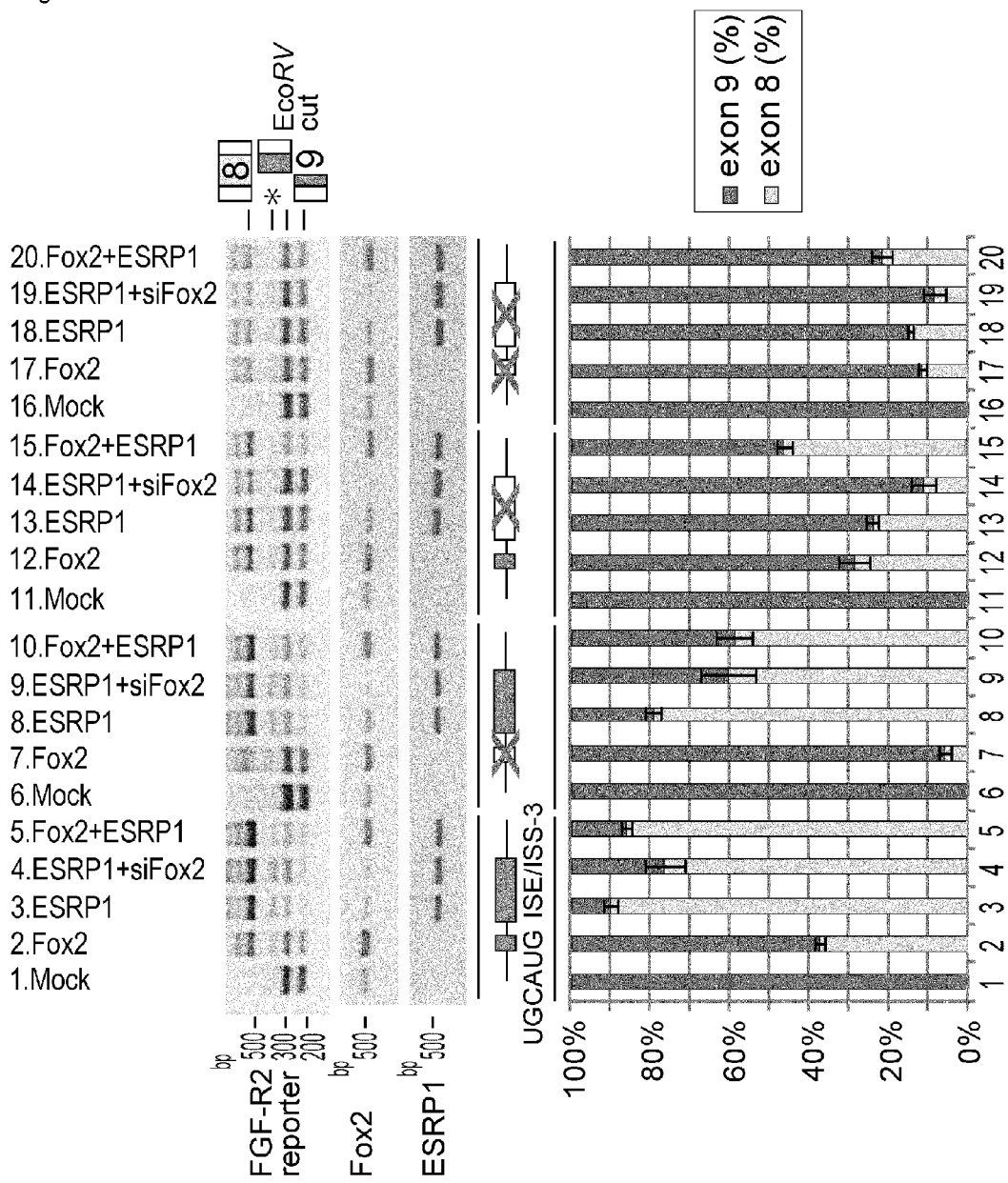
FIG. 13 shows Fox and ESRP which promote exon switching through repressing exon 9 via UGCAUG and ISE/ISS-3. RT-PCR from HeLa cell transfected the indicated wild-type or cis-mutated reporter vectors and Fox2 and/or ESRP1 expression vectors with or without Fox2 siRNA. When Fox2 was transfected with the UGCAUG site-mutated reporter, the promoting effect of Fox2 on exon 8 inclusion was lost (FIG. 13, lane 7). Overexpression of ESRP1 still promoted exon switching of the UGCAUG-mutated reporter, but the ratio of exon 8 selection was slightly reduced (FIG. 13, lane 8) in comparison with the wild-type reporter (FIG. 13, lane 3). To the contrary, when ISE/ISS-3 was mutated, the promotion effect of ESRP on the exon switching was significantly reduced (FIG. 13, lanes 13), and the effect of Fox2 remained (FIG. 13, lanes 12 and 15). When both UGCAUG and ISE/ISS-3 were mutated, neither Fox2 nor ESRP1 caused a drastic switching any more (FIG. 13, lane 16-20). The bar graph shows the amount of each splicing product, and is based on calculations from three independent experiments; the mean value for each splice product is show in the respective column, with an error bar showing the SD (standard error).

Results from FIG. 9 suggest that both UGCAUG and ISE/ISS-3 are necessary and sufficient for selecting exon 8. A previous study has shown that Fox2 promotes exon 8 inclusion through UGCAUG in intron 8 [Baraniak A P, et al., (2006) Mol Cell Biol 26: 1209-1222.]. Also, a recent study from cDNA library screening identified epithelial splicing regulatory protein ESRP1 and ESRP2, which mediate exon 8 inclusion through binding to ISE/ISS-3 [Warzecha C C, et al., (2009) Mol Cell 33: 591-601.]. The present inventors therefore examined whether Fox1, Fox2, ESRP1, and ESRP2 promote switching from exon 9 to exon 8. First, the present inventors examined and compared the expression levels of these RNA-binding proteins between AT-3 and DT-3 cells by RT-PCR. Fox2 was expressed in both cell lines at similar levels, whereas expression of Fox1 was undetectable (FIG. 9C), and both ESRP1 and ESRP2 were specifically expressed in epithelial type DT-3 cell (FIG. 9C). Considering the observation that both UGCAUG and ISE/ISS-3 are essential cis-elements for selecting exon 8 (FIG. 9B), broadly expressed Fox2 might cooperates with epithelial-specific ESRP1 and ESRP2 for exon 8 inclusion. To test this hypothesis, the present inventors transfected their FGFR2 splicing reporter with Fox1, Fox2, ESRP1, or ESRP2, or combinations of these into HeLa cell, which has non-epithelial cell character (FIG. 10A, lane 1). When Fox1 or Fox2 was introduced into HeLa cell, selection of exon 8 increased in a dose-depend manner and reached 10% (FIG. 10A, lanes 2-4) or 40% (FIG. 10A, lanes 5-7), respectively. When ESRP1 or ESRP2 was introduced, selection of exon 8 also increased in a dose-depend manner, and reached over 90% (FIG. 10A, lanes 8-10 and 15-17, respectively). As HeLa cell expresses endogenous Fox2 in a similar manner to AT-3 cell (FIG. 10A, lane 1), the present inventors introduced ESRP1 or ESRP2 under the Fox2 knockdown condition, and evaluated the cooperative effects of ESRP1 or ESRP2 with endogenous Fox2. The knockdown efficiency of Fox2 was more than 80% at the mRNA level (average 81.2%). Knockdown of endogenous Fox2 decreased the ratio of exon 8 selection promoted by ESRP1 or ESRP2, with a maximum reduction of 24% (35.1-11.0% FIG. 10A, lane 8 versus lane 11) or 23% (55.9-32.6%, lane 15 versus lane 18), respectively. When both Fox2 and ESRP1 were transfected, the ratios of exon 8 inclusion were similar to those obtained with a single transfection of ESRP1 (FIG. 10A, lanes 21-24). These results indicate that introduced ESRPs promote exon 8 inclusion with endogenous Fox2, suggesting that Fox2 and ESRPs cooperatively act together for exon 8 inclusion. These results were also confirmed by means of the fluorescence from the splicing reporter co-transfected with Fox1, Fox2, ESRP1, or ESRP2, or both Fox2 and ESRP1 (FIG. 10B). Overexpression of ESRP1 or ESRP2 changed the color from red to green, but Fox1 or Fox2 alone had a smaller effect on the color change. Co-transfection of Fox2 and ESRP1 gave the maximum effect on the color switching which reflected the switching of proteins coded by the mutually exclusive exons. The present inventors then tested whether exon switching by Fox2 and ESRP1 depends on UGCAUG and ISE/ISS-3 in intron 8. The present inventors performed overexpression study of Fox2 and/or ESRP1 on reporter vectors mutated on either UGCAUG, ISE/ISS-3, or both of them, and confirmed that exon switching caused by Fox and ESRPs depends on UGCAUG and ISE/ISS-3, respectively (FIG. 13). These results showed that Fox and ESRP cooperatively promote switching from exon 8 to 9 through the cis-elements of UGCAUG and ISE/ISS-3 located near exon 9.

Next, the present inventors tested whether Fox and/or ESRP cause switching from exon 9 to exon 8 through interruption of exon 9 recognition. The present inventors examined this under the in vitro splicing conditions using $^{32}$P-labeled RNA probe of exon 9 with introns containing UGCAUG and ISE/ISS-3 sites (FIG. 10C, top panel) and the exon 8 RNA probe of same stretches. When the exon 9 probe was crosslinked by UV irradiation after incubation with HeLa nuclear extract and separated by electrophoresis, shifted band by closslinking U1 and U2 was observed as overlap (FIG. 10C, lane 2, indicated by arrow), as same as FIG. 8C. However, in the exon 8 probe, only shifted band by U1 was observed (FIG. 10C, lane 8, indicated by arrow, and data not shown for RNaseH digestion), presumably due to its weaker 3' splice site. When recombinant Fox2 or ESRP1 protein was added with the exon 9 probe, shifted binds by U1 and U2 snRNA were decreased (FIG. 10C, lanes 4 and 5, respectively), and almost disappeared by addition of both Fox2 and ESRP1 proteins (FIG. 10C, lane 6). However, suppressive or activating effect of Fox2 or/and ESRP1 was not obvious with exon 8 probe (FIG. 10C, lanes 9-12). These data indicate that both Fox and ESRP interrupt exon 9 recognition in vitro. Combining results from FIG. 10 and FIG. 13 indicate that Fox and ESRP disrupt exon 9 recognition from its 3' splice site through UGCAUG and ISE/ISS-3, and promoted switching to exon 8. A model shown in FIG. 12A, Epithelial regulation could be proposed.

Example 8

Expression Profile of Fox and ESRP Coincide with Exon8-EGFP In Vivo

Figure 11:
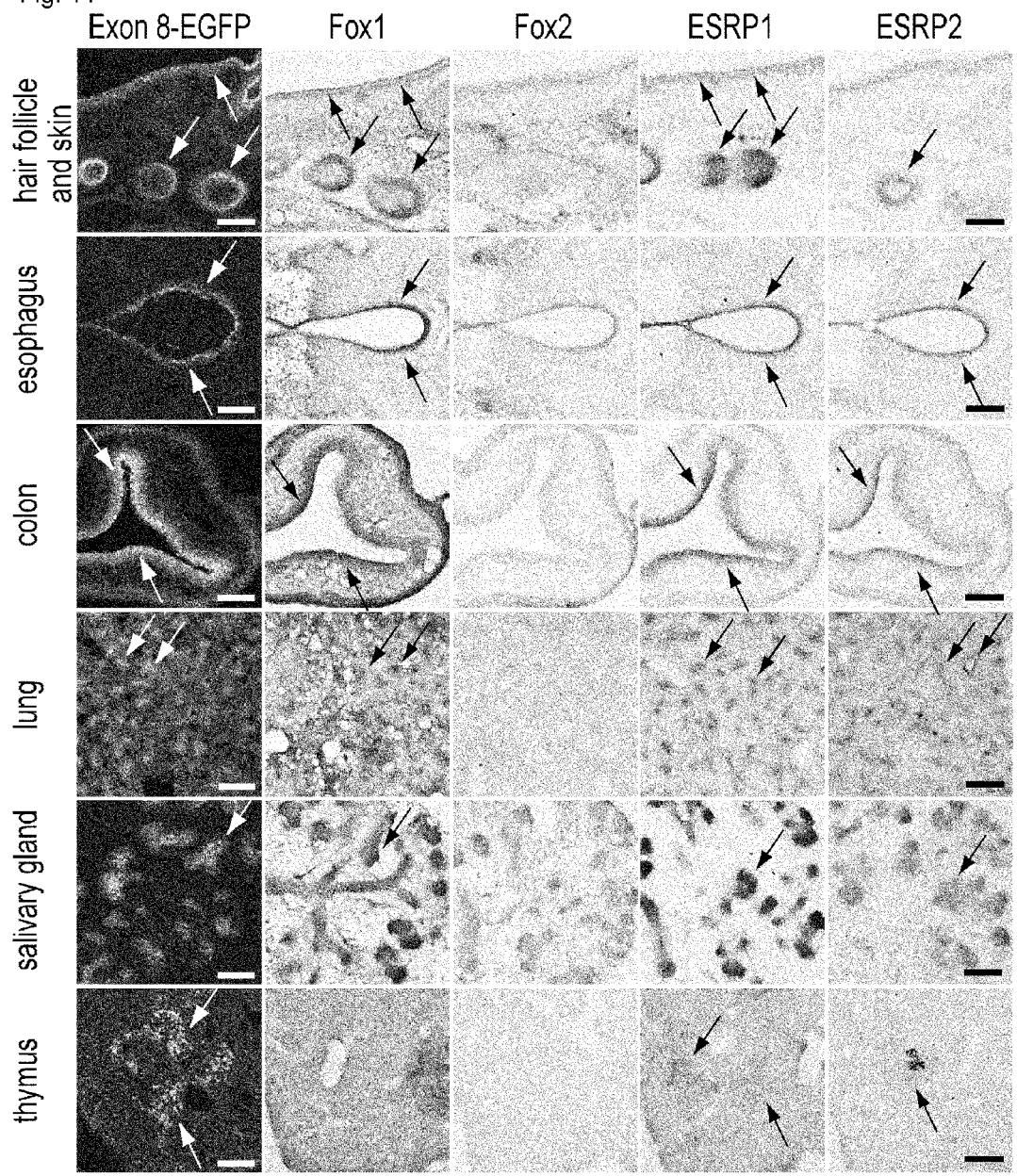
FIG. 11 shows the expression pattern of Foxs and ESRPs in splicing reporter mouse embryos. Sections from transgenic reporter embryos at E16.5. EGFP signal showed the exon 8 splicing pattern, and in situ hybridization was performed with indicated probes using serial sections. The EGFP signal is indicated by a white arrow. The violet signal, indicating mRNA localization, is shown by arrows, and nuclei were counterstained with Methyl Green (scale bar=100 micrometer).

In vitro study showed that disruption of exon 9 recognition from its 3' splice site by Fox and ESRP through UGCAUG and ISE/ISS-3 promoted switching to exon 8. Remaining question is whether the expression of Fox and ESRP coincides with the expression of exon 8 form in tissue-specific manner during development in vivo. The present inventors examined the expression profiles of Fox1, Fox2, ESRP1, and ESRP2 by in situ hybridization using the serial sections from their reporter transgenic mice embryos at E16.5 (FIG. 11). As the present inventors have already shown in FIG. 6D, the exon 8-EGFP expression was on left panels (as indicated by white arrows). In the in situ hybridization performed with adjacent sections, Fox1 mRNA was detected broadly throughout whole embryos at this stage, and its expression was overlapped with exon 8-EGFP signals localized in the epithelial tissues (indicated by black arrows). However, Fox2 was not detected in tissues where the EGFP signal was observed, whereas strong signal of Fox2 was detected in neuronal tissues and muscle in the same sections (data not shown). The expression of ESRP1 and ESRP2 was specifically detected in epithelial tissues (indicated by black arrows) and these expression almost completely overlapped with exon 8-EGFP signals during developing stage. These observations in vivo support an epithelial regulation model in FIG. 12A in which tissue specific factor ESRPs act together with generally expressed Fox family to promote exon 8 inclusion.

Example 9

Figure 14:
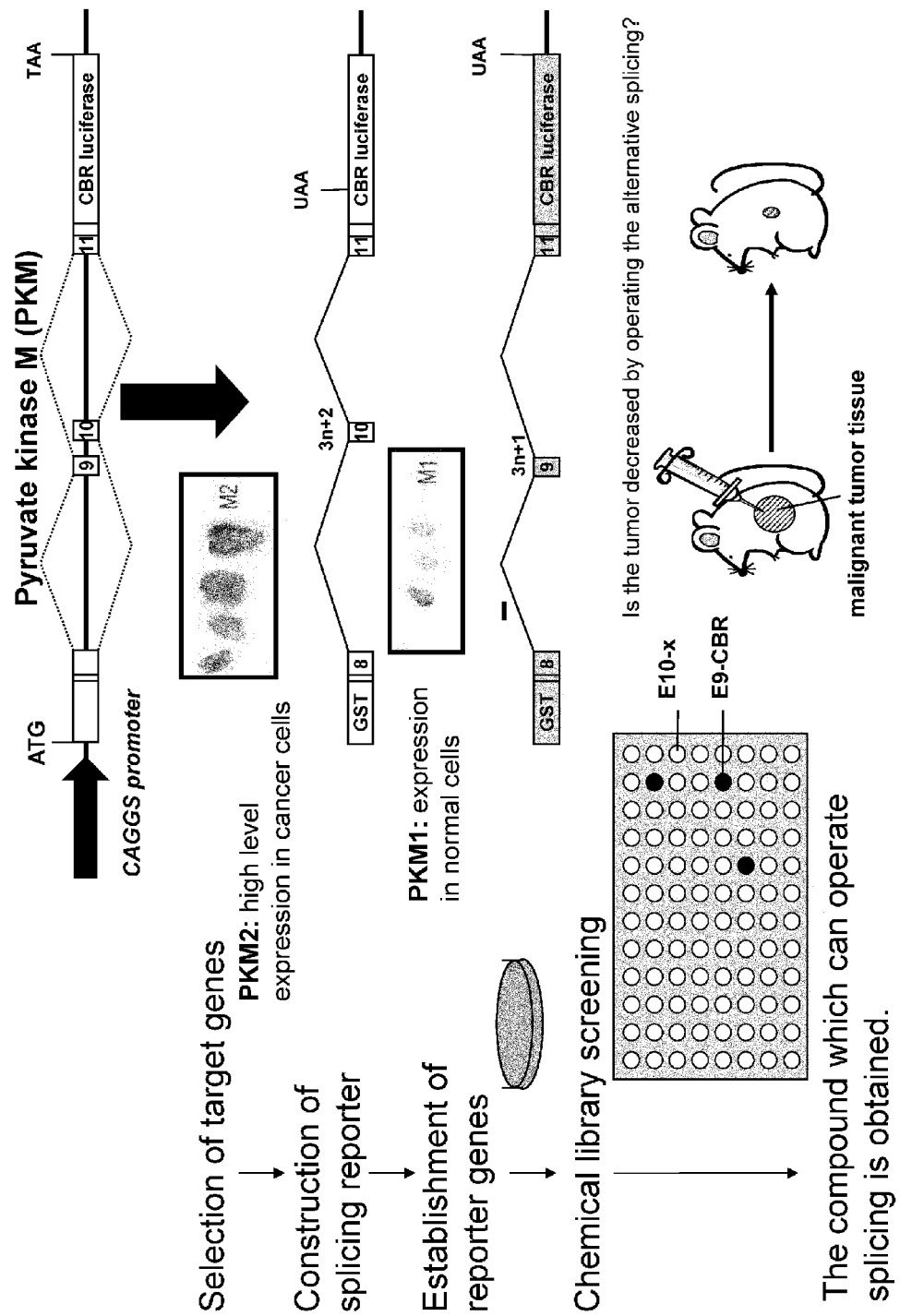
FIG. 14 shows a strategy for screening the compound which can operate alternative splicing.

A Method for Testing Whether or not a Compound to be Tested Affects an Alternative Splicing of a Specific Gene in a Mammalian Multicelluar Organism Strategy of a method for testing whether or not a compound to be tested affects an alternative splicing of a specific gene in a mammalian multicelluar organism is shown in FIG. 14.

The reporter proteins used for the method are GFP and FRP. Results of the method are shown in Tables 4-1 to 4-22. These results demonstrate that compounds that affect an alternative splicing of a specific gene have been actually isolated by the method of the present invention.

TABLE 4-1

| # | Location | Cat # | Name | CAS | MW | Conc | ID # | final conc. (µM, 50 ng/mL) | Number of cells | Ctrl number of cells | GFP/RFP (Ctrl = 1) |
|---|---|---|---|---|---|---|---|---|---|---|---|
| 272 | 4-D3 | GR-319 | Doxorubicin HCl | 25316-40-9 | 543.5 | 2 mg/ml | 66 | 9.199085655 | 18 | 5290 | 18.69526351 |
| 271 | 4-D2 | GR-318 | Daunorubicin HCl | 23541-50-6 | 527.5 | 2 mg/ml | 191 | 9.4780822 | 3 | 5290 | 11.83377412 |
| 263 | 4-C4 | GR-301 | Camptothecin | 7689-03-4 | 348.4 | 2 mg/ml | 288 | 14.35290557 | 385 | 5290 | 5.440752087 |
| 238 | 3-H9 | EI-206 | Auranofin | 34031-32-8 | 678.5 | 2 mg/ml | 758 | 7.369268658 | 1 | 4352 | 4.915173713 |
| 172 | 3-B3 | DL-548 | Idarubicin | 58957-92-9 | 497.5 | 2 mg/ml | 253 | 10.05012217 | 34 | 4352 | 4.863921716 |
| 408 | 6-A9 | DL-370 | Cytarabine | 147-94-4 | 243.2 | 2 mg/ml | 147 | 20.55743035 | 48 | 4303 | 4.588269745 |
| 267 | 4-C8 | GR-311 | Mitomycin c | 50-07-7 | 334.3 | 2 mg/ml | 387 | 14.95508196 | 319 | 5290 | 3.767284647 |
| 314 | 4-H5 | DL-215 | Gemcitabine HCl | 95058-81-4 | 263.2 | 2 mg/ml | 392 | 18.9967786 | 156 | 5290 | 3.517172864 |
| 407 | 6-A8 | DL-369 | Cyclocytidine HCl | 10212-25-6 | 225.2 | 2 mg/ml | 52 | 22.20192276 | 73 | 4303 | 3.416714729 |
| 441 | 6-E2 | DL-399 | 5-fluorouracil | 51-21-8 | 130.1 | 2 mg/ml | 42 | 38.43814737 | 433 | 4303 | 3.160858079 |
| 531 | 7-F2 | DL-488 | Quinacrine 2HCl dihydrate | 83-89-6 | 400.0 | 2 mg/ml | 604 | 12.50099852 | 5 | 4940 | 3.152823983 |
| 270 | 4-C11 | GR-316 | 10-hydroxycamptothecin | 64439-81-2 | 364.4 | 2 mg/ml | 13 | 13.72265719 | 541 | 5290 | 3.113545343 |
| 445 | 6-E6 | DL-403 | Floxuridine | 50-91-9 | 246.2 | 2 mg/ml | 152 | 20.30895444 | 142 | 4303 | 3.000014372 |
| 591 | 8-D2 | AC-1053 | Harmine | 442-51-3 | 212.3 | 2 mg/ml | 127 | 23.55674979 | 537 | 4361 | 2.851610014 |
| 484 | 7-A5 | DL-442 | Melphalan | 148-82-3 | 305.2 | 2 mg/ml | 247 | 16.38234506 | 483 | 4940 | 2.82837027 |
| 323 | 5-A4 | DL-103 | Clofarabine | 123318-82-1 | 303.7 | 2 mg/ml | 4 | 16.46457661 | 19 | 4930 | 2.692957739 |
| 492 | 7-B3 | DL-450 | Mitoxantrone 2HCl | 65271-80-9 | 444.5 | 2 mg/ml | 422 | 11.24880498 | 31 | 4940 | 2.65051939 |
| 490 | 7-A11 | DL-448 | Miconazole | 22916-47-8 | 416.1 | 2 mg/ml | 309 | 12.01527151 | 808 | 4940 | 2.531917074 |
| 493 | 7-B4 | T-104 | Taxol | 33069-62-4 | 853.9 | 2 mg/ml | 671 | 5.855288969 | 719 | 4940 | 2.454988842 |
| 617 | 8-F8 | PR-117 | Artesunate | 88495-63-0 | 384.4 | 2 mg/ml | 136 | 13.00626192 | 246 | 4361 | 2.378199382 |
| 318 | 4-H9 | DL-303 | Oxaliplatin | 61825-94-3 | 397.3 | 2 mg/ml | 524 | 12.58489202 | 825 | 5290 | 2.271403553 |
| 569 | 8-A10 | DL-518 | Topotecan | 123948-87-8 | 421.5 | 2 mg/ml | 698 | 11.86361043 | 259 | 4361 | 2.243826843 |
| 398 | 5-H9 | DL-360 | Clomiphene citrate | 50-41-9 | 406.0 | 2 mg/ml | 467 | 12.31611547 | 95 | 4930 | 2.163748878 |
| 264 | 4-C5 | GR-305 | Plicamycin | 18378-89-7 | 1085.2 | 2 mg/ml | 570 | 4.607568252 | 1070 | 5290 | 2.050967296 |
| 376 | 5-F7 | DL-338 | Bifonazole | 60628-96-8 | 310.4 | 2 mg/ml | 200 | 16.10813533 | 921 | 4930 | 1.99842226 |
| 166 | 3-A7 | AW8655 | Aclarubicin | 57576-44-0 | 811.9 | 2 mg/ml | 5 | 6.1584818C4 | 10 | 4352 | 1.998350103 |

Table 4-2 is a continuation of Table 4-1.

TABLE 4-2

| # | Location | Cat # | Name | CAS | MW | Conc | ID # | final conc. | Number of cells | Ctrl number of cells | GFP/RFP |
|---|---|---|---|---|---|---|---|---|---|---|---|
| 321 | 5-A2 | DL-545 | Mycophenolate mofetil | 128794-94-5 | 433.5 | 2 mg/ml | 11 | 11.5338652 | 500 | 4930 | 1.989012913 |
| 147 | 2-G8 | DL-208 | Sertaconazole | 99592-32-2 | 437.8 | 2 mg/ml | 657 | 11.42130487 | 1863 | 5627 | 1.988773841 |
| 412 | 6-B3 | DL-154 | Desloratadine | 100643-71-8 | 310.8 | 2 mg/ml | 291 | 16.08597995 | 231 | 4303 | 1.94912201 |
| 466 | 6-G7 | DL-424 | Imiquimod | 99011-02-6 | 240.3 | 2 mg/ml | 306 | 20.80642196 | 1944 | 4303 | 1.902330123 |
| 382 | 5-G3 | DL-344 | Carboplatin | 41575-94-4 | 337.2 | 2 mg/ml | 337 | 14.82789324 | 1373 | 4930 | 1.874549862 |
| 133 | 2-F4 | DL-250 | Docetaxil | 114977-28-5 | 807.9 | 2 mg/ml | 84 | 6.188883537 | 1194 | 5627 | 1.862180326 |
| 565 | 8-A6 | DL-515 | Tioconazole | 65899-73-2 | 387.7 | 2 mg/ml | 688 | 12.8959771 | 850 | 4361 | 1.840788999 |
| 52 | 1-F3 | AC-185 | Dobutamine HCl | 49745-95-1 | 301.4 | 2 mg/ml | 429 | 16.58986059 | 2991 | 5531 | 1.824866427 |
| 464 | 6-G5 | DL-422 | Idoxuridine | 54-42-2 | 354.1 | 2 mg/ml | 549 | 14.12019255 | 1924 | 4303 | 1.803725044 |
| 328 | 5-A9 | DL-156 | Lomustine | 13010-47-4 | 233.7 | 2 mg/ml | 375 | 21.39497185 | 1241 | 4930 | 1.797894151 |
| 582 | 8-C3 | DL-530 | Vidarabine | 5536-17-4 | 267.2 | 2 mg/ml | 726 | 18.70933923 | 1482 | 4361 | 1.71874095 |
| 475 | 6-H6 | DL-433 | Leflunomide | 75706-12-6 | 270.2 | 2 mg/ml | 176 | 18.50392577 | 1963 | 4303 | 1.707457571 |
| 389 | 5-G10 | DL-351 | Chlorambucil | 305-03-3 | 304.2 | 2 mg/ml | 330 | 16.43552673 | 841 | 4930 | 1.661670317 |
| 266 | 4-C7 | GR-307 | Etoposide | 33419-42-0 | 588.6 | 2 mg/ml | 367 | 8.495107735 | 055 | 5290 | 1.649456036 |
| 612 | 8-F3 | PD-195 | Zardaverine | 101975-10-4 | 268.2 | 2 mg/ml | 738 | 18.64128171 | 2744 | 4361 | 1.621688757 |

TABLE 4-2-continued

| | | | | | | | | | | |
|---|---|---|---|---|---|---|---|---|---|---|
| 195 3-D6 | CA-210 | Nifedipine | 21829-25-4 | 346.3 | 2 mg/ml | 573 | 14.43656359 | 156 | 4352 | 1.6143365 |
| 85 2-AG | AC-729 | Isoproterenol HCl (rac) | 51-30-9 | 211.3 | 2 mg/ml | 23 | 23.66717813 | 3953 | 5627 | 1.61359971 |
| 586 8-C7 | NH-101 | Astemizole | 68844-77-9 | 458.6 | 2 mg/ml | 137 | 10.90313098 | 38 | 4361 | 1.594859469 |
| 110 2-C11 | AC-810 | Norepinephrine-(+)-tartrate l (−) | 50-40-1 | 319.2 | 2 mg/ml | 741 | 15.66069709 | 4210 | 5627 | 1.593775287 |
| 202 3-E3 | CA-236 | Felodipine | 72509-76-3 | 384.2 | 2 mg/ml | 174 | 13.01194082 | 116 | 4352 | 1.579410212 |
| 570 8-A11 | DL-519 | Toremifene | 89778-26-7 | 406.0 | 2 mg/ml | 699 | 12.31611547 | 250 | 4361 | 1.574305192 |
| 553 7-H4 | DL-507 | Sulfadoxine | 2447-57-6 | 310.3 | 2 mg/ml | 660 | 16.11168465 | 2876 | 4940 | 1.545298551 |
| 108 2-C9 | AC-808 | Epinephrine-(+)-tartrate l (−) | 51-40-1 | 169.2 | 2 mg/ml | 159 | 29.55401164 | 4057 | 5627 | 1.528497942 |
| 416 6-B7 | DL-377 | Diethylstilbestrol | 56-53-1 | 268.4 | 2 mg/ml | 360 | 18.63176515 | 542 | 4303 | 1.524990903 |
| 370 5-E11 | DL-332 | Atracurium besylate | 64228-81-5 | 929.2 | 2 mg/ml | 145 | 5.381140881 | 3056 | 4930 | 1.520793417 |
| 8 1-A9 | A-249 | Mycophenolic acid | 24280-93-1 | 320.3 | 2 mg/ml | 481 | 15.60815539 | 1367 | 5531 | 1.512459974 |
| 273 4-D4 | GR336 | Tanshinone iia | 568-72-9 | 294.4 | 2 mg/ml | 668 | 16.98637805 | 2210 | 5290 | 1.504678809 |
| 469 6-G10 | DL-427 | Itraconazole | 84625-61-6 | 705.7 | 2 mg/ml | 29 | 7.085662585 | 344 | 4303 | 1.5046657 |
| 485 7-A6 | DL-443 | Methyldopa | 555-30-6 | 211.2 | 2 mg/ml | 579 | 23.67206688 | 3217 | 4940 | 1.501882352 |

Table 4-3 is a continuation of Table 4-2.

TABLE 4-3

| | | | | | | | | | | |
|---|---|---|---|---|---|---|---|---|---|---|
| 287 4-E8 | DL-297 | Bortezomib | 179324-69-7 | 384.2 | 2 mg/ml | 218 | 13.01248027 | 74 | 5290 | 1.496452459 |
| 435 6-D6 | DL-393 | Fenbendazole | 43210-67-9 | 299.4 | 2 mg/ml | 10 | 16.70264639 | 278 | 4303 | 1.49457566 |
| 158 2-H9 | AP-302 | Bleomycin sulfate | 9041-93-4 | 1415.6 | 2 mg/ml | 210 | 3.532131015 | 2702 | 5627 | 1.477092334 |
| 507 7-C8 | DL-464 | Oxiconazole nitrate | 64211-46-7 | 429.1 | 2 mg/ml | 529 | 11.65132316 | 2732 | 4940 | 1.459520403 |
| 418 6-B9 | DL-379 | Disulfiram | 97-77-8 | 296.5 | 2 mg/ml | 391 | 16.86111466 | 31 | 4303 | 1.442217134 |
| 549 7-G10 | DL-149 | Sparfloxacin | 110871-86-8 | 392.4 | 2 mg/ml | 624 | 12.74180798 | 3029 | 4940 | 1.44013786 |
| 522 7-E3 | DL-479 | Prednisolone | 50-24-8 | 360.5 | 2 mg/ml | 555 | 13.87138359 | 2900 | 4940 | 1.433017135 |
| 614 8-F5 | PG-051 | Misoprostol | 59122-46-2 | 382.5 | 2 mg/ml | 405 | 13.07035227 | 3052 | 4361 | 1.431648768 |
| 559 7-H10 | DL-512 | Tenoxicam | 59804-37-4 | 337.4 | 2 mg/ml | 676 | 14.82015798 | 2916 | 4940 | 1.429499751 |
| 530 7-E11 | DL-487 | Pyrantel pamoate | 22204-24-6 | 594.7 | 2 mg/ml | 602 | 8.407713573 | 2985 | 4940 | 1.406116379 |
| 635 8-H6 | DL-225 | Phenylpropanolamine | 14838-15-4 | 151.2 | 2 mg/ml | 542 | 33.066583 | 2551 | 4361 | 1.403544143 |
| 555 7-H6 | DL-509 | Sulfadimethoxine | 122-11-2 | 310.3 | 2 mg/ml | 659 | 16.11168465 | 3092 | 4940 | 1.399151769 |
| 225 3-G6 | EI-125 | Capsaicin | 404-86-4 | 305.4 | 2 mg/ml | 310 | 16.37085674 | 1918 | 4352 | 1.397969148 |
| 613 8-F4 | PG-006 PGE1 | Alprostadil | 745-65-3 | 354.5 | 2 mg/ml | 74 | 14.10473124 | 3505 | 4361 | 1.396557197 |
| 345 5-C6 | DL-175 | Tulobuterol | 41570-61-0 | 227.7 | 2 mg/ml | 717 | 21.95521172 | 3489 | 4930 | 1.391996805 |
| 342 5-C3 | DL-148 | Ricobendazole | 54029-12-8 | 281.3 | 2 mg/ml | 621 | 17.7723655 | 1381 | 4930 | 1.386396885 |
| 510 7-C11 | DL-467 | Oxibendazole | 20559-55-1 | 249.3 | 2 mg/ml | 528 | 20.05843825 | 786 | 4940 | 1.381170954 |
| 521 7-E2 | DL-478 | Pranoprofen | 52549-17-4 | 255.3 | 2 mg/ml | 409 | 19.58666189 | 3050 | 4040 | 1.364655602 |
| 540 7-F11 | ST-405 | Propranolol | 3506-09-0 | 259.4 | 2 mg/ml | 568 | 19.27887224 | 2641 | 4940 | 1.362604454 |
| 170 3-A11 | DL-270 | Ibudilast | 50847-11-5 | 230.3 | 2 mg/ml | 353 | 21.70964685 | 3018 | 4352 | 1.36174848 |
| 94 2-B5 | AC-748 | Apomorphine r (−) | 314-19-2 | 267.3 | 2 mg/ml | 495 | 18.70343733 | 3372 | 5627 | 1.356935081 |
| 560 7-H11 | DL-513 | Terazosin HCl | 63590-64-7 | 387.4 | 2 mg/ml | 677 | 12.90515076 | 3112 | 4940 | 1.355776526 |
| 509 7-C10 | DL-466 | Oxfendazole | 53716-50-0 | 315.4 | 2 mg/ml | 527 | 15.85523988 | 1712 | 4940 | 1.351521473 |
| 486 7-A7 | DL-444 | Methylprednisolone | 83-43-2 | 374.5 | 2 mg/ml | 202 | 13.35179798 | 3084 | 4940 | 1.347926167 |
| 286 4-E7 | PR-118 | Pentamidine | 100-33-4 | 340.4 | 2 mg/ml | 408 | 14.68736202 | 2694 | 5290 | 1.34452932 |
| 520 7-D11 | DL-477 | Pravastatin lactone | NA | 406.5 | 2 mg/ml | 591 | 12.29940198 | 2968 | 4940 | 1.341716934 |
| 544 7-G5 | DL-499 | Satafloxacin HCl | 91296-87-6 | 385.4 | 2 mg/ml | 647 | 12.97442308 | 3105 | 4940 | 1.340643527 |
| 536 7-F7 | DL-147 | Rebamipide | 90098-04-7 | 370.8 | 2 mg/ml | 612 | 13.48452543 | 2922 | 4940 | 1.337638677 |
| 511 7-D2 | DL-468 | Pantoprazole | 102625-70-7 | 383.4 | 2 mg/ml | 388 | 13.04201132 | 3112 | 4940 | 1.332777083 |

Table 4-4 is a continuation of Table 4-3.

TABLE 4-4

| | | | | | | | | | | |
|---|---|---|---|---|---|---|---|---|---|---|
| 498 7-B9 | DL-456 | Nefazodone | 83366-66-9 | 470.0 | 2 mg/ml | 72 | 10.63786579 | 2966 | 4940 | 1.321266691 |
| 245 4-A6 | EI-265 | Carbidopa | 28860-95-9 | 226.2 | 2 mg/ml | 336 | 22.10100264 | 3470 | 5290 | 1.316427838 |
| 48 1-E9 | AC-175 | Procaterol hcl | 62929-91-3 | 290.4 | 2 mg/ml | 561 | 17.21968607 | 4151 | 5531 | 1.312595792 |
| 630 8-G11 | DL-104 | Fulvestrant | 129453-61-8 | 606.8 | 2 mg/ml | 272 | 8.240142947 | 2156 | 4361 | 1.312106951 |
| 399 5-H10 | DL-361 | Clopidol | 2971-90-6 | 192.0 | 2 mg/ml | 476 | 26.03543715 | 3230 | 4930 | 1.310007746 |
| 10 1-A11 | A-275 | Rapamycin | 53123-88-9 | 914.2 | 2 mg/ml | 608 | 5.469279614 | 2046 | 5531 | 1.309221229 |
| 302 4-G3 | DL-222 | Alfacalcidol | 41294-56-8 | 400.7 | 2 mg/ml | 63 | 12.47970395 | 861 | 5290 | 1.301315546 |
| 624 8-G5 | DL-532 | Amprenavir | 161814-49-9 | 505.6 | 2 mg/ml | 101 | 9.888493393 | 2564 | 4361 | 1.2958728 |
| 49 1-E10 | AC-176 | Salbutamol sulfate | 51022-70-9 | 239.3 | 2 mg/ml | 643 | 20.89277153 | 4053 | 5531 | 1.29533558 |
| 355 5-D6 | DL-317 | 3'-azido-3'-deoxythymidine | 30516-87-1 | 267.2 | 2 mg/ml | 16 | 18.70933923 | 2356 | 4930 | 1.294443542 |
| 607 8-E8 | PD-175 | Rolipram | 61413-54-5 | 275.4 | 2 mg/ml | 635 | 18.15866292 | 2878 | 4361 | 1.29431941 |
| 558 7-H9 | DL-511 | Telmisartan | 144701-48-4 | 514.6 | 2 mg/ml | 673 | 9.71566806 | 3042 | 4940 | 1.290679894 |
| 609 8-E10 | PD180 | Trequinsin | 79855-88-2 | 405.5 | 2 mg/ml | 706 | 12.33042308 | 3009 | 4361 | 1.28875769 |
| 500 7-B11 | DL-458 | Norethindrone | 68-22-4 | 298.4 | 2 mg/ml | 163 | 16.75440277 | 3205 | 4940 | 1.288435074 |
| 381 5-G2 | DL-343 | Carbadox | 6804-07-5 | 262.2 | 2 mg/ml | 317 | 19.06746737 | 2293 | 4930 | 1.280857769 |
| 636 8-H7 | DL-234 | Succinylcholine | 306-40-1 | 290.4 | 2 mg/ml | 654 | 17.21726327 | 2727 | 4361 | 1.275426477 |
| 571 8-B2 | DL-520 | Tolfenamic acid | 13710-19-5 | 261.7 | 2 mg/ml | 695 | 19.10509883 | 2697 | 4361 | 1.274462393 |
| 34 1-D5 | AC-146 | Prazosin HCl | 19216-56-9 | 383.4 | 2 mg/ml | 554 | 13.0408592 | 2109 | 5531 | 1.27325226 |

TABLE 4-4-continued

| | | | | | | | | | | |
|---|---|---|---|---|---|---|---|---|---|---|
| 392 5-H3 | T-115 | Thaldomide | 50-35-1 | 258.2 | 2 mg/ml | 681 | 19.3621601 | 2622 | 4930 | 1.27114327 |
| 568 8-A9 | DL-188 | Tosufloxacin | 100490-36-6 | 404.4 | 2 mg/ml | 700 | 12.36547599 | 2590 | 4361 | 1.265839944 |
| 159 2-H10 | AR-100 | Bopindolol malonate | 62658-64-4 | 380.5 | 2 mg/ml | 215 | 13.14090804 | 3625 | 5627 | 1.26531707 |
| 298 4-F9 | DL-299 | Celecoxib | 169590-42-5 | 331.4 | 2 mg/ml | 328 | 13.11031018 | 3060 | 5290 | 1.262654116 |
| 461 6-G2 | DL-419 | Hydrocortisone | 50-23-7 | 362.5 | 2 mg/ml | 189 | 13.79423553 | 3105 | 4303 | 1.261714165 |
| 259 4-B10 | GR-100 | Retinoic acid | 302-73-4 | 300.4 | 2 mg/ml | 617 | 16.64198328 | 2697 | 5290 | 1.260341848 |
| 532 7-F3 | DL-489 | Quinapril HCl | 82586-55-8 | 438.5 | 2 mg/ml | 606 | 11.401774 | 3149 | 4940 | 1.258641379 |
| 625 8-G6 | DL-533 | Aprepitant | 170729-80-3 | 534.4 | 2 mg/ml | 118 | 9.35562882 | 2165 | 4361 | 1.253657712 |
| 502 7-C3 | DL-460 | Nystatin | 1400-61-9 | 926.1 | 2 mg/ml | 198 | 5.398878307 | 3293 | 4940 | 1.252683637 |
| 537 7-F8 | DL-492 | Ribavirin | 36791-04-5 | 244.2 | 2 mg/ml | 619 | 20.47429608 | 3140 | 4940 | 1.249983388 |
| 390 5-G11 | DL-352 | Chlorpheniramine maleate | 113-92-8 | 274.8 | 2 mg/ml | 365 | 18.19530057 | 3724 | 4930 | 1.2493157 |

Table 4-5 is a continuation of Table 4-4.

TABLE 4-5

| | | | | | | | | | | |
|---|---|---|---|---|---|---|---|---|---|---|
| 334 5-B5 | DL-309 | Octreotide | 83150-76-9 | 1019.3 | 2 mg/ml | 206 | 4.905513097 | 3742 | 4930 | 1.242156182 |
| 514 7-D5 | DL-471 | Pefloxacine mesylate | 149676-40-4 | 535 | 2 mg/ml | 535 | 14.99854589 | 3646 | 4940 | 1.236573794 |
| 86 2-A7 | AC-734 | Acetylcholine Cl | 60-31-1 | 146.2 | 2 mg/ml | 50 | 34.19713706 | 3490 | 5627 | 1.235291184 |
| 146 2-G7 | DL-262 | Atovaquone | 95233-18-4 | 366.8 | 2 mg/ml | 140 | 13.62962577 | 3754 | 5627 | 1.229980859 |
| 470 6-G11 | EI-288 | Ketoprofen (s) | 2216-88-5 | 254.3 | 2 mg/ml | 95 | 19.66273069 | 2780 | 4303 | 1.229222044 |
| 119 2-D10 | DL-124 | Vitamin a (acetate) | 68-26-8 | 328.5 | 2 mg/ml | 732 | 15.22074 | 3527 | 5627 | 1.228127881 |
| 296 4-F7 | DL-298 | Bexarotene | 153559-49-0 | 348.5 | 2 mg/ml | 181 | 14.34763211 | 3070 | 5290 | 1.224129173 |
| 425 6-C6 | DL-384 | Enrofloxacin | 93106-60-6 | 359.4 | 2 mg/ml | 135 | 13.9119251 | 3025 | 4303 | 1.223123525 |
| 357 5-D8 | PR-123 | Alendronate | 121268-17-5 | 248.1 | 2 mg/ml | 62 | 20.15394876 | 3185 | 4930 | 1.220700948 |
| 92 2-B3 | AC-746 | Tubocurarine Cl (+) | 57-94-3 | 609.7 | 2 mg/ml | 716 | 8.200093835 | 3433 | 5627 | 1.219635948 |
| 451 6-F2 | DL-409 | Ftorafur | 17902-23-7 | 200.2 | 2 mg/ml | 268 | 24.978652 | 2962 | 4303 | 1.218453142 |
| 127 2-E8 | AC-986 | Isoniazid | 54-85-3 | 137.1 | 2 mg/ml | 15 | 36.45851069 | 3759 | 5627 | 1.21783323 |
| 623 8-G4 | S-650 | Tamoxifen citrate | 54965-24-1 | 371.5 | 2 mg/ml | 666 | 13.45796739 | 2282 | 4361 | 1.215330405 |
| 447 6-E8 | DL-405 | Flubendazole | 31430-15-6 | 313.3 | 2 mg/ml | 153 | 15.9596163 | 409 | 4303 | 1.212383568 |
| 61 1-G2 | AC-221 | Telenzepine 2HCl | 147416-96-4 | 370.5 | 2 mg/ml | 672 | 13.49612212 | 3723 | 5531 | 1.210899438 |
| 144 2-G5 | DL-260 | Ractopamine | 97825-25-7 | 301.4 | 2 mg/ml | 607 | 16.58986059 | 3997 | 5627 | 1.209935549 |
| 634 8-H5 | DL-146 | Phloridzin | 60-81-1 | 436.4 | 2 mg/ml | 39 | 11.45686845 | 2768 | 4361 | 1.206731926 |
| 165 3-A6 | DL-223 | Cerivastatin | 145599-86-6 | 459.6 | 2 mg/ml | 329 | 10.8799016 | 108 | 4352 | 1.205442874 |
| 118 2-D9 | AC-858 | Naltriben mesylate | 111555-58-9 | 415.5 | 2 mg/ml | 489 | 12.03388405 | 3827 | 5627 | 1.203653932 |
| 99 2-B10 | AC-757 | Raclopride l-tartrate s(−) | 84225-95-6 | 347.2 | 2 mg/ml | 603 | 14.39908652 | 3519 | 5627 | 1.203305219 |
| 140 2-F11 | DL-256 | Lacidipine | 103890-78-4 | 455.6 | 2 mg/ml | 130 | 10.97559881 | 3439 | 5627 | 1.20137176 |
| 128 2-E9 | AC-993 | Ticlopidine HCl | 53885-35-1 | 263.8 | 2 mg/ml | 685 | 18.9543722 | 3369 | 5627 | 1.201082388 |
| 602 8-E3 | PD-125 | Cilostamide | 68550-75-4 | 342.4 | 2 mg/ml | 373 | 14.6010204 | 2851 | 4361 | 1.199961281 |
| 528 7-E9 | DL-485 | Primaquine phosphate | 63-45-6 | 259.4 | 2 mg/ml | 592 | 19.27866039 | 3270 | 4940 | 1.198460584 |
| 506 7-C7 | DL-463 | Oxcarbazepine | 28721-07-5 | 252.3 | 2 mg/ml | 526 | 19.81963419 | 3556 | 4940 | 1.198397854 |
| 160 2-H11 | AR-102 | Guanfacine HCl | 29520-14-7 | 282.6 | 2 mg/ml | 8 | 17.69544755 | 3849 | 5627 | 1.197498136 |
| 261 4-C2 | GR-211 | Bezafibrate | 41859-67-0 | 361.8 | 2 mg/ml | 183 | 13.81869949 | 3845 | 5290 | 1.195438873 |
| 556 7-H7 | DL-510 | Sulfasalazine | 599-79-1 | 398.4 | 2 mg/ml | 661 | 12.55019824 | 3292 | 4940 | 1.192301974 |
| 482 7-A3 | DL-440 | Medroxyprogesterone 17-acetate | 98-92-0 | 122.1 | 2 mg/ml | 144 | 40.94081334 | 3282 | 4940 | 1.191977459 |
| 380 5-F11 | DL-342 | Canrenone | 976-71-6 | 340.5 | 2 mg/ml | 299 | 14.68572576 | 3703 | 4930 | 1.190307786 |

Table 4-6 is a continuation of Table 4-5.

TABLE 4-6

| | | | | | | | | | | |
|---|---|---|---|---|---|---|---|---|---|---|
| 439 6-D10 | DL-397 | Fenofibrate | 49562-28-9 | 360.8 | 2 mg/ml | 35 | 13.85651967 | 2923 | 4303 | 1.189725982 |
| 547 7-G8 | DL-502 | Secnidazole | 3366-95-8 | 185.2 | 2 mg/ml | 653 | 27.00016989 | 3233 | 4940 | 1.188643076 |
| 444 6-E5 | DL-402 | Florfenicol | 73231-34-2 | 358.2 | 2 mg/ml | 151 | 13.95797778 | 2867 | 4303 | 1.187670804 |
| 638 8-H9 | DL-540 | L-thyroxine [(3-[4-(4-hydroxy-3,5-diiodophenoxy)-3,5-diiodophenyl]-l-alanine] | 51-48-9 | 776.9 | 2 mg/ml | 747 | 6.436026756 | 2477 | 4361 | 1.183555403 |
| 481 7-A2 | DL-439 | Mebendazol | 31431-39-7 | 295.3 | 2 mg/ml | 75 | 16.93191585 | 572 | 4940 | 1.176735236 |
| 254 4-B5 | G-233 | Mevastatin | 73573-88-3 | 390.5 | 2 mg/ml | 297 | 12.80329633 | 1633 | 5290 | 1.176328614 |
| 93 2-B4 | AC-747 | Butaclamol (+) | 55528-07-9 | 361.5 | 2 mg/ml | 261 | 13.83003747 | 3384 | 5627 | 1.175993589 |
| 515 7-D6 | DL-472 | Penciclovir | 39809-25-1 | 253.3 | 2 mg/ml | 536 | 19.74234269 | 3564 | 4940 | 1.174629247 |
| 268 4-C9 | GR-312 | Puromycin 2HCl | 58-58-2 | 471.5 | 2 mg/ml | 600 | 10.60399665 | 42 | 5290 | 1.173417452 |
| 359 5-D10 | DL321 | Albendazole | 54965-21-8 | 265.3 | 2 mg/ml | 61 | 18.84401396 | 504 | 4930 | 1.166836827 |
| 142 2-G3 | G-226 | Lovastatin | 75330-75-5 | 404.6 | 2 mg/ml | 582 | 12.35936525 | 1348 | 5627 | 1.16576373 |
| 134 2-F5 | DL-251 | Olopatadine | 113806-05-6 | 337.4 | 2 mg/ml | 246 | 14.81822366 | 3388 | 5627 | 1.164020602 |
| 234 3-H5 | EI-166 | Debrisoquin sulfate | 581-88-4 | 175.2 | 2 mg/ml | 214 | 28.53307848 | 3765 | 4352 | 1.162466552 |
| 535 7-F6 | DL-491 | Ramipril | 87333-19-5 | 416.5 | 2 mg/ml | 611 | 12.00417102 | 3358 | 4940 | 1.16242813 |
| 533 7-F4 | DL-159 | Racecadotril | 81110-73-8 | 385.5 | 2 mg/ml | 597 | 12.97064774 | 3502 | 4940 | 1.160386252 |
| 303 4-G4 | DL-151 | Anethole-trithione (anetholtrithion) | 532-11-6 | 240.4 | 2 mg/ml | 110 | 20.80155376 | 2915 | 5290 | 1.158201623 |
| 603 8-E4 | PD-130 | Etazolate | 51022-77-6 | 289.3 | 2 mg/ml | 303 | 17.28071797 | 2866 | 4361 | 1.157947621 |
| 562 8-A3 | DL-169 | Tenatoprazole | 113712-98-4 | 346.4 | 2 mg/ml | 675 | 14.43372763 | 2969 | 4361 | 1.157672912 |

TABLE 4-6-continued

| | | | | | | | | | | |
|---|---|---|---|---|---|---|---|---|---|---|
| 518 | 7-D9 | DL-475 | Phenylbutazone | 50-33-9 | 308.4 | 2 mg/ml | 541 | 16.21358085 | 3490 | 4940 | 1.15747637 |
| 554 | 7-H5 | DL-508 | Sulfadiazine | 68-35-9 | 250.3 | 2 mg/ml | 658 | 19.9775612 | 3242 | 4940 | 1.157101921 |
| 443 | 6-E4 | DL-401 | Fleroxacin | 79660-72-3 | 369.3 | 2 mg/ml | 121 | 13.53742316 | 3292 | 4303 | 1.155032763 |
| 405 | 6-A6 | DL-367 | Cyclophosphamide monohydrate | 6055-19-2 | 261.1 | 2 mg/ml | 54 | 19.15051385 | 3065 | 4303 | 1.153475869 |
| 616 | 8-F7 | PI-153 | Cilastatin | 82009-34-5 | 358.5 | 2 mg/ml | 371 | 13.94855694 | 2885 | 4361 | 1.15300352 |
| 236 | 3-H7 | EI-168 | Bumetanide | 28395-03-1 | 364.4 | 2 mg/ml | 27 | 13.72030634 | 2977 | 4352 | 1.151305133 |
| 495 | 7-B6 | DL-453 | Nadifloxacin | 124858-35-1 | 360.4 | 2 mg/ml | 484 | 13.873912 | 3397 | 4940 | 1.150950193 |
| 152 | 2-H3 | DL-200 | Dorzolamide | 120279-95-0 | 324.4 | 2 mg/ml | 270 | 15.41107406 | 3803 | 5627 | 1.149226768 |

Table 4-7 is a continuation of Table 4-6.

TABLE 4-7

| | | | | | | | | | | |
|---|---|---|---|---|---|---|---|---|---|---|
| 611 | 8-F2 | PD-190 | Zaprinast | 37762-06-4 | 271.3 | 2 mg/ml | 737 | 18.43108283 | 2941 | 4361 | 1.147348515 |
| 529 | 7-E10 | DL-486 | Praziquantel | 55268-74-1 | 312.4 | 2 mg/ml | 553 | 16.00433628 | 2885 | 4940 | 1.145953739 |
| 575 | 8-B6 | DL-524 | Triamcinolone | 124-94-7 | 394.4 | 2 mg/ml | 707 | 12.67606612 | 2580 | 4361 | 1.143977924 |
| 377 | 5-F8 | DL-339 | Bisacodyl | 603-50-9 | 361.4 | 2 mg/ml | 207 | 13.83504635 | 3324 | 4930 | 1.143483143 |
| 422 | 6-C3 | DL-381 | Doxycycline HCl | 24390-14-5 | 444.4 | 2 mg/ml | 94 | 11.24998138 | 3267 | 4303 | 1.142311586 |
| 111 | 2-D2 | DL-557 | Quetiapine fumarate | 111974-72-2 | 883.1 | 2 mg/ml | 751 | 5.66183012 | 3666 | 5627 | 1.139672188 |
| 513 | 7-D4 | DL-470 | Pazufloxacin | 127045-41-4 | 318.3 | 2 mg/ml | 393 | 15.70808842 | 3492 | 4940 | 1.136211888 |
| 517 | 7-D8 | DL-474 | Pencillin v potassium | 132-98-9 | 349.4 | 2 mg/ml | 537 | 14.31072575 | 3442 | 4940 | 1.13425101 |
| 457 | 6-F8 | DL-415 | Gliclazide | 21187-98-4 | 323.4 | 2 mg/ml | 433 | 15.4599209 | 3316 | 4303 | 1.133895534 |
| 329 | 5-A10 | DL-543 | Iloprost | 78919-13-8 | 360.5 | 2 mg/ml | 359 | 13.86970478 | 3838 | 4930 | 1.132367656 |
| 525 | 7-E6 | DL-482 | Prothionamide | 14222-60-7 | 180.3 | 2 mg/ml | 598 | 27.73565195 | 5562 | 4940 | 1.132043112 |
| 69 | 1-G10 | AC-277 | Mepyramine maleate | 59-33-6 | 285.4 | 2 mg/ml | 452 | 17.51974019 | 3548 | 5531 | 1.131255358 |
| 579 | 8-B10 | DL-527 | Valaciclovir | 124832-27-5 | 324.3 | 2 mg/ml | 719 | 15.41581937 | 2836 | 4361 | 1.130813555 |
| 459 | 6-F10 | DL-417 | Guaifenesin | 93-14-1 | 198.2 | 2 mg/ml | 51 | 25.2244115 | 3239 | 4303 | 1.129530166 |
| 620 | 8-F11 | S-510 | Mifepristone | 84371-65-3 | 429.6 | 2 mg/ml | 316 | 11.63852239 | 1878 | 4361 | 1.12949478 |
| 534 | 7-F5 | DL-490 | Ranolazine 2HCl | 95635-56-6 | 427.5 | 2 mg/ml | 601 | 11.69458488 | 3509 | 4940 | 1.127775031 |
| 76 | 1-H7 | DL-560 | zolmitriptan | 139264-17-8 | 320.4 | 2 mg/ml | 461 | 16.4794763 | 3765 | 5531 | 1.127507134 |
| 476 | 6-H7 | DL-434 | Lisinopril | 83915-83-7 | 405.5 | 2 mg/ml | 302 | 12.33050731 | 3244 | 4303 | 1.127147071 |
| 197 | 3-D8 | CA-212 | Nitrendipine | 39562-70-4 | 360.4 | 2 mg/ml | 508 | 13.8746327 | 2606 | 4352 | 1.126633527 |
| 185 | 3-C6 | PG-008 | Dinoprost | 551-11-1 | 354.5 | 2 mg/ml | 141 | 14.10473124 | 3656 | 4352 | 1.125552615 |
| 255 | 4-B6 | G-244 | Simvastatin | 79902-63-9 | 418.6 | 2 mg/ml | 638 | 11.94518755 | 933 | 5290 | 1.124603165 |
| 541 | 7-G2 | DL-496 | Roxatidine acetate HCl | 93793-83-0 | 348.4 | 2 mg/ml | 637 | 14.34942532 | 3592 | 4940 | 1.123767026 |
| 332 | 5-B3 | DL-167 | Meropenem | 96036-03-2 | 383.5 | 2 mg/ml | 458 | 13.03883303 | 3402 | 4930 | 1.119846063 |
| 347 | 5-C8 | DL-220 | Vindesine | 53643-48-4 | 753.9 | 2 mg/ml | 729 | 6.631765014 | 653 | 4930 | 1.117956962 |
| 206 | 3-E7 | DL-218 | Denbufylline | 57076-71-8 | 320.4 | 2 mg/ml | 283 | 15.60575226 | 3308 | 4352 | 1.117337902 |
| 289 | 4-E10 | DL-186 | Fentiazac | 18046-21-4 | 329.8 | 2 mg/ml | 107 | 15.16034996 | 2880 | 5290 | 1.117182769 |
| 368 | 5-E9 | NP-016 | Artemisinin | 63968-64-9 | 282.3 | 2 mg/ml | 134 | 17.70917072 | 2662 | 4930 | 1.116460589 |
| 639 | 8-H10 | DL-136 | Cyproheptadine | 129-03-3 | 287.4 | 2 mg/ml | 119 | 17.39685803 | 2204 | 4361 | 1.115155722 |
| 115 | 2-D6 | AC-834 | Mesulergine HCl | 64795-35-3 | 362.5 | 2 mg/ml | 473 | 13.79319781 | 3333 | 5627 | 1.11434003 |
| 365 | 5-E6 | DL-327 | Ampicillin trihydrate | 7177-48-2 | 349.4 | 2 mg/ml | 100 | 14.30977392 | 3186 | 4930 | 1.113993115 |

Table 4-8 is a continuation of Table 4-7.

TABLE 4-8

| | | | | | | | | | | |
|---|---|---|---|---|---|---|---|---|---|---|
| 631 | 8-H2 | DL-538 | Methysergide | 361-37-5 | 353.5 | 2 mg/ml | 208 | 14.14554247 | 2749 | 4361 | 1.113161115 |
| 313 | 4-H4 | DL-155 | Fosinopril | 98048-97-6 | 563.7 | 2 mg/ml | 267 | 8.870321611 | 3091 | 5290 | 1.11308584 |
| 203 | 3-E4 | CA-237 | Cilnidipine | 132203-70-4 | 492.5 | 2 mg/ml | 372 | 10.1515956 | 2863 | 4352 | 1.112274868 |
| 618 | 8-F9 | RA-104 | Picotamide | 32828-81-2 | 376.4 | 2 mg/ml | 92 | 13.28308608 | 2800 | 4361 | 1.110016418 |
| 505 | 7-C6 | DL-462 | Omeprazole | 73590-58-6 | 345.4 | 2 mg/ml | 521 | 14.47499427 | 3182 | 4940 | 1.109359452 |
| 494 | 7-B5 | DL-452 | Myclobutanil | 88671-89-0 | 288.8 | 2 mg/ml | 468 | 17.31406615 | 3430 | 4940 | 1.108435718 |
| 497 | 7-B8 | DL-455 | Naphazoline HCl | 835-31-4 | 210.3 | 2 mg/ml | 491 | 23.77769793 | 3265 | 4940 | 1.108363804 |
| 64 | 1-G5 | AC-238 | Ivermectin | 70288-86-7 | 875.1 | 2 mg/ml | 48 | 5.713524477 | 2997 | 5531 | 1.107715952 |
| 615 | 8-F6 | PI-146 | Argatroban | 74863-84-6 | 508.6 | 2 mg/ml | 122 | 9.830046942 | 2317 | 4361 | 1.105957455 |
| 552 | 7-H3 | DL-506 | Streptomycin sulfate | 3810-74-0 | 581.6 | 2 mg/ml | 650 | 8.597200325 | 3447 | 4940 | 1.104239856 |
| 467 | 6-G8 | DL-425 | Indapamide | 26807-65-8 | 365.8 | 2 mg/ml | 318 | 13.66713133 | 3873 | 4303 | 1.104220554 |
| 387 | 5-G8 | DL-349 | Chloramphenicol | 56-75-7 | 323.1 | 2 mg/ml | 331 | 15.47342379 | 3620 | 4930 | 1.103062547 |
| 155 | 2-H6 | DL-119 | Sodium phenylacetate | 114-70-5 | 158.1 | 2 mg/ml | 752 | 31.61883569 | 3644 | 5627 | 1.102851143 |
| 604 | 8-E5 | PD-140 | Isobutylmethylxanthine | 28822-58-4 | 222.2 | 2 mg/ml | 271 | 22.49732147 | 3315 | 4361 | 1.100601762 |
| 191 | 3-D2 | C-115 | Galanthamine HBr | 1953-04-4 | 287.4 | 2 mg/ml | 348 | 17.39966708 | 3008 | 4352 | 1.100168157 |
| 131 | 2-F2 | DL-248 | Vardenafil | 224785-90-4 | 488.6 | 2 mg/ml | 721 | 10.23304135 | 3824 | 5627 | 1.09750532 |
| 627 | 8-G8 | DL-535 | Efavirenz | 154598-52-4 | 315.7 | 2 mg/ml | 87 | 15.83874736 | 2950 | 4361 | 1.096621218 |
| 610 | 8-E11 | PD-185 | Vinpocetine | 42971-09-5 | 350.5 | 2 mg/ml | 731 | 14.26677127 | 2743 | 4361 | 1.095654486 |
| 375 | 5-F6 | DL-337 | Betamethasone | 378-44-9 | 504.6 | 2 mg/ml | 177 | 9.908813352 | 3147 | 4930 | 1.095188192 |
| 480 | 6-H11 | DL-438 | Losartan potassium | 124750-99-8 | 461.0 | 2 mg/ml | 442 | 10.84562844 | 2989 | 4303 | 1.094220605 |
| 503 | 7-C4 | DL-461 | Ofloxacin | 82419-36-1 | 361.4 | 2 mg/ml | 515 | 13.83599695 | 3273 | 4940 | 1.091241177 |
| 367 | 5-E8 | DL-329 | Apramycin | 37321-09-8 | 539.6 | 2 mg/ml | 117 | 9.266332216 | 3565 | 4930 | 1.091102994 |
| 632 | 8-H3 | DL-107 | Esmolol | 81147-92-4 | 295.4 | 2 mg/ml | 217 | 16.92723608 | 2801 | 4361 | 1.090858491 |
| 226 | 3-G7 | EI-126 | Dexamethasone | 50-02-2 | 392.5 | 2 mg/ml | 551 | 12.73976785 | 2885 | 4352 | 1.090773207 |
| 593 | 8-D4 | NS-107 | Dibenzepine HCl | 315-80-0 | 295.4 | 2 mg/ml | 342 | 16.92691402 | 2911 | 4361 | 1.090214969 |

TABLE 4-8-continued

| 219 | 3-F10 | D-111 | Remoxipride | 73220-03-8 | 371.3 | 2 mg/ml | 615 | 13.4670228 | 3102 | 4352 | 1.089515817 |
| 231 | 3-H2 | EI-160 | Clofibrate | 637-07-0 | 242.7 | 2 mg/ml | 466 | 20.6011795 | 3202 | 4352 | 1.088970447 |
| 82 | 2-A3 | AC-615 | Aminophylline | 317-34-0 | 180.2 | 2 mg/ml | 86 | 27.75196691 | 3411 | 5627 | 1.086250792 |
| 577 | 8-B8 | DL-158 | Tropisetron HCl | 105826-92-4 | 284.4 | 2 mg/ml | 715 | 17.58327395 | 2870 | 4361 | 1.085917732 |
| 100 | 2-B11 | AC-758 | Risperidone | 106266-06-2 | 410.5 | 2 mg/ml | 622 | 12.18039734 | 3677 | 5627 | 1.085610636 |

Table 4-9 is a continuation of Table 4-8.

TABLE 4-9

| 583 | 8-C4 | DL-531 | Iproniazid | 54-92-2 | 179.2 | 2 mg/ml | 1 | 27.89813343 | 2950 | 4361 | 1.083649788 |
| 112 | 2-D3 | AC-812 | Alprenolol HCl | 13707-88-5 | 249.4 | 2 mg/ml | 69 | 20.05164823 | 4059 | 5627 | 1.08286273 |
| 90 | 2-A11 | AC-743 | Neostigmine Br | 114-80-7 | 223.3 | 2 mg/ml | 496 | 22.39165941 | 3700 | 5627 | 1.081134642 |
| 132 | 2-F3 | DL-249 | Linezolid | 165800-03-3 | 337.4 | 2 mg/ml | 289 | 14.82123076 | 4094 | 5627 | 1.079830943 |
| 637 | 8-H8 | DL-195 | Trifluperidol 2HCl | 749-13-3 | 409.4 | 2 mg/ml | 709 | 12.21216805 | 2668 | 4361 | 1.076621099 |
| 361 | 5-E2 | GR-341 | Amifostine | 20537-88-6 | 214.2 | 2 mg/ml | 79 | 23.339979 | 3793 | 4930 | 1.075525552 |
| 196 | 3-D7 | CA-211 | Nimodipine | 66085-59-4 | 418.5 | 2 mg/ml | 142 | 11.94884261 | 3551 | 4352 | 1.074048725 |
| 633 | 8-H4 | DL-123 | Pantothenic acid | 79-83-4 | 219.2 | 2 mg/ml | 533 | 22.80610514 | 3095 | 4361 | 1.073870397 |
| 109 | 2-C10 | AC-809 | Xylazine HCl | 7361-61-7 | 220.3 | 2 mg/ml | 734 | 22.69233478 | 4024 | 5627 | 1.073498572 |
| 139 | 2-F10 | DL-255 | Nisoldipine | 63675-72-9 | 388.4 | 2 mg/ml | 505 | 12.8725284 | 2492 | 5627 | 1.072692413 |
| 224 | 3-G5 | EI-121 | Disodium cromoglycate | 15826-37-6 | 512.3 | 2 mg/ml | 746 | 9.759124699 | 3238 | 4352 | 1.072562348 |
| 184 | 3-C5 | NS-520 | Melatonin | 73-31-4 | 232.3 | 2 mg/ml | 187 | 21.52531202 | 3303 | 4352 | 1.068565791 |
| 182 | 3-C3 | DL-279 | Eriotinib | 183321-74-6 | 393.4 | 2 mg/ml | 196 | 12.70821424 | 2238 | 4352 | 1.068469754 |
| 524 | 7-E5 | DL-481 | Procarbazine HCl | 366-70-1 | 221.3 | 2 mg/ml | 560 | 22.59328122 | 3374 | 4940 | 1.067668516 |
| 360 | 5-D11 | DL-565 | Sumatriptan Succinate | 103628-48-4 | 413.5 | 2 mg/ml | 76 | 12.092004 | 3805 | 4930 | 1.067073547 |
| 7 | 1-A8 | A245 | Lomofungin | 26786-84-5 | 314.3 | 2 mg/ml | 349 | 15.91055721 | 2581 | 5531 | 1.066595684 |
| 50 | 1-E11 | AC-181 | Pindolol | 13523-86-9 | 248.3 | 2 mg/ml | 125 | 20.13468493 | 3750 | 5531 | 1.066333474 |
| 369 | 5-E10 | AC-166 | Atenolol | 29122-68-7 | 266.3 | 2 mg/ml | 138 | 18.77278265 | 3690 | 4930 | 1.065359701 |
| 460 | 6-F11 | DL-418 | Hexestrol | 84-16-2 | 270.4 | 2 mg/ml | 161 | 18.49284497 | 2460 | 4303 | 1.065264184 |
| 344 | 5-C5 | DL-143 | Thiamphenicol glycinate | 2393-92-2 | 413.3 | 2 mg/ml | 682 | 12.098354 | 3596 | 4930 | 1.063868092 |
| 578 | 8-B9 | DL-526 | Tylosin tartrate | 1405-54-5 | 902.1 | 2 mg/ml | 718 | 5.542647346 | 3044 | 4361 | 1.060390264 |
| 248 | 4-A9 | EI-292 | Meloxicam | 71125-38-7 | 351.4 | 2 mg/ml | 242 | 14.22858003 | 3513 | 5290 | 1.059662941 |
| 400 | 5-H11 | AC-1290 | Clopidogrel sulfate | 135046-48-9 | 321.8 | 2 mg/ml | 543 | 15.5362289 | 3664 | 4930 | 1.058515136 |
| 601 | 8-E2 | NS-835 | Thioridazine HCl | 130-61-0 | 370.6 | 2 mg/ml | 683 | 13.49226247 | 445 | 4361 | 1.057956033 |
| 483 | 7-A4 | DL-441 | Mefenamic acid | 61-68-7 | 241.3 | 2 mg/ml | 149 | 20.72175532 | 3395 | 4940 | 1.057893663 |
| 608 | 8-E9 | PD-179 | Siguazodan | 115344-47-3 | 284.3 | 2 mg/ml | 628 | 17.58561963 | 3294 | 4361 | 1.054481673 |
| 424 | 6-C5 | DL-383 | Enoxacin | 74011-58-8 | 320.3 | 2 mg/ml | 120 | 15.60909141 | 3281 | 4303 | 1.053050564 |
| 403 | 6-A4 | DL-365 | Corticosterone | 50-22-6 | 346.5 | 2 mg/ml | 43 | 14.43122849 | 3458 | 4303 | 1.051696556 |
| 371 | 5-F2 | DL-333 | Azaperone | 1649-18-9 | 327.4 | 2 mg/ml | 150 | 15.27160131 | 3623 | 4930 | 1.051506984 |

Table 4-10 is a continuation of Table 4-9.

TABLE 4-10

| 98 | 2-B9 | AC-755 | Pergolide mesylate | 66104-23-2 | 314.5 | 2 mg/ml | 415 | 15.89842964 | 3183 | 5627 | 1.051117975 |
| 83 | 2-A4 | AC-626 | Furafylline | 80288-49-9 | 260.3 | 2 mg/ml | 292 | 19.2119681 | 3300 | 5627 | 1.047879978 |
| 51 | 1-F2 | AC-183 | Cimaterol | 54239-37-1 | 219.3 | 2 mg/ml | 374 | 22.80098312 | 4584 | 5531 | 1.047417124 |
| 307 | 4-G8 | DL-102 | Clindamycin palmitate | 24729-96-2 | 425.0 | 2 mg/ml | 454 | 11.76495198 | 3023 | 5290 | 1.045625788 |
| 214 | 3-F5 | CT115 | Shikonin | 517-89-5 | 288.3 | 2 mg/ml | 610 | 17.34286978 | 2 | 4352 | 1.045253115 |
| 162 | 3-A3 | DL-549 | Meglumine | 3521-84-4 | 195.2 | 2 mg/ml | 182 | 25.61249201 | 3228 | 4352 | 1.044013498 |
| 421 | 6-C2 | DL-181 | Doxofylline | 69975-86-6 | 266.3 | 2 mg/ml | 33 | 18.77873405 | 3226 | 4303 | 1.044003177 |
| 564 | 8-A5 | DL-206 | Tibolone | 5630-53-5 | 312.5 | 2 mg/ml | 684 | 16.00224748 | 2584 | 4361 | 1.043057057 |
| 473 | 6-H4 | DL-431 | Levodopa | 59-92-7 | 197.2 | 2 mg/ml | 251 | 25.35595707 | 3551 | 4303 | 1.042404777 |
| 437 | 6-D8 | DL-395 | Fenoldopam mesylate | 67227-56-9 | 305.8 | 2 mg/ml | 81 | 16.35249062 | 3449 | 4303 | 1.041770576 |
| 154 | 2-H5 | DL-209 | Eprosartan | 133040-01-4 | 424.5 | 2 mg/ml | 160 | 11.77793236 | 3457 | 5627 | 1.0386449 |
| 567 | 8-A8 | DL-517 | Tobramycin (free base) | 32986-56-4 | 467.5 | 2 mg/ml | 691 | 10.69464523 | 2799 | 4361 | 1.037850941 |
| 487 | 7-A8 | DL-445 | Metoprolol tartrate | 56392-17-7 | 267.4 | 2 mg/ml | 255 | 18.70057904 | 3197 | 4940 | 1.037553683 |
| 20 | 1-B11 | AC-120 | Glipizide | 29094-61-9 | 445.5 | 2 mg/ml | 437 | 11.22222511 | 3927 | 5531 | 1.036942137 |
| 526 | 7-E7 | DL-483 | Prednisone | 53-03-2 | 358.4 | 2 mg/ml | 556 | 13.94939945 | 3551 | 4940 | 1.03678805 |
| 39 | 1-D10 | AC-161 | Yohimbine HCl | 146-48-5 | 354.5 | 2 mg/ml | 735 | 14.10624377 | 3881 | 5531 | 1.036293791 |
| 106 | 2-C7 | AC-806 | Idazoxan | 79944-56-2 | 204.2 | 2 mg/ml | 395 | 24.4821427 | 3950 | 5627 | 1.034852745 |
| 233 | 3-H4 | EI-165 | Benserazide HCl | 322-35-0 | 257.2 | 2 mg/ml | 170 | 19.43648574 | 3528 | 4352 | 1.034730876 |
| 349 | 5-C10 | T-117 | Vincristine sulfate | 2068-78-2 | 825.0 | 2 mg/ml | 728 | 6.060752841 | 626 | 4930 | 1.034413759 |
| 135 | 2-F6 | DL-258 | Manidipine | 120092-68-4 | 610.7 | 2 mg/ml | 472 | 8.187107366 | 3704 | 5627 | 1.034120443 |
| 117 | 2-D8 | AC-840 | Metoclopramide HCl | 7232-21-5 | 299.8 | 2 mg/ml | 241 | 16.67759939 | 3640 | 5627 | 1.034082252 |
| 538 | 7-F9 | DL-566 | Nelfinavir Mesylate | 159989-64-7 | 663.9 | 2 mg/ml | 623 | 7.531227709 | 3129 | 4940 | 1.033151485 |
| 628 | 8-G9 | DL-536 | Taurocholic acid, sodium salt hydrate | 81-24-3 | 515.7 | 2 mg/ml | 669 | 9.69527649 | 3078 | 4361 | 1.032215102 |
| 5 | 1-A6 | A-239 | Kasugamycin | 6980-18-3 | 379.4 | 2 mg/ml | 68 | 13.17974363 | 3868 | 5531 | 1.031046544 |
| 63 | 1-G4 | AC-232 | Pancuronium Br | 15500-66-0 | 572.9 | 2 mg/ml | 532 | 8.727839688 | 3597 | 5531 | 1.030984975 |
| 548 | 7-G9 | DL-503 | Sibutramine HCl | 125494-59-9 | 279.9 | 2 mg/ml | 620 | 17.86630125 | 3356 | 4940 | 1.029548705 |
| 546 | 7-G7 | DL-501 | Scopolamine HBr | 114-49-8 | 303.4 | 2 mg/ml | 649 | 16.48200123 | 3410 | 4940 | 1.027058812 |

TABLE 4-10-continued

| | | | | | | | | | | | |
|---|---|---|---|---|---|---|---|---|---|---|---|
| 629 | 8-G10 | SL-230 | Miglustat | 72599-27-0 | 219.3 | 2 mg/ml | 333 | 22.80156749 | 2966 | 4361 | 1.025463612 |
| 404 | 6-A5 | DL-366 | Crotamiton | 483-63-6 | 203.3 | 2 mg/ml | 488 | 24.5958242 | 3264 | 4303 | 1.025355545 |
| 65 | 1-G6 | AC-241 | Physostigmine sulfate | 64-47-1 | 275.4 | 2 mg/ml | 41 | 18.15847497 | 3672 | 5531 | 1.024400669 |

Table 4-11 is a continuation of Table 4-10.

TABLE 4-11

| | | | | | | | | | | | |
|---|---|---|---|---|---|---|---|---|---|---|---|
| 312 | 4-H3 | DL-108 | Fluvastatin Na | 93957-54-1 | 411.5 | 2 mg/ml | 259 | 12.15133211 | 805 | 5290 | 1.024223587 |
| 70 | 1-G11 | AC-779 | Trans-triprolidine HCl | 6138-79-0 | 278.4 | 2 mg/ml | 704 | 17.95973205 | 4144 | 5531 | 1.02362497 |
| 122 | 2-E3 | AC-911 | Carbamylcholine Cl | 51-83-2 | 147.2 | 2 mg/ml | 335 | 33.96770283 | 3858 | 5627 | 1.023493355 |
| 180 | 3-B11 | DL-277 | Anagrelide | 68475-42-3 | 256.1 | 2 mg/ml | 103 | 19.52417325 | 4056 | 4352 | 1.023173844 |
| 138 | 2-F9 | DL-254 | Olmesartan | 144689-63-4 | 558.6 | 2 mg/ml | 519 | 8.950964023 | 3800 | 5627 | 1.022813346 |
| 280 | 4-D11 | DL-236 | Ergotamine D-tartrate | 379-79-3 | 581.7 | 2 mg/ml | 185 | 8.595829922 | 3583 | 5290 | 1.02240815 |
| 330 | 5-A11 | DL-244 | Lomerizine HCl | 101477-55-8 | 468.5 | 2 mg/ml | 346 | 10.67125274 | 1485 | 4930 | 1.022267701 |
| 432 | 6-D3 | DL-170 | Etretinate | 54350-48-0 | 354.5 | 2 mg/ml | 419 | 14.10462103 | 3065 | 4303 | 1.021125974 |
| 619 | 8-F10 | S104 | Conduritol b epoxide | 6090-95-5 | 162.1 | 2 mg/ml | 37 | 30.83686313 | 3331 | 4361 | 1.02104076 |
| 19 | 1-B10 | AC-118 | Pinacidil | 85371-64-8 | 245.3 | 2 mg/ml | 53 | 20.38072166 | 4040 | 5531 | 1.020537688 |
| 542 | 7-G3 | DL-497 | Roxithromycin | 80214-83-1 | 837.1 | 2 mg/ml | 639 | 5.97323558 | 3677 | 4940 | 1.020250018 |
| 394 | 5-H5 | AR-116 | Citalopram | 59729-33-8 | 324.4 | 2 mg/ml | 414 | 15.41299569 | 3008 | 4930 | 1.019988134 |
| 42 | 1-E3 | DL-564 | Emtricitabine | 143491-57-0 | 247.2 | 2 mg/ml | 757 | 20.22247963 | 3766 | 5531 | 1.01940913 |
| 156 | 2-H7 | DL-551 | Ozagrel | 82571-53-7 | 228.3 | 2 mg/ml | 750 | 21.90553728 | 3862 | 5627 | 1.019096149 |
| 417 | 6-B8 | DL-378 | Diflunisal | 22494-42-4 | 250.2 | 2 mg/ml | 361 | 19.98371647 | 3527 | 4303 | 1.018838108 |
| 572 | 8-B3 | DL-521 | Tolmetin Na | 64490-92-2 | 257.3 | 2 mg/ml | 696 | 19.43319586 | 3245 | 4361 | 1.018708402 |
| 446 | 6-E7 | DL-404 | Fluocinolone acetonide | 67-73-2 | 452.5 | 2 mg/ml | 226 | 11.0497262 | 3099 | 4303 | 1.017955327 |
| 47 | 1-E8 | AC-174 | Clenbuterol | 37148-27-9 | 277.2 | 2 mg/ml | 90 | 18.03777442 | 4688 | 5531 | 1.017177264 |
| 356 | 5-D7 | DL-318 | Allopurinol | 315-30-0 | 136.1 | 2 mg/ml | 65 | 36.7339601 | 3361 | 4930 | 1.016923764 |
| 178 | 3-B9 | PG-007 | Dinoprostone | 363-24-6 | 352.5 | 2 mg/ml | 262 | 14.18540161 | 4302 | 4352 | 1.016831942 |
| 153 | 2-H4 | DL-212 | Escitalopram | 128196-01-0 | 324.4 | 2 mg/ml | 199 | 15.41299569 | 3381 | 5627 | 1.016098583 |
| 124 | 2-E5 | AC-915 | Butyrylcholine Cl | 2963-78-2 | 174.3 | 2 mg/ml | 277 | 28.69189354 | 4016 | 5627 | 1.01595962 |
| 145 | 2-G6 | DL-261 | Sildenafil | 139755-83-2 | 474.6 | 2 mg/ml | 634 | 10.53549387 | 3799 | 5627 | 1.014737397 |
| 260 | 4-B11 | GR-210 | Troglitazone | 97322-87-7 | 441.6 | 2 mg/ml | 712 | 11.32373333 | 3459 | 5290 | 1.011471642 |
| 322 | 5-A3 | DL-544 | Etoricoxib | 202409-33-4 | 358.8 | 2 mg/ml | 412 | 13.93341971 | 3601 | 4930 | 1.011198164 |
| 468 | 6-G9 | DL-426 | Itopride HCl | 122892-31-3 | 358.4 | 2 mg/ml | 28 | 13.94928853 | 3763 | 4303 | 1.010794493 |
| 426 | 6-C7 | DL-385 | Ethisterone | 434-03-7 | 312.5 | 2 mg/ml | 345 | 16.00224748 | 3339 | 4303 | 1.010472666 |
| 281 | 4-E2 | DL-291 | Sulindac | 38194-50-2 | 356.4 | 2 mg/ml | 662 | 14.02842929 | 3497 | 5290 | 1.010000074 |
| 410 | 6-A11 | DL--372 | Danazol | 17230-88-5 | 337.5 | 2 mg/ml | 188 | 14.81630786 | 3085 | 4303 | 1.00945183 |
| 173 | 3-B4 | DL-273 | Montelukast | 158966-92-8 | 586.2 | 2 mg/ml | 459 | 8.529525644 | 3436 | 4352 | 1.009136665 |

Table 4-12 is a continuation of Table 4-11.

TABLE 4-12

| | | | | | | | | | | | |
|---|---|---|---|---|---|---|---|---|---|---|---|
| 386 | 5-G7 | DL-348 | Ceftazidime | 72558-82-8 | 546.6 | 2 mg/ml | 327 | 9.147714067 | 3569 | 4930 | 1.009027318 |
| 331 | 5-B2 | DL-138 | Lofexidine | 21498-08-8 | 259.1 | 2 mg/ml | 325 | 19.29480647 | 3658 | 4930 | 1.008563082 |
| 543 | 7-G4 | DL-498 | Rufloxacin | 106017-08-7 | 363.4 | 2 mg/ml | 641 | 13.75842425 | 3646 | 4940 | 1.00822304 |
| 550 | 7-G11 | DL-504 | Spironolactone | 52-01-7 | 416.6 | 2 mg/ml | 640 | 12.00237436 | 3332 | 4940 | 1.007768493 |
| 150 | 2-G11 | DL-264 | Candesartan | 139481-59-7 | 440.5 | 2 mg/ml | 298 | 11.35162944 | 3901 | 5627 | 1.006627197 |
| 40 | 1-D11 | AC-164 | Dihydroergotamine mesylate | 11032-41-0 | 583.7 | 2 mg/ml | 432 | 8.56614194 | 3623 | 5531 | 1.00594313 |
| 433 | 6-D4 | DL-563 | Trichloromethiazide | 133-67-5 | 380.7 | 2 mg/ml | 424 | 13.13516192 | 3381 | 4303 | 1.005709679 |
| 123 | 2-E4 | AC-912 | Carbamyl-beta-methylcholine Cl | 590-63-6 | 161.2 | 2 mg/ml | 332 | 31.01241774 | 3975 | 5627 | 1.005669411 |
| 290 | 4-E11 | J120 | Mephenytoin | 50-12-4 | 218.3 | 2 mg/ml | 399 | 22.90871181 | 3501 | 5290 | 1.003983273 |
| 333 | 5-B4 | DL-205 | Nifekalant HCl | 130636-43-0 | 405.5 | 2 mg/ml | 503 | 12.33174749 | 3562 | 4930 | 1.003501259 |
| 250 | 4-A11 | EI320 | Sodium phenylbutyrate | 1716-12-7 | 186.2 | 2 mg/ml | 753 | 26.85461027 | 3595 | 5290 | 1.003310817 |
| 440 | 6-D11 | DL-398 | Finasteride | 98319-26-7 | 372.6 | 2 mg/ml | 109 | 13.42081666 | 3433 | 4303 | 1.002444372 |
| 431 | 6-D2 | DL-390 | Etidronate 2Na | 7414-83-7 | 204.0 | 2 mg/ml | 354 | 24.50817965 | 3366 | 4303 | 1.001714982 |
| 116 | 2-D7 | DL-558 | Amfebutamone | 34911-55-2 | 239.7 | 2 mg/ml | 742 | 20.85527395 | 3526 | 5627 | 1.001708034 |
| 200 | 3-D11 | CA-225 | Flunarizine-2HCl | 30484-77-6 | 404.5 | 2 mg/ml | 211 | 12.36071575 | 3062 | 4352 | 1.000484085 |
| 326 | 5-A7 | DL-213 | Ibandronate | 114084-78-5 | 319.2 | 2 mg/ml | 230 | 15.66250387 | 3747 | 4930 | 0.999589951 |
| 351 | 5-D2 | DL-313 | Acetylsalicylic acid | 50-78-2 | 180.2 | 2 mg/ml | 57 | 27.75284493 | 3375 | 4930 | 0.997680094 |
| 393 | 5-H4 | DL-355 | Ciprofloxacin | 85721-33-1 | 331.3 | 2 mg/ml | 386 | 15.08979742 | 3892 | 4930 | 0.997536588 |
| 1 | 1-A2 | DL-552 | Moroxydine HCl | 3160-91-6 | 207.7 | 2 mg/ml | 748 | 24.07731167 | 3878 | 5531 | 0.99722472 |
| 563 | 8-A4 | DL-190 | Temozolomide | 85622-93-1 | 194.2 | 2 mg/ml | 674 | 25.75279011 | 2729 | 4361 | 0.996678344 |
| 372 | 5-F3 | T-116 | Vinblastine sulfate | 143-67-9 | 811.0 | 2 mg/ml | 727 | 6.165254264 | 741 | 4930 | 0.994519761 |
| 161 | 3-A2 | AR-103 | Tizanidine HCl | 51322-75-9 | 253.7 | 2 mg/ml | 690 | 19.70718202 | 3281 | 4352 | 0.99376949 |
| 58 | 1-F9 | AC-214 | Pilocarpine HCl | 54-71-7 | 208.3 | 2 mg/ml | 102 | 24.00817776 | 3649 | 5531 | 0.992948705 |
| 227 | 3-G8 | EI-127 | Dipyridamole | 58-32-2 | 504.6 | 2 mg/ml | 314 | 9.908100387 | 4027 | 4930 | 0.992730979 |
| 237 | 3-H8 | EI-180 | Neomycin sulfate | 1405-10-3 | 614.7 | 2 mg/ml | 494 | 8.134638418 | 3484 | 4352 | 0.992072921 |
| 215 | 3-F6 | D-102 | Bromocriptine mesylate | 22260-51-1 | 654.6 | 2 mg/ml | 238 | 7.638134517 | 3228 | 4352 | 0.991102429 |
| 125 | 2-E6 | AC-925 | Famotidine | 76824-35-6 | 337.4 | 2 mg/ml | 456 | 14.81716581 | 3670 | 5627 | 0.990592254 |
| 43 | 1-E4 | AC-169 | Betaxotol HCl | 63659-19-8 | 307.4 | 2 mg/ml | 179 | 16.26350892 | 3991 | 5531 | 0.990435828 |
| 501 | 7-C2 | DL-459 | Norfloxacin | 70458-96-7 | 319.2 | 2 mg/ml | 178 | 15.65736377 | 3625 | 4940 | 0.990112519 |

Table 4-13 is a continuation of Table 4-12.

TABLE 4-13

| | | | | | | | | | | | |
|---|---|---|---|---|---|---|---|---|---|---|---|
| 190 | 3-C11 | C-112 | Gallamine triethiodide | 65-29-2 | 510.8 | 2 mg/ml | 352 | 9.78797293 | 3481 | 4352 | 0.989145605 |
| 561 | 8-A2 | DL-514 | Tetracycline | 60-54-8 | 444.4 | 2 mg/ml | 680 | 11.24998138 | 3102 | 4361 | 0.988225706 |
| 384 | 5-G5 | DL-346 | Cefoperazone acid | 62893-19-0 | 645.7 | 2 mg/ml | 340 | 7.743804708 | 4017 | 4930 | 0.987788853 |
| 96 | 2-B7 | AC-751 | Domperidone | 57808-66-9 | 425.9 | 2 mg/ml | 239 | 11.73924195 | 3927 | 5627 | 0.987539696 |
| 354 | 5-D5 | DL-316 | Acycloguanosine | 59277-89-3 | 225.2 | 2 mg/ml | 59 | 22.20164179 | 3386 | 4930 | 0.987434293 |
| 208 | 3-E9 | DL-281 | Latanoprost | 130209-82-4 | 432.6 | 2 mg/ml | 168 | 11.55786898 | 3355 | 4352 | 0.987252914 |
| 327 | 5-A8 | DL-202 | Imipenem | 64221-86-9 | 299.4 | 2 mg/ml | 413 | 16.70280095 | 3759 | 4930 | 0.98696121 |
| 89 | 2-A10 | AC-741 | Mecamylamine HCl | 826-39-1 | 167.3 | 2 mg/ml | 143 | 29.88701751 | 3575 | 5627 | 0.986404772 |
| 423 | 6-C4 | PI-152 | Enalapril | 75847-73-3 | 376.5 | 2 mg/ml | 114 | 13.28174491 | 3515 | 4303 | 0.98624125 |
| 212 | 3-F3 | CR110 | Pravadoline | 92623-83-1 | 378.5 | 2 mg/ml | 410 | 13.21090279 | 3403 | 4352 | 0.985697957 |
| 30 | 1-C11 | AC-136 | Cirazoline HCl | 40600-13-3 | 216.3 | 2 mg/ml | 389 | 23.11761684 | 3800 | 5531 | 0.984871977 |
| 496 | 7-B7 | DL-454 | Nabumetone | 42924-53-8 | 228.3 | 2 mg/ml | 22 | 21.9016243 | 3581 | 4940 | 0.98484544 |
| 192 | 3-D3 | CA-200 | Amiloride | 2016-88-8 | 229.6 | 2 mg/ml | 85 | 21.77416222 | 3198 | 4352 | 0.983589974 |
| 240 | 3-H11 | EI-216 | Docebenone | 80809-81-0 | 326.4 | 2 mg/ml | 453 | 15.31677057 | 2365 | 4352 | 0.98213773 |
| 157 | 2-H8 | DL-217 | Entacapone | 130929-57-6 | 305.3 | 2 mg/ml | 156 | 16.37772269 | 3918 | 5627 | 0.981956978 |
| 336 | 5-B7 | DL-196 | Pamidronic acid | 40391-99-9 | 235.1 | 2 mg/ml | 531 | 21.27014953 | 3882 | 4930 | 0.981721922 |
| 311 | 4-H2 | DL-192 | Enalaprilat | 76420-72-9 | 348.4 | 2 mg/ml | 115 | 14.35122228 | 3680 | 5290 | 0.981394891 |
| 53 | 1-F4 | AC-189 | Pronethalol HCl | 51-02-5 | 229.3 | 2 mg/ml | 564 | 21.80313876 | 3891 | 5531 | 0.981058038 |
| 249 | 4-A10 | EI-318 | Terbinafine HCl | 91161-71-6 | 291.4 | 2 mg/ml | 759 | 17.15618407 | 2570 | 5290 | 0.979599083 |
| 293 | 4-F4 | KC-125 | Minoxidil | 38304-91-5 | 209.3 | 2 mg/ml | 404 | 23.89454287 | 3057 | 5290 | 0.979418493 |
| 454 | 6-F5 | DL-412 | Gatifloxacin | 112811-59-3 | 375.4 | 2 mg/ml | 376 | 13.31900954 | 3536 | 4303 | 0.979414164 |
| 80 | 1-H11 | AC-508 | Propofol | 2078-54-8 | 178.3 | 2 mg/ml | 593 | 28.04629613 | 3615 | 5531 | 0.979366862 |
| 189 | 3-C10 | C-110 | Tacrine HCl | 1684-40-8 | 198.3 | 2 mg/ml | 665 | 25.21814579 | 3237 | 4352 | 0.979114411 |
| 581 | 8-C2 | DL-529 | Venlafaxine HCl | 99300-78-4 | 277.4 | 2 mg/ml | 724 | 18.023848 | 2866 | 4361 | 0.97800413 |
| 453 | 6-F4 | DL-411 | Ganciclovir | 82410-32-0 | 255.2 | 2 mg/ml | 585 | 19.5897852 | 3183 | 4303 | 0.977523039 |
| 220 | 3-F11 | DM100 | Calcifediol | 19356-17-3 | 400.7 | 2 mg/ml | 280 | 12.47970395 | 744 | 4352 | 0.977023901 |
| 479 | 6-H10 | DL-437 | Lorglumide | 97964-56-2 | 459.4 | 2 mg/ml | 430 | 10.88335064 | 3404 | 4303 | 0.976756084 |
| 71 | 1-H2 | AC-280 | Cimetidine | 51481-61-9 | 252.3 | 2 mg/ml | 379 | 19.8142831 | 3951 | 5531 | 0.976328942 |
| 239 | 3-H10 | EI-213 | Captopril | 62571-86-2 | 217.3 | 2 mg/ml | 311 | 23.01085008 | 120 | 4352 | 0.976258428 |
| 442 | 6-E3 | DL-400 | Flurbiprofen | 5104-49-4 | 244.3 | 2 mg/ml | 234 | 20.46931555 | 3303 | 4303 | 0.975748109 |

Table 4-14 is a continuation of Table 4-13.

TABLE 4-14

| | | | | | | | | | | | |
|---|---|---|---|---|---|---|---|---|---|---|---|
| 472 | 6-H3 | DL-430 | Levonorgestrel | 797-63-7 | 312.5 | 2 mg/ml | 589 | 16.00224748 | 4342 | 4303 | 0.973379693 |
| 438 | 6-D9 | DL-396 | Fenoprofen | 31879-05-7 | 242.3 | 2 mg/ml | 88 | 20.63753217 | 3807 | 4303 | 0.973324462 |
| 247 | 4-A8 | EI-288 | Keloprofen | 22071-15-4 | 254.3 | 2 mg/ml | 83 | 19.66273069 | 3489 | 5290 | 0.971845965 |
| 456 | 6-F7 | DL-414 | Gemfibrozil | 25812-30-0 | 250.3 | 2 mg/ml | 394 | 19.97277391 | 3485 | 4303 | 0.971302374 |
| 397 | 5-H8 | DL-359 | Clinafloxacin HCl | 105956-99-8 | 365.8 | 2 mg/ml | 444 | 13.66886796 | 3716 | 4930 | 0.970430289 |
| 33 | 1-D4 | AC-144 | Naftopidil 2HCl | 57149-07-2 | 392.5 | 2 mg/ml | 485 | 12.73877691 | 3686 | 5531 | 0.968951371 |
| 81 | 2-A2 | AC-554 | Mianserin hcl | 21535-47-7 | 264.4 | 2 mg/ml | 305 | 18.91263686 | 3669 | 5627 | 0.968915746 |
| 22 | 1-C3 | AC-122 | Quinine | 6119-47-7 | 324.4 | 2 mg/ml | 595 | 15.41181225 | 4145 | 5531 | 0.968822029 |
| 87 | 2-A8 | AC-735 | Atropine sulfate | 55-48-1 | 289.4 | 2 mg/ml | 506 | 17.27845291 | 3837 | 5627 | 0.96866694 |
| 91 | 2-B2 | AC-745 | Strychnine HCl | 1421-86-9 | 334.4 | 2 mg/ml | 652 | 14.95118334 | 3678 | 5627 | 0.968275526 |
| 597 | 8-D8 | NS-145 | Ondansetron | 99614-01-4 | 293.4 | 2 mg/ml | 263 | 17.04322944 | 3376 | 4361 | 0.968267341 |
| 68 | 1-G9 | AC-259 | Piribedil HCl | 78213-63-5 | 298.3 | 2 mg/ml | 312 | 16.75898297 | 3965 | 5531 | 0.968074637 |
| 256 | 4-B7 | G-430 | Suramin sodium | 129-46-4 | 1291.3 | 2 mg/ml | 664 | 3.872216754 | 3560 | 5290 | 0.967958181 |
| 414 | 6-B5 | DL-375 | Diclofenac, Na | 15307-79-6 | 296.2 | 2 mg/ml | 357 | 16.88303571 | 3436 | 4303 | 0.967481903 |
| 228 | 3-G9 | EI-128 | Ethacrynic acid | 58-54-8 | 303.1 | 2 mg/ml | 321 | 16.49380118 | 3818 | 4352 | 0.966834893 |
| 385 | 5-G6 | DL-347 | Cefotamine acid | 63527-52-6 | 455.5 | 2 mg/ml | 326 | 10.97764274 | 3475 | 4930 | 0.966732389 |
| 104 | 2-C5 | AC-766 | Ranitidine HCl | 66357-59-3 | 314.4 | 2 mg/ml | 613 | 15.90283799 | 3674 | 5627 | 0.966680475 |
| 366 | 5-E7 | DL-328 | Ampiroxicam | 99464-64-9 | 447.5 | 2 mg/ml | 99 | 11.17392671 | 3560 | 4930 | 0.966190326 |
| 606 | 8-E7 | PD-152 | Milrinone | 78415-72-2 | 211.2 | 2 mg/ml | 355 | 23.67143705 | 3200 | 4361 | 0.965482734 |
| 396 | 5-H7 | DL-358 | Climbazole | 38083-17-9 | 292.8 | 2 mg/ml | 440 | 17.07837272 | 3594 | 4930 | 0.964692099 |
| 499 | 7-B10 | DL-457 | Niflumic acid | 4394-00-7 | 282.2 | 2 mg/ml | 504 | 17.71641881 | 3494 | 4940 | 0.963223749 |
| 252 | 4-B3 | FR-112 | Ambroxol | 18683-91-5 | 378.1 | 2 mg/ml | 77 | 13.2236927 | 3207 | 5290 | 0.96203255 |
| 232 | 3-H3 | EI-164 | Ibuprofen | 15687-27-1 | 206.3 | 2 mg/ml | 435 | 24.2380514 | 3501 | 4352 | 0.961279855 |
| 338 | 5-B9 | DL-310 | Triptorelin | 57773-63-4 | 1311.5 | 2 mg/ml | 711 | 3.812486831 | 3781 | 4930 | 0.960932891 |
| 102 | 2-C3 | AC-763 | Diphenhydramine HCl | 147-24-0 | 255.4 | 2 mg/ml | 282 | 19.57996894 | 3990 | 5627 | 0.960654141 |
| 320 | 4-H11 | DL-546 | Atazanavir | 198904-31-3 | 704.9 | 2 mg/ml | 743 | 7.093464941 | 3546 | 5290 | 0.960442125 |
| 283 | 4-E4 | DL-547 | Calcipotriene | 112965-21-6 | 412.6 | 2 mg/ml | 281 | 12.11774424 | 1637 | 5290 | 0.95970899 |
| 18 | 1-B9 | AC-117 | Tolbutamide | 64-77-7 | 270.4 | 2 mg/ml | 693 | 18.49434846 | 3936 | 5531 | 0.959672646 |
| 341 | 5-C2 | DL-187 | Rocuronium bromide | 119302-91-9 | 529.8 | 2 mg/ml | 630 | 9.43769799 | 3753 | 4930 | 0.957592971 |
| 28 | 1-C9 | AC-130 | Flecainide | 54143-56-5 | 414.4 | 2 mg/ml | 112 | 12.06706537 | 4348 | 5531 | 0.957511107 |

Table 4-15 is a continuation of Table 4-14.

TABLE 4-15

| | | | | | | | | | | | |
|---|---|---|---|---|---|---|---|---|---|---|---|
| 201 | 3-E2 | CA-234 | Gabapentin | 60142-96-3 | 171.2 | 2 mg/ml | 341 | 29.19855684 | 3385 | 4352 | 0.956610942 |
| 38 | 1-D9 | AC-160 | Spiroxatrine | 1054-88-2 | 379.5 | 2 mg/ml | 644 | 13.17652044 | 3716 | 5531 | 0.954990916 |
| 350 | 5-C11 | DL-312 | Acemetacin | 53164-05-9 | 415.8 | 2 mg/ml | 49 | 12.0240372 | 3440 | 4930 | 0.953477871 |
| 346 | 5-C7 | NP-461 | Vinorelbine | 71486-22-1 | 779.0 | 2 mg/ml | 730 | 6.418863201 | 756 | 4930 | 0.952859497 |

TABLE 4-15-continued

| | | | | | | | | | | | |
|---|---|---|---|---|---|---|---|---|---|---|---|
| 198 | 3-D9 | CA-215 | Verapamil | 23313-68-0 | 454.6 | 2 mg/ml | 725 | 10.99831943 | 2810 | 4352 | 0.951456917 |
| 66 | 1-G7 | DL-554 | Nialamide | 51-12-7 | 298.3 | 2 mg/ml | 749 | 16.75898297 | 3940 | 5531 | 0.951275207 |
| 78 | 1-H9 | AC-439 | Aniracetam | 72432-10-1 | 219.2 | 2 mg/ml | 113 | 22.805817 | 4429 | 5531 | 0.950109296 |
| 488 | 7-A9 | DL-446 | Methimazole | 60-56-0 | 114.2 | 2 mg/ml | 64 | 43.79441082 | 3779 | 4940 | 0.95010631 |
| 434 | 6-D5 | DL-392 | Famciclovir | 104227-87-4 | 321.3 | 2 mg/ml | 450 | 15.55990949 | 3588 | 4303 | 0.94998846 |
| 316 | 4-H7 | DL-166 | Granisetron | 109889-09-0 | 312.4 | 2 mg/ml | 474 | 16.00419028 | 3431 | 5290 | 0.94970961 |
| 308 | 4-G9 | DL-164 | Diclazuril | 101831-37-2 | 407.6 | 2 mg/ml | 343 | 12.26554773 | 3898 | 5290 | 0.949157619 |
| 74 | 1-H5 | DL-556 | Zoledronic acid | 118072-93-8 | 272.1 | 2 mg/ml | 755 | 18.3761206 | 3455 | 5531 | 0.948434746 |
| 23 | 1-C4 | AC-123 | Flufenamic acid | 530-78-9 | 281.2 | 2 mg/ml | 204 | 17.77863115 | 3954 | 5531 | 0.947507357 |
| 519 | 7-D10 | DL-476 | Piperacillin | 61477-96-1 | 517.6 | 2 mg/ml | 571 | 9.660623457 | 3579 | 4940 | 0.947504161 |
| 474 | 6-H5 | DL-432 | Levofloxacin HCl | 100986-85-4 | 361.4 | 2 mg/ml | 274 | 13.83599695 | 3231 | 4303 | 0.947418002 |
| 512 | 7-D3 | NS-710 | Paroxetine HCl | 110429-49-8 | 329.4 | 2 mg/ml | 534 | 15.18028639 | 3364 | 4940 | 0.947243065 |
| 136 | 2-F7 | DL-252 | Tolcapone | 134308-13-7 | 273.2 | 2 mg/ml | 694 | 18.29843109 | 3782 | 5627 | 0.946861128 |
| 557 | 7-H8 | DL-160 | Tamsulosin HCl | 106463-17-6 | 408.5 | 2 mg/ml | 667 | 12.23928607 | 3550 | 4940 | 0.946457969 |
| 448 | 6-E9 | DL-406 | Flutamide | 13311-84-7 | 276.2 | 2 mg/ml | 237 | 18.10170202 | 3363 | 4303 | 0.944941502 |
| 340 | 5-B11 | DL-198 | Risedronic acid | 105462-24-6 | 283.1 | 2 mg/ml | 618 | 17.66061678 | 3396 | 4930 | 0.944480182 |
| 27 | 1-C8 | AC-128 | Lidocaine | 6108-05-0 | 234.3 | 2 mg/ml | 284 | 21.33613354 | 3924 | 5531 | 0.944395213 |
| 37 | 1-D8 | AC-154 | Rilmenidine hemifumarate | 54187-04-1 | 180.3 | 2 mg/ml | 629 | 27.73897096 | 3957 | 5531 | 0.943079626 |
| 301 | 4-G2 | DL-301 | Abamectin | 71751-41-2 | 873.1 | 2 mg/ml | 3 | 5.72672088 | 3309 | 5290 | 0.942934361 |
| 67 | 1-G8 | AC-250 | Haloperidol HCl | 52-86-8 | 375.9 | 2 mg/ml | 78 | 13.3023719 | 3283 | 5531 | 0.94230727 |
| 209 | 3-E10 | CM-109 | Ouabain | 11018-89-6 | 584.7 | 2 mg/ml | 279 | 8.551879025 | 3390 | 4352 | 0.942018317 |
| 343 | 5-C4 | DL-176 | Sulbactam | 68373-14-8 | 233.2 | 2 mg/ml | 656 | 21.43672627 | 3575 | 4930 | 0.941264997 |
| 566 | 8-A7 | DL-516 | Tinidazole | 19387-91-8 | 247.3 | 2 mg/ml | 687 | 20.22044245 | 3225 | 4361 | 0.940938995 |
| 59 | 1-F10 | AC-218 | Ipratropium Br | 22254-24-6 | 332.5 | 2 mg/ml | 225 | 15.03908659 | 4011 | 5531 | 0.940156802 |
| 462 | 6-G3 | DL-420 | Hydrocortisone 21-acetate | 50-03-3 | 404.5 | 2 mg/ml | 192 | 12.36069833 | 3649 | 4303 | 0.939505109 |

Table 4-16 is a continuation of Table 4-15.

TABLE 4-16

| | | | | | | | | | | | |
|---|---|---|---|---|---|---|---|---|---|---|---|
| 428 | 6-C9 | BL-093 | Estradiol | 50-28-2 | 272.4 | 2 mg/ml | 244 | 18.35598107 | 2656 | 4303 | 0.938889093 |
| 126 | 2-E7 | AC-928 | Terfenadine | 50679-08-8 | 471.7 | 2 mg/ml | 678 | 10.60020322 | 279 | 5627 | 0.938608243 |
| 25 | 1-C6 | AC-125 | Phenytoin | 57-41-0 | 252.3 | 2 mg/ml | 546 | 19.81963419 | 3963 | 5531 | 0.936703079 |
| 129 | 2-E10 | DL-246 | Amorolfine | 78613-35-1 | 317.5 | 2 mg/ml | 98 | 15.74707923 | 3844 | 5627 | 0.933498688 |
| 580 | 8-B11 | DL-528 | Vecuronium Br | 50700-72-6 | 557.8 | 2 mg/ml | 723 | 8.963073018 | 3273 | 4361 | 0.931794456 |
| 335 | 5-B6 | DL-194 | Oseltamivir | 196618-13-0 | 312.4 | 2 mg/ml | 522 | 16.00447818 | 3897 | 4930 | 0.930834833 |
| 388 | 5-G9 | DL-350 | Chlormadinone acetate | 302-22-7 | 449.0 | 2 mg/ml | 362 | 11.13606183 | 4112 | 4930 | 0.930559729 |
| 401 | 6-A2 | DL-363 | Clobetasol propionate | 25122-46-7 | 467.0 | 2 mg/ml | 460 | 10.70704645 | 3051 | 4303 | 0.930434551 |
| 362 | 5-E3 | DL-324 | DI-aminoglutethimide | 125-84-8 | 232.3 | 2 mg/ml | 418 | 21.52831202 | 3682 | 4930 | 0.929172021 |
| 545 | 7-G6 | DL-500 | Scopolamine n-butylbromide | 149-64-4 | 360.5 | 2 mg/ml | 651 | 13.8704893 | 3414 | 4940 | 0.928722757 |
| 379 | 5-F10 | DL-341 | Buspirone HCl | 33386-08-2 | 385.5 | 2 mg/ml | 252 | 12.96971375 | 3914 | 4930 | 0.925652197 |
| 363 | 5-E4 | DL-325 | 4-aminosalicylic acid | 65-49-6 | 153.1 | 2 mg/ml | 31 | 32.65013151 | 3927 | 4930 | 0.925638387 |
| 622 | 8-G3 | S-520 | Melengestrol acetate | 2919-66-6 | 396.5 | 2 mg/ml | 223 | 12.60934223 | 3402 | 4361 | 0.924253635 |
| 257 | 4-B8 | DL-282 | Goserelin acetate | 145781-92-6 | 1269.4 | 2 mg/ml | 447 | 3.938746102 | 3481 | 5290 | 0.924156734 |
| 137 | 2-F8 | DL-253 | Gestrinone | 16320-04-0 | 308.4 | 2 mg/ml | 406 | 16.21143708 | 3951 | 5627 | 0.92396976 |
| 167 | 3-A8 | B-100 | Flumazenil | 78755-81-4 | 333.3 | 2 mg/ml | 205 | 16.48557102 | 3334 | 4352 | 0.92218228 |
| 9 | 1-A10 | A-256 | Novobiocin Na | 1476-53-5 | 612.6 | 2 mg/ml | 513 | 8.161408236 | 3901 | 5531 | 0.921040001 |
| 353 | 5-D4 | DL-315 | Aceclofenac | 89796-99-6 | 354.2 | 2 mg/ml | 45 | 14.11662495 | 3872 | 4930 | 0.920926571 |
| 229 | 3-G10 | EI-131 | Indomethacin | 53-86-1 | 357.8 | 2 mg/ml | 480 | 13.97441737 | 3625 | 4352 | 0.920711275 |
| 77 | 1-H8 | AC-408 | Memantine HCl | 19982-08-2 | 179.3 | 2 mg/ml | 383 | 27.88500025 | 3630 | 5531 | 0.915736222 |
| 143 | 2-G4 | NA-137 | Lamotrigine | 84057-84-1 | 256.1 | 2 mg/ml | 131 | 19.52395597 | 3616 | 5627 | 0.915452963 |
| 79 | 1-H10 | AC-501 | Riluzole HCl | 1744-22-5 | 234.2 | 2 mg/ml | 631 | 21.34917841 | 3088 | 5531 | 0.914509341 |
| 204 | 3-E5 | CA-305 | Phenoxybenzamine HCl | 63-92-3 | 303.8 | 2 mg/ml | 417 | 16.45629271 | 3736 | 4352 | 0.912899056 |
| 504 | 7-C5 | DL-106 | Oltipraz | 64224-21-1 | 226.3 | 2 mg/ml | 520 | 22.09042388 | 3600 | 4940 | 0.909397243 |
| 449 | 6-E10 | DL-407 | Fluconazole | 86386-73-4 | 306.3 | 2 mg/ml | 203 | 16.32509187 | 3591 | 4303 | 0.908986259 |
| 213 | 3-F4 | CT110 | Tranilast | 53902-12-8 | 327.3 | 2 mg/ml | 702 | 15.27464312 | 3720 | 4352 | 0.907366883 |
| 315 | 4-H6 | DL-243 | Ginkgolide a | 15291-75-5 | 408.4 | 2 mg/ml | 416 | 12.24263292 | 3561 | 5290 | 0.906948111 |
| 242 | 4-A3 | EI-219 | Piroxicam | 36322-90-4 | 331.4 | 2 mg/ml | 169 | 15.08966763 | 3793 | 5290 | 0.905024596 |
| 297 | 4-F8 | DL-221 | Bromebric acid | 16170-76-6 | 285.1 | 2 mg/ml | 231 | 17.53795336 | 3911 | 5290 | 0.904246558 |

Table 4-17 is a continuation of Table 4-16.

TABLE 4-17

| | | | | | | | | | | | |
|---|---|---|---|---|---|---|---|---|---|---|---|
| 183 | 3-C4 | AC-227 | Lobeline | 90-69-7 | 337.5 | 2 mg/ml | 315 | 14.81630786 | 3100 | 4352 | 0.903196994 |
| 223 | 3-G4 | EI-114 | Oxatomide | 60607-34-3 | 426.6 | 2 mg/ml | 525 | 11.72150593 | 3155 | 4352 | 0.90238694 |
| 402 | 6-A3 | DL-364 | Closantel | 57808-65-8 | 663.1 | 2 mg/ml | 17 | 7.540524134 | 3506 | 4303 | 0.900918749 |
| 277 | 4-D8 | DL-287 | Pranlukast | 103177-37-3 | 481.5 | 2 mg/ml | 209 | 10.38388259 | 3435 | 5290 | 0.900459646 |
| 288 | 4-E9 | DL-161 | Bambuterol | 81732-65-2 | 367.4 | 2 mg/ml | 166 | 13.60733313 | 3715 | 5290 | 0.898480586 |
| 595 | 8-D6 | NS-109 | Fluperlapine | 67121-76-0 | 309.4 | 2 mg/ml | 229 | 16.16084566 | 3074 | 4361 | 0.898284379 |
| 605 | 8-E6 | PD-141 | Irsogladine maleate | 57381-26-7 | 256.1 | 2 mg/ml | 670 | 19.52395597 | 3312 | 4361 | 0.898268861 |
| 415 | 6-B6 | DL-376 | 2',3'-dideoxycytidine | 7481-89-2 | 211.2 | 2 mg/ml | 6 | 23.67174748 | 3475 | 4303 | 0.89779101 |
| 218 | 3-F9 | D-109 | Quinpirole HCl (−)- | 85760-74-3 | 219.3 | 2 mg/ml | 599 | 22.79644751 | 3761 | 4352 | 0.896944187 |

TABLE 4-17-continued

| | | | | | | | | | | | |
|---|---|---|---|---|---|---|---|---|---|---|---|
| 452 | 6-F3 | DL-410 | Furosemide | | 54-31-9 | 330.7 | 2 mg/ml | 294 | 15.11720962 | 3895 | 4303 | 0.895842738 |
| 84 | 2-A5 | DL-561 | nateglinide | | 105816-04-4 | 317.4 | 2 mg/ml | 566 | 15.751408 | 3809 | 5627 | 0.894848357 |
| 35 | 1-D6 | AC-152 | Clonidine HCl | | 4205-91-8 | 230.1 | 2 mg/ml | 469 | 21.72985462 | 4136 | 5531 | 0.894201589 |
| 253 | 4-B4 | FR114 | Idebenone | | 58186-27-9 | 338.4 | 2 mg/ml | 431 | 14.77332039 | 2486 | 5290 | 0.893135387 |
| 420 | 6-B11 | DL-380 | Doxifluridine | | 3094-09-5 | 246.2 | 2 mg/ml | 446 | 20.30895444 | 3672 | 4303 | 0.888312524 |
| 599 | 8-D10 | DL-562 | Tiotropium Br | | 136310-93-5 | 472.4 | 2 mg/ml | 167 | 10.58372436 | 3450 | 4361 | 0.885587182 |
| 406 | 6-A7 | DL-368 | Cyproterone acetate | | 427-51-0 | 416.9 | 2 mg/ml | 587 | 11.99186481 | 3604 | 4303 | 0.883618335 |
| 395 | 5-H6 | DL-357 | Clarithromycin | | 81103-11-9 | 748.0 | 2 mg/ml | 426 | 6.684737473 | 3782 | 4930 | 0.881779446 |
| 207 | 3-E8 | DL-131 | Miltefosine | | 58066-85-6 | 407.6 | 2 mg/ml | 369 | 12.26756431 | 3677 | 4352 | 0.880978036 |
| 358 | 5-D9 | DL-320 | Altretamine | | 645-05-6 | 210.3 | 2 mg/ml | 548 | 23.77736662 | 4029 | 4930 | 0.880446665 |
| 427 | 6-C8 | DL-386 | Esomeprazole | | 119141-88-7 | 345.4 | 2 mg/ml | 240 | 14.47499427 | 3677 | 4303 | 0.879982815 |
| 305 | 4-G6 | DL-162 | Bicalutamide | | 90357-06-5 | 430.4 | 2 mg/ml | 186 | 11.61761647 | 3892 | 5290 | 0.879476573 |
| 2 | 1-A3 | A-190 | Clindamycin HCl | | 21462-39-5 | 425.0 | 2 mg/ml | 445 | 11.76495198 | 3858 | 5531 | 0.878795179 |
| 430 | 6-C11 | BL-090 | Estrone | | 53-16-7 | 270.4 | 2 mg/ml | 300 | 18.49284497 | 3156 | 4303 | 0.878561752 |
| 31 | 1-D2 | AC-138 | Oxymetazoline HCl | | 2315-02-8 | 260.4 | 2 mg/ml | 350 | 19.20252085 | 4199 | 5531 | 0.878314397 |
| 15 | 1-B6 | AC-109 | Pimozide | | 2062-78-4 | 461.6 | 2 mg/ml | 425 | 10.83283649 | 3602 | 5531 | 0.877950741 |
| 508 | 7-C9 | DL-465 | Oxacillin sodium monohydrate | | 7240-38-2 | 400.4 | 2 mg/ml | 293 | 12.48637705 | 3767 | 4940 | 0.877909406 |
| 364 | 5-E5 | DL-326 | 5-aminosalicylic acid | | 89-57-6 | 153.1 | 2 mg/ml | 34 | 32.65013151 | 3928 | 4930 | 0.877441514 |
| 188 | 3-C9 | C-109 | Oxotremorine sesquifumarate | | 17360-35-9 | 206.3 | 2 mg/ml | 344 | 24.23771654 | 3867 | 4352 | 0.87722537 |
| 151 | 2-H2 | DL-101 | Butenafine | | 101828-21-1 | 317.5 | 2 mg/ml | 276 | 15.74910591 | 3592 | 5627 | 0.87655312 |

Table 4-18 is a continuation of Table 4-17.

TABLE 4-18

| | | | | | | | | | | | |
|---|---|---|---|---|---|---|---|---|---|---|---|
| 285 | 4-E6 | DL-295 | Zileuton | | 111406-87-2 | 236.3 | 2 mg/ml | 739 | 21.16003636 | 3595 | 5290 | 0.875950257 |
| 291 | 4-F2 | KC-115 | Diazoxide | | 364-98-7 | 230.7 | 2 mg/ml | 322 | 21.67559362 | 3792 | 5290 | 0.875618181 |
| 12 | 1-B3 | AC-104 | Bepridil | | 74764-40-2 | 366.6 | 2 mg/ml | 511 | 13.64065251 | 2664 | 5531 | 0.874980688 |
| 339 | 5-B10 | NP-526 | Rifamycin sv | | 6998-60-3 | 696.8 | 2 mg/ml | 584 | 7.175879824 | 3821 | 4930 | 0.873727406 |
| 300 | 4-F11 | DL-300 | Letrozole | | 112809-51-5 | 285.3 | 2 mg/ml | 180 | 17.52475336 | 3725 | 5290 | 0.873316695 |
| 282 | 4-E3 | DL-292 | Valproic acid | | 99-66-1 | 144.2 | 2 mg/ml | 720 | 34.67033229 | 3654 | 5290 | 0.872956284 |
| 193 | 3-D4 | CA-202 | Amlodipine | | 88150-42-9 | 408.9 | 2 mg/ml | 97 | 12.22835773 | 3638 | 4352 | 0.872263773 |
| 317 | 4-H8 | DL-105 | Nedaplatin | | 95734-82-0 | 303.2 | 2 mg/ml | 493 | 16.49143636 | 3606 | 5290 | 0.871858344 |
| 44 | 1-E5 | AC-171 | Practolol | | 6673-35-4 | 266.3 | 2 mg/ml | 126 | 18.77278265 | 4078 | 5531 | 0.867690682 |
| 458 | 6-F9 | DL-416 | Glimepiride | | 93479-97-1 | 490.6 | 2 mg/ml | 436 | 10.19105414 | 3728 | 4303 | 0.866489362 |
| 463 | 6-G4 | DL-421 | 17-hydroxyprogesterone | | 68-96-2 | 330.5 | 2 mg/ml | 14 | 15.12990003 | 3290 | 4303 | 0.865994297 |
| 211 | 3-F2 | CN-244 | Molsidomine | | 25717-80-0 | 242.2 | 2 mg/ml | 455 | 20.64099964 | 3514 | 4352 | 0.86575851 |
| 592 | 8-D3 | NS-102 | Cinanserin | | 1166-34-3 | 340.5 | 2 mg/ml | 384 | 14.6846725 | 3293 | 4361 | 0.865527858 |
| 292 | 4-F3 | KC-120 | Glyburide | | 10238-21-8 | 494.0 | 2 mg/ml | 441 | 10.1211766 | 3706 | 5290 | 0.865161801 |
| 46 | 1-E7 | AC-173 | Xamoterol hemifumarate | | 73210-73-8 | 339.4 | 2 mg/ml | 733 | 14.73210767 | 4274 | 5531 | 0.864243199 |
| 29 | 1-C10 | AC-131 | Phenamil | | 2038-35-9 | 305.7 | 2 mg/ml | 545 | 16.35436695 | 4494 | 5531 | 0.864179707 |
| 181 | 3-C2 | DL-278 | Dofetilide | | 115256-11-6 | 441.6 | 2 mg/ml | 146 | 11.32317813 | 3730 | 4352 | 0.863856218 |
| 455 | 6-F6 | DL-413 | Gentamycin sulfate | | 1405-41-0 | 477.6 | 2 mg/ml | 398 | 10.4688767 | 3459 | 4303 | 0.86296421 |
| 101 | 2-C2 | AC-760 | Sulpiride s (−) | | 23672-07-3 | 341.4 | 2 mg/ml | 663 | 14.64419326 | 3782 | 5627 | 0.862856671 |
| 374 | 5-F5 | DL-336 | Aztreonam | | 78110-38-0 | 435.4 | 2 mg/ml | 164 | 11.48271367 | 3727 | 4930 | 0.862363652 |
| 186 | 3-C7 | EI-233 | Fasudil | | 103745-39-7 | 291.4 | 2 mg/ml | 457 | 17.160472 | 3468 | 4352 | 0.860413294 |
| 3 | 1-A4 | A-192 | Clindamycin PO4 | | 35208-55-0 | 663.4 | 2 mg/ml | 448 | 7.536839961 | 4024 | 5531 | 0.860199544 |
| 590 | 8-C11 | NO-102 | Naloxonazine 2HCl | | 82824-01-9 | 650.8 | 2 mg/ml | 38 | 7.683068625 | 3142 | 4361 | 0.859376357 |
| 14 | 1-B5 | AC-108 | Nicardipine | | 54527-84-3 | 479.5 | 2 mg/ml | 497 | 10.42671259 | 4070 | 5531 | 0.857242752 |
| 491 | 7-B2 | DL-449 | Minocycline HCl | | 10118-90-8 | 457.5 | 2 mg/ml | 390 | 10.92925941 | 3723 | 4940 | 0.855177004 |
| 179 | 3-B10 | DL-276 | Metformin | | 657-24-9 | 129.2 | 2 mg/ml | 2 | 38.70994614 | 3788 | 4352 | 0.8550975 |
| 352 | 5-D3 | DL-314 | Acipimox | | 51037-30-0 | 154.1 | 2 mg/ml | 58 | 32.44092248 | 3854 | 4930 | 0.854913554 |
| 465 | 6-G6 | DL-423 | Ifosfamide | | 3778-73-2 | 261.1 | 2 mg/ml | 347 | 19.15051385 | 3845 | 4303 | 0.853784324 |
| 6 | 1-A7 | A-240 | Lincomycin | | 154-21-2 | 406.5 | 2 mg/ml | 290 | 12.29874699 | 3884 | 5531 | 0.85175097 |

Table 4-19 is a continuation of Table 4-18.

TABLE 4-19

| | | | | | | | | | | | |
|---|---|---|---|---|---|---|---|---|---|---|---|
| 516 | 7-D7 | DL-473 | Pentoxifylline | | 6493-05-6 | 278.3 | 2 mg/ml | 538 | 17.96535783 | 3878 | 4940 | 0.850803206 |
| 41 | 1-E2 | AC-165 | Nicergoline | | 27848-84-6 | 484.4 | 2 mg/ml | 575 | 10.32210926 | 3812 | 5531 | 0.850742508 |
| 21 | 1-C2 | AC-121 | PhentolamineHCl | | 73-05-2 | 281.4 | 2 mg/ml | 420 | 17.77079709 | 3946 | 5531 | 0.848862717 |
| 11 | 1-B2 | A-280 | Spectinomycin | | 21736-83-4 | 332.4 | 2 mg/ml | 632 | 15.04408307 | 3970 | 5531 | 0.848019914 |
| 88 | 2-A9 | AC-737 | Decamethonium 2Br | | 541-22-0 | 258.5 | 2 mg/ml | 550 | 19.34275934 | 3676 | 5627 | 0.848001798 |
| 72 | 1-H3 | AC-282 | Tiotidine | | 69014-14-8 | 312.4 | 2 mg/ml | 689 | 16.00406529 | 3955 | 5531 | 0.847439599 |
| 391 | 5-H2 | DL-353 | Chloroquine phosphate | | 50-63-5 | 319.9 | 2 mg/ml | 363 | 15.63081173 | 1425 | 4930 | 0.847341595 |
| 477 | 6-H8 | DL-435 | Lomefloxacin HCl | | 98079-52-8 | 351.4 | 2 mg/ml | 154 | 14.23057771 | 3854 | 4303 | 0.845872371 |
| 295 | 4-F6 | KC-152 | Nicorandil | | 65141-46-0 | 211.2 | 2 mg/ml | 574 | 23.67663811 | 3867 | 5290 | 0.845476715 |
| 210 | 3-E11 | CM-112 | Clopamide | | 636-54-4 | 345.9 | 2 mg/ml | 471 | 14.45710115 | 3791 | 4352 | 0.845450133 |
| 194 | 3-D5 | CA-205 | Diltiazem | | 33286-22-5 | 414.5 | 2 mg/ml | 477 | 12.06192535 | 3713 | 4352 | 0.844922239 |
| 310 | 4-G11 | DL-199 | Dolasetron | | 115956-12-2 | 324.4 | 2 mg/ml | 235 | 15.41388517 | 3630 | 5290 | 0.844028477 |
| 306 | 4-G7 | DL-180 | Clodronate disodium | | 10596-23-3 | 244.9 | 2 mg/ml | 465 | 20.41707761 | 3699 | 5290 | 0.842725479 |
| 265 | 4-C6 | GR-306 | Rifampicin | | 38776-75-9 | 823.0 | 2 mg/ml | 760 | 6.075619764 | 3879 | 5290 | 0.841018412 |

TABLE 4-19-continued

| 230 | 3-G11 | EI-133 | Naproxen | 22204-53-1 | 230.3 | 2 mg/ml | 492 | 21.71402902 | 3884 | 4352 | 0.84034922 |
|---|---|---|---|---|---|---|---|---|---|---|---|
| 148 | 2-G9 | DL-191 | Celepime | 88040-23-7 | 480.6 | 2 mg/ml | 339 | 10.4043477 | 4053 | 5627 | 0.83920257 |
| 383 | 5-G4 | DL-345 | Carbamazepine | 298-46-4 | 236.3 | 2 mg/ml | 324 | 21.16172002 | 3941 | 4930 | 0.837664289 |
| 598 | 8-D9 | NS-515 | Ketanserin tartrate | 74050-98-9 | 395.4 | 2 mg/ml | 71 | 12.64422829 | 3251 | 4361 | 0.837059608 |
| 175 | 3-B6 | DL-275 | Vatalanib | 212141-54-3 | 346.8 | 2 mg/ml | 722 | 14.41660262 | 2326 | 4352 | 0.835361434 |
| 187 | 3-C8 | C-106 | Hydroxytacrine maleate | 112964-99-5 | 214.3 | 2 mg/ml | 227 | 23.33511754 | 4056 | 4352 | 0.834268975 |
| 584 | 8-C5 | NA-103 | Benzamil | 2898-76-2 | 319.8 | 2 mg/ml | 510 | 15.63693147 | 2764 | 4361 | 0.833088485 |
| 141 | 2-G2 | DL-257 | Olanzapine | 132539-06-1 | 312.4 | 2 mg/ml | 516 | 16.00308539 | 3911 | 5627 | 0.832761409 |
| 174 | 3-B5 | EI-240 | Selegiline | 14611-51-9 | 187.3 | 2 mg/ml | 655 | 26.6969745 | 3674 | 4352 | 0.831374618 |
| 284 | 4-E5 | DL-294 | Zafirlukast | 107753-78-6 | 575.7 | 2 mg/ml | 736 | 8.685242571 | 3543 | 5290 | 0.831323412 |
| 621 | 8-G2 | S-515 | Megestrol acetate | 595-33-5 | 384.5 | 2 mg/ml | 580 | 13.00321668 | 3787 | 4361 | 0.830933611 |
| 45 | 1-E6 | AC-172 | Timolol maleate (s) | 26921-17-5 | 316.4 | 2 mg/ml | 686 | 15.80152126 | 4063 | 5531 | 0.82909403 |
| 576 | 8-B7 | DL-525 | Trimethoprim | 738-70-5 | 290.3 | 2 mg/ml | 710 | 17.22210481 | 3404 | 4361 | 0.828969825 |
| 121 | 2-E2 | AC-893 | Nalbuphine HCl | 59052-16-3 | 357.5 | 2 mg/ml | 427 | 13.9878279 | 4002 | 5627 | 0.828433745 |
| 32 | 1-D3 | AC-142 | Ifenprodil | 23210-56-2 | 325.5 | 2 mg/ml | 273 | 15.36311459 | 3982 | 5531 | 0.827639882 |
| 319 | 4-H10 | DL-174 | Anetnole, trans- | 104-46-1 | 148.2 | 2 mg/ml | 703 | 33.73670285 | 3762 | 5290 | 0.827063694 |

Table 4-20 is a continuation of Table 4-19.

TABLE 4-20

| 113 | 2-D4 | AC-613 | Imipramine HCl | 113-52-0 | 280.4 | 2 mg/ml | 428 | 17.8306179 | 3986 | 5627 | 0.826869492 |
|---|---|---|---|---|---|---|---|---|---|---|---|
| 105 | 2-C6 | AC-770 | Naltrindole HCl | 111469-81-9 | 414.5 | 2 mg/ml | 490 | 12.06247241 | 3917 | 5627 | 0.826560457 |
| 527 | 7-E8 | DL-484 | Pregnenolone | 145-13-1 | 316.5 | 2 mg/ml | 557 | 15.7983878 | 3448 | 4940 | 0.825083643 |
| 26 | 1-C7 | AC-127 | Procainamide | 614-39-1 | 235.3 | 2 mg/ml | 559 | 21.24659555 | 4211 | 5531 | 0.821713595 |
| 585 | 8-C6 | NA-139 | Bupivacaine HCl | 14252-80-3 | 288.4 | 2 mg/ml | 30 | 17.33482838 | 3039 | 4361 | 0.820582612 |
| 269 | 4-C10 | GR-314 | Delavirdine mesylate | 147221-93-0 | 456.6 | 2 mg/ml | 269 | 10.95120262 | 3382 | 5290 | 0.818777419 |
| 4 | 1-A5 | A-195 | Cyclosporin A | 59865-13-3 | 1202.6 | 2 mg/ml | 70 | 4.157511584 | 3693 | 5531 | 0.816836509 |
| 57 | 1-F8 | DL-553 | Canthaxanthin | 514-78-3 | 564.9 | 2 mg/ml | 745 | 8.851762786 | 3915 | 5531 | 0.816437529 |
| 587 | 8-CB | NH-106 | Ketotifen fumarate | 34580-14-8 | 309.4 | 2 mg/ml | 116 | 16.15856699 | 3463 | 4361 | 0.815032987 |
| 275 | 4-D6 | DL-285 | Methyl salicylate | 119-36-8 | 152.2 | 2 mg/ml | 73 | 32.86205639 | 3675 | 5290 | 0.814008317 |
| 409 | 6-A10 | DL-371 | Dacarbazine | 4342-03-4 | 182.2 | 2 mg/ml | 184 | 27.44444969 | 3830 | 4303 | 0.813386494 |
| 489 | 7-A10 | DL-447 | Metronidazole | 443-48-1 | 171.2 | 2 mg/ml | 577 | 29.21295679 | 3748 | 4940 | 0.812670053 |
| 574 | 8-B5 | DL-523 | Tramadol HCl | 27203-92-5 | 263.4 | 2 mg/ml | 701 | 18.98375048 | 3747 | 4361 | 0.81261827 |
| 149 | 2-G10 | DL-178 | Aripiprazole | 129722-12-9 | 448.4 | 2 mg/ml | 133 | 11.1508443 | 3240 | 5627 | 0.818876527 |
| 429 | 6-C10 | DL-388 | Estriol | 50-27-1 | 288.4 | 2 mg/ml | 245 | 17.33762224 | 3711 | 4303 | 0.810492454 |
| 348 | 5-C9 | DL-210 | Salmeterol | 89365-50-4 | 415.6 | 2 mg/ml | 645 | 12.03143747 | 4325 | 4930 | 0.810094503 |
| 309 | 4-G10 | DL-302 | Didanosine | 69655-05-6 | 236.2 | 2 mg/ml | 358 | 21.16562124 | 3924 | 5290 | 0.809844966 |
| 36 | 1-D7 | AC-153 | Guanabenz acetate | 5051-62-7 | 231.1 | 2 mg/ml | 12 | 21.6369888 | 4065 | 5531 | 0.809548771 |
| 304 | 4-G5 | DL-144 | Anastrozole | 120511-73-1 | 293.4 | 2 mg/ml | 104 | 17.04306387 | 3567 | 5290 | 0.806630684 |
| 56 | 1-F7 | AC-194 | Nisoxetine HCl | 57754-86-6 | 271.4 | 2 mg/ml | 507 | 18.42554323 | 4059 | 5531 | 0.805484546 |
| 324 | 5-A5 | DL-219 | Cabergoline | 81409-90-7 | 451.6 | 2 mg/ml | 278 | 11.07132593 | 3294 | 4930 | 0.801571305 |
| 573 | 8-B4 | DL-522 | Toltrazuril | 69004-03-1 | 425.4 | 2 mg/ml | 697 | 11.75394259 | 3520 | 4361 | 0.800769364 |
| 471 | 6-H2 | DL-429 | Levamisole HCl | 16595-80-5 | 204.3 | 2 mg/ml | 212 | 24.47432934 | 3833 | 4303 | 0.800367153 |
| 120 | 2-D11 | AC-891 | Levallorphan tartrate | 71-82-9 | 283.4 | 2 mg/ml | 190 | 17.64183684 | 3532 | 5627 | 0.797215133 |
| 373 | 5-F4 | DL-335 | Azithromycin | 83905-01-5 | 749.0 | 2 mg/ml | 155 | 6.67553409 | 3632 | 4930 | 0.797151593 |
| 114 | 2-D5 | AC-814 | Amoxapine | 14028-44-5 | 313.8 | 2 mg/ml | 547 | 15.93424536 | 3721 | 5627 | 0.796965819 |
| 73 | 1-H4 | DL-555 | Zonisamide | 68291-97-4 | 212.2 | 2 mg/ml | 756 | 23.55950585 | 3961 | 5531 | 0.793685158 |
| 222 | 3-G3 | EI-107 | Ketoconazole | 65277-42-1 | 531.4 | 2 mg/ml | 82 | 9.408338565 | 3122 | 4352 | 0.792990814 |
| 279 | 4-D10 | DL-289 | Rofecoxib | 162011-90-7 | 314.4 | 2 mg/ml | 633 | 15.90519334 | 3381 | 5290 | 0.790019508 |
| 378 | 5-F9 | DL-340 | Bromhexine HCl | 611-75-6 | 376.1 | 2 mg/ml | 518 | 13.2930324 | 3661 | 4930 | 0.783858348 |

Table 4-21 is a continuation of Table 4-20.

TABLE 4-21

| 594 | 8-D5 | NS-108 | Dihydroergocristine mesylate | 24730-10-7 | 611.7 | 2 mg/ml | 586 | 8.17330653 | 3229 | 4361 | 0.774703516 |
|---|---|---|---|---|---|---|---|---|---|---|---|
| 258 | 4-B9 | DL-283 | Guaiacol | 90-05-1 | 124.1 | 2 mg/ml | 249 | 40.27690858 | 3887 | 5290 | 0.772924515 |
| 551 | 7-H2 | DL-505 | Stanozolol | 10418-03-8 | 328.5 | 2 mg/ml | 648 | 15.22060795 | 3671 | 4940 | 0.770943044 |
| 539 | 7-F10 | DL-494 | Rimantadine HCl | 1501-84-4 | 179.3 | 2 mg/ml | 605 | 27.88500025 | 3608 | 4940 | 0.769597906 |
| 523 | 7-E4 | DL-480 | Progesterone | 57-83-0 | 314.5 | 2 mg/ml | 590 | 15.89966421 | 3990 | 4940 | 0.7684953 |
| 278 | 4-D9 | DL-288 | Rivastigmine | 123441-03-2 | 250.3 | 2 mg/ml | 626 | 19.97254654 | 3956 | 5290 | 0.753877214 |
| 13 | 1-B4 | AC-105 | Amiodarone | 1951-25-3 | 645.3 | 2 mg/ml | 96 | 7.748050986 | 3497 | 5531 | 0.752177709 |
| 163 | 3-A4 | AR-107 | Propranolol HCl s(−) | 04199-10-4 | 259.4 | 2 mg/ml | 596 | 19.27887224 | 3883 | 4352 | 0.749891664 |
| 168 | 3-A9 | GR-103 | Fenretinide | 65646-68-6 | 391.6 | 2 mg/ml | 482 | 12.76948693 | 209 | 4352 | 0.749416737 |
| 60 | 1-F11 | AC-220 | Pirenzepine 2HCl | 28797-61-7 | 351.4 | 2 mg/ml | 158 | 14.22833264 | 4106 | 5531 | 0.749389861 |
| 241 | 4-A2 | EI-217 | Tranylcypromine | 1986-47-6 | 133.2 | 2 mg/ml | 705 | 37.53902557 | 3535 | 5290 | 0.749206869 |
| 589 | 8-C10 | NO-101 | Naloxone HCl | 357-08-4 | 327.4 | 2 mg/ml | 486 | 15.27260749 | 3472 | 5531 | 0.746261252 |
| 596 | 8-D7 | NS-140 | Fluoxetine HCl | 56296-78-7 | 309.3 | 2 mg/ml | 228 | 16.16374207 | 2842 | 4361 | 0.743795192 |
| 103 | 2-C4 | AC-765 | Promethazine HCl | 58-33-3 | 284.4 | 2 mg/ml | 563 | 17.57924327 | 3585 | 5627 | 0.743703555 |
| 217 | 3-F8 | D-108 | Clothiapine | 2058-52-8 | 343.9 | 2 mg/ml | 19 | 14.53990252 | 3486 | 4352 | 0.741633402 |
| 62 | 1-G3 | AC-222 | Tropicamide | 1508-75-4 | 284.4 | 2 mg/ml | 714 | 17.58327395 | 4088 | 5531 | 0.739761701 |
| 246 | 4-A7 | EI-287 | Nimesulide | 51803-78-2 | 308.3 | 2 mg/ml | 129 | 16.21718101 | 3984 | 5290 | 0.735639128 |
| 299 | 4-F10 | DL-172 | Levetiracetam | 102767-28-2 | 170.2 | 2 mg/ml | 222 | 29.37496306 | 3985 | 5290 | 0.734915839 |

TABLE 4-21-continued

| 640 | 8-H11 | DL-559 | Benzydamine | 642-72-8 | 309.4 | 2 mg/ml | 173 | 16.15954461 | 2873 | 4361 | 0.732691877 |
| 337 | 5-B8 | DL-197 | Pramipexole | 104632-26-0 | 211.3 | 2 mg/ml | 172 | 23.65955714 | 4151 | 4930 | 0.729868388 |
| 478 | 6-H9 | DL-436 | Loratadine | 79794-75-5 | 382.9 | 2 mg/ml | 400 | 13.05845085 | 2345 | 4303 | 0.728053486 |
| 205 | 3-E6 | CA-310 | Trifluoperazine | 440-17-5 | 407.5 | 2 mg/ml | 708 | 12.26979623 | 256 | 4352 | 0.724331469 |
| 588 | 8-C9 | NH-107 | Levocabastine HCl | 79547-78-7 | 420.5 | 2 mg/ml | 224 | 11.88971208 | 3318 | 4361 | 0.722309799 |
| 130 | 2-E11 | DL-247 | Clemastine fumarate | 14976-57-9 | 343.9 | 2 mg/ml | 434 | 14.53909034 | 3387 | 5627 | 0.7187288 |
| 276 | 4-D7 | GR-240 | Pioglitazone | 112529-15-4 | 356.4 | 2 mg/ml | 162 | 14.02733675 | 4536 | 5290 | 0.717516371 |
| 419 | 6-B10 | DL-204 | Doxazosin mesylate | 77883-43-3 | 451.5 | 2 mg/ml | 439 | 11.07453561 | 3402 | 4303 | 0.717212737 |
| 54 | 1-F5 | AC-192 | Sotalol HCl | 959-24-0 | 272.4 | 2 mg/ml | 616 | 18.35746238 | 3974 | 5531 | 0.715704643 |
| 294 | 4-F5 | KC-135 | Tolazamide | 1156-19-0 | 311.4 | 2 mg/ml | 692 | 16.05622144 | 4477 | 5290 | 0.711525996 |
| 436 | 6-D7 | DL-394 | Fenbufen | 36330-85-5 | 254.3 | 2 mg/ml | 18 | 19.66273069 | 3926 | 4303 | 0.70843363 |

Table 4-22 is a continuation of Table 4-21.

TABLE 4-22

| 262 | 4-C3 | GR243 | Raloxifene HCl | 82640-04-8 | 473.6 | 2 mg/ml | 609 | 10.55752851 | 1665 | 5290 | 0.708040409 |
| 325 | 5-A6 | DL-207 | Dilazep | 35898-87-4 | 604.7 | 2 mg/ml | 540 | 8.268521921 | 3015 | 4930 | 0.704993308 |
| 600 | 8-D11 | NS-531 | Mesoridazine besylate | 32672-69-8 | 386.6 | 2 mg/ml | 463 | 12.93386087 | 3463 | 4361 | 0.704082553 |
| 221 | 3-G2 | DM200 | Calcitriol | 32222-06-3 | 416.6 | 2 mg/ml | 285 | 12.00048204 | 899 | 4352 | 0.702353895 |
| 626 | 8-G7 | DL-534 | Bosentan | 147536-97-8 | 551.6 | 2 mg/ml | 219 | 9.064110964 | 3640 | 4361 | 0.699311155 |
| 413 | 6-B4 | DL-374 | Dextromethorphan HBr | 125-69-9 | 271.4 | 2 mg/ml | 301 | 18.42258122 | 3803 | 4303 | 0.699149884 |
| 251 | 4-B2 | FR-111 | Erogothioneine | 497-30-3 | 229.3 | 2 mg/ml | 194 | 21.80522872 | 3758 | 5290 | 0.694504259 |
| 169 | 3-A10 | DL-269 | Gefitinib | 184475-35-2 | 446.9 | 2 mg/ml | 378 | 11.18786033 | 589 | 4352 | 0.676746786 |
| 450 | 6-E11 | DL-408 | Formestane | 566-48-3 | 302.4 | 2 mg/ml | 260 | 16.53344731 | 3443 | 4303 | 0.675945227 |
| 274 | 4-D5 | DL-284 | Lapatinib | 388082-78-8 | 581.1 | 2 mg/ml | 165 | 8.604809775 | 2721 | 5290 | 0.674794404 |
| 107 | 2-C8 | AC-807 | Spiperone | 749-02-0 | 395.5 | 2 mg/ml | 636 | 12.64283336 | 4648 | 5627 | 0.673262474 |
| 24 | 1-C5 | AC-124 | Propafenone | 54063-53-5 | 341.5 | 2 mg/ml | 565 | 14.64325059 | 4080 | 5531 | 0.672731806 |
| 75 | 1-H6 | AC-322 | Naltrexone HCl | 16676-29-2 | 341.4 | 2 mg/ml | 46 | 14.6451219 | 4005 | 5531 | 0.669873202 |
| 411 | 6-B2 | DL-373 | Dehydroepiandrosterone | 53-43-0 | 288.4 | 2 mg/ml | 258 | 17.33499967 | 3541 | 4303 | 0.665805893 |
| 177 | 3-B8 | DL-239 | Efaroxan | 89197-32-0 | 216.3 | 2 mg/ml | 32 | 23.11761684 | 3978 | 4352 | 0.665437756 |
| 244 | 4-A5 | EI-249 | Troleandomycin | 2751-09-9 | 814.0 | 2 mg/ml | 713 | 6.142590358 | 4219 | 5290 | 0.649976365 |
| 216 | 3-F7 | D-107 | Clozapine | 5786-21-0 | 326.8 | 2 mg/ml | 26 | 15.29838287 | 3153 | 4352 | 0.64713495 |
| 16 | 1-B7 | AC-110 | Loperamide | 34552-83-5 | 477.1 | 2 mg/ml | 740 | 10.48104737 | 3896 | 5531 | 0.625278428 |
| 95 | 2-B6 | AC-749 | Chlorpromazine HCl | 69-09-0 | 318.9 | 2 mg/ml | 366 | 15.68030345 | 4084 | 5627 | 0.624779198 |
| 176 | 3-B7 | CT-100 | Fumagillone | 23110-15-8 | 458.6 | 2 mg/ml | 287 | 10.90377748 | 1296 | 4352 | 0.614764439 |
| 17 | 1-B8 | AC-116 | Fluspirilene | 1841-19-6 | 475.6 | 2 mg/ml | 236 | 10.51332972 | 2838 | 5531 | 0.580866948 |
| 164 | 3-A5 | AR-112 | Carvedilol | 72656-09-3 | 406.5 | 2 mg/ml | 338 | 12.30055208 | 518 | 4352 | 0.57524683 |
| 171 | 3-B2 | DL-271 | Imatinib | 152459-95-5 | 493.6 | 2 mg/ml | 402 | 10.12931653 | 3567 | 4352 | 0.564466886 |
| 199 | 3-D10 | CA-216 | Niguldipine HCl | 113317-61-6 | 609.7 | 2 mg/ml | 128 | 8.200368055 | 3173 | 4352 | 0.532465032 |
| 97 | 2-B8 | AC-753 | Fluphenazine 2HCl | 146-56-5 | 437.5 | 2 mg/ml | 232 | 11.42775594 | 4441 | 5627 | 0.495399649 |
| 55 | 1-F6 | AR-111 | Maprotiline HCl | 10347-81-6 | 277.4 | 2 mg/ml | 588 | 18.02366803 | 4164 | 5531 | 0.443894106 |
| 235 | 3-H6 | EI-167 | Methiothepin maleate | 19728-88-2 | 356.6 | 2 mg/ml | 67 | 14.02305525 | 1036 | 4352 | 0.439367416 |

INDUSTRIAL APPLICABILITY

Multi-color fluorescent reporters are useful tools to visualize patterns of alternative splicing in cultured cells and in living organisms at a single cell resolution. The multi-color reporters have been utilized to search for cis-elements and trans-acting factors involved in the regulation of alternative splicing, and to screen for chemical compounds affecting the splicing patterns. In the present invention, the present inventors describe how to construct fluorescent alternative splicing reporter mini-genes for a nematode Caenorhabditis elegans, cultured cells and mice. The mini-gene construction is based on site-directed recombination and various mini-genes can be easily constructed by assembling modular DNA fragments such as a promoter, tag protein cDNAs, a genomic fragment of interest, fluorescent protein cDNAs, and a 3' cassette in separate vectors. The present inventors also described points to be considered in designing fluorescent alternative splicing reporters. The splicing reporter system can theoretically be applied to any other organisms.

The invention claimed is:

1. A method for detecting an alternative splicing of a specific gene in a mammalian multicellular organism, the method comprising:
   (a) introducing into the multicellular organism a DNA construct such that at least two different reporter genes are inserted into the specific gene which undergoes the alternative splicing, wherein the at least two different reporter genes are connected in tandem at the 3' side of the specific gene in a different reading frame in the DNA construct, and wherein the transcripts of the at least two different reporter genes are each connected in frame to a different exon which is included in at least two different mature mRNAs generated by alternative splicing of the specific gene, wherein the transcripts of the at least two different reporter genes are both present on each of the at least two different mature mRNAs and wherein each reporter gene is translated only when the exon to which it is connected is present on the mature mRNA; and
   (b) detecting the alternative splicing of the specific gene in the multicellular organism by the expression of the reporter genes,
   wherein the mammalian multicellular organism is a rodent, and
   wherein the DNA construct comprises an N-terminal tag.

2. A method for testing whether or not a compound to be tested affects an alternative splicing of a specific gene, the method comprising:
   (a) introducing into a mammalian multicellular organism a DNA construct such that at least two different reporter genes are inserted into the specific gene which undergoes the alternative splicing, wherein the at least two different reporter genes are connected in tandem at the 3' side of the specific gene in a different reading frame in the DNA construct, and wherein the transcripts of the at least two different reporter genes are each connected in frame to a different exon which is included in at least two different mature mRNAs generated by alternative splicing of the specific gene, wherein the transcripts of the at least two different reporter genes are both present on each of the at least two different mature mRNAs and wherein each reporter gene is translated only when the exon to which it is connected is present on the mature mRNA;
   (b) allowing the multicellular organism to contact the compound to be tested;
   (c) detecting the alternative splicing of the specific gene in the multicellular organism by the expression of the reporter genes; and
   (d) determining whether or not the expression of the reporter genes detected in the (c) has changed compared to the expression of the reporter genes in a control which is not allowed to contact the compound to be tested,
   wherein the mammalian multicellular organism is a rodent, and
   wherein the DNA construct comprises an N-terminal tag.

3. A method for identifying a gene region affecting an alternative splicing of a specific gene, the method comprising:
   (a) introducing into a mammalian multicellular organism a DNA construct such that at least two different reporter genes are inserted into the specific gene which undergoes the alternative splicing, wherein the at least two different reporter genes are connected in tandem at the 3' side of the specific gene in a different reading frame in the DNA construct, and wherein the transcripts of the at least two different reporter genes are each connected in frame to a different exon which is included in at least two different mature mRNAs generated by alternative splicing of the specific gene, wherein the transcripts of the at least two different reporter genes are both present on each of the at least two different mature mRNAs and wherein each reporter gene is translated only when the exon to which it is connected is present on the mature mRNA;
   (b) treating the multicellular organism with a mutagen;
   (c) detecting the alternative splicing of the specific gene in the multicellular organism by the expression of the reporter genes;
   (d) selecting an individual in which the expression of the reporter genes detected in the (c) has changed compared to the expression of the reporter genes in a control which is not subjected to the mutagen treatment; and (e) identifying a mutated gene region in the individual, wherein the mammalian multicellular organism is a rodent, and wherein the DNA construct comprises an N-terminal tag.

4. A method for identifying a region in a specific gene affecting an alternative splicing of the specific gene, the method comprising:

(a) introducing into a mammalian multicellular organism a DNA construct such that at least two different reporter genes are inserted into the specific gene into which a mutation has been introduced and which undergoes the alternative splicing, wherein the at least two different reporter genes are connected in tandem at the 3' side of the specific gene in a different reading frame in the DNA construct, and wherein the transcripts of the at least two different reporter genes are each connected in frame to a different exon which is included in at least two different mature mRNAs generated by alternative splicing of the specific gene, wherein the transcripts of the at least two different reporter genes are both present on each of the at least two different mature mRNAs and wherein each reporter gene is translated only when the exon to which it is connected is present on the mature mRNA;

(b) detecting the alternative splicing of the specific gene in the multicellular organism by the expression of the reporter genes; and (c) determining whether or not the expression of the reporter genes detected in the (b) has changed compared to the expression of the reporter genes in a control in which a mutation has not been introduced into the specific gene, wherein the mammalian multicellular organism is a rodent, and wherein the DNA construct comprises an N-terminal tag.

5. The method according to any one of claims 1 to 4, wherein each of the transcripts of the at least two different reporter genes is connected in frame to a mutually exclusive exon which is included in a different transcript as a result of the alternative splicing.

6. The method according to any one of claims 1 to 4, wherein the specific gene is linked to a promoter so that the specific gene functions under the control of the promoter, wherein the promoter is one of a tissue-specific promoter and a developmental stage-specific promoter.

7. The method according to any one of claims 1 to 4, wherein the multicellular organism is a mouse.

8. The method according to any one of claims 1 to 4, wherein the specific gene is fibroblast growth factor-receptor 2 (FGFR2).

9. The method according to any one of claims 1 to 4, wherein the at least two different reporter genes are each a gene encoding a fluorescent protein.

10. The method according to any one of claims 1 to 4, wherein the N-terminal tag comprises Glutathione S-transferase (GST).

* * * * *